(12) United States Patent
Frenkel et al.

(10) Patent No.: US 7,635,774 B2
(45) Date of Patent: Dec. 22, 2009

(54) BENZIMIDAZOLE DERIVATIVES

(75) Inventors: Alexander David Frenkel, Buxton (GB); Sarah Elizabeth Lively, Congleton (GB); Jay P. Powers, Pacifica, CA (US); Andrew Smith, Macclesfield (GB); Daqing Sun, Foster City, CA (US); Craig Tomooka, San Mateo, CA (US); Zhulun Wang, Foster City, CA (US)

(73) Assignee: AMGEN Inc., Thousand Oaks, CA (US)

( * ) Notice: Subject to any disclaimer, the term of this patent is extended or adjusted under 35 U.S.C. 154(b) by 0 days.

(21) Appl. No.: 11/513,614

(22) Filed: Aug. 30, 2006

(65) Prior Publication Data

US 2007/0037803 A1 Feb. 15, 2007

Related U.S. Application Data

(63) Continuation of application No. 10/268,412, filed on Oct. 9, 2002, now Pat. No. 7,132,438.

(60) Provisional application No. 60/327,818, filed on Oct. 9, 2001.

(51) Int. Cl.
*A61K 31/5355* (2006.01)
*C07D 413/06* (2006.01)

(52) U.S. Cl. .................. 544/139; 514/234.5

(58) Field of Classification Search .......... 544/139
See application file for complete search history.

(56) References Cited

U.S. PATENT DOCUMENTS

| | | | |
|---|---|---|---|
| 2,928,833 A | 3/1960 | Leake et al. | |
| 3,880,874 A | 4/1975 | Beard | |
| 3,907,700 A | 9/1975 | Grier | |
| 3,995,050 A | 11/1976 | Amselem | |
| 4,002,623 A | 1/1977 | Kadin | |
| 4,011,236 A | 3/1977 | Grier | |
| 4,088,768 A | 5/1978 | Paget et al. | |
| 4,492,708 A | 1/1985 | Spitzer | |
| 4,835,161 A | 5/1989 | Janssens et al. | |
| 4,874,864 A | 10/1989 | Schnur et al. | |
| 5,654,397 A | 8/1997 | Cao et al. | |
| 5,683,999 A | 11/1997 | Jadhav et al. | |

FOREIGN PATENT DOCUMENTS

| | | |
|---|---|---|
| FR | 2 384 757 | 10/1978 |
| JP | 63159861 | 7/1988 |
| JP | 3-31264 | 2/1991 |
| JP | 11302177 | 11/1999 |
| JP | 2001-199968 | 7/2001 |
| WO | WO 93/23409 | 11/1993 |
| WO | WO 94/18212 | 8/1994 |
| WO | WO 97/25316 | 7/1997 |
| WO | WO 99/23091 | 5/1999 |
| WO | WO 00/01676 | 1/2000 |
| WO | WO 00/20358 | 4/2000 |
| WO | WO 00/27819 | 5/2000 |
| WO | WO 00/75310 | 12/2000 |
| WO | WO 00/51641 | 7/2001 |

OTHER PUBLICATIONS

Auron, P., "The Interluekin 1 Receptor: Ligand Interactions and Signal Transduction," Cytokine & Growth Fac. Rev., 1998, vol. 9, No. 3/4, pp. 221-237, GB.
Buscemi et al., "Heterocyclic Photoarrangements. Photochemical Behaviour of Some 3,5-Disubstituted 1,2,4-Oxadiazoles in Methanol at 254 nm," J. of Heterocyclic Chem., 1988, vol. 25, No. 3, pp. 931-935, US.
Cao et al., "IRAK: A Kinase Associated with the Interleukin-1 Receptor," Science, Feb. 23, 1996, vol. 271, pp. 1128-1131, US.
Cao et al., "TRAF is a Signal Transducer for Interleukin-1," Nature, Oct. 3, 1996, vol. 383, pp. 443-446, US.
Dinarello, C., "Interleukin-1," Cytokine & Growth Fac. Rev., 1997, vol. 8, No. 4, pp. 253-265, GB.
Heyer, D., "NPY5 Antagonists for Obesity," Aug. 6, 2001, MedChem Gordon Research Conference 2001, Power Point Presentation Slides.
Kanakaraj et al., "Defective Interleukin (IL)-18-mediated Natural Killer and T Helper Cell Type 1 Responses in IL-1 Receptor-associated Kinase (IRAK)-deficient Mice," J. Exp. Apr. 5, 1999, vol. 189, No. 7, pp. 1129-1138, The Rockefeller Univ. Press, US.
Moffett et al., "Antiulcer Agents. P-Aminobenzamido Aromatic Compounds," J. of Medicinal Chem., 1971, vol. 14, No. 10, pp. 963-968, US.
Muzio et al., "IRAK (Pelle) Family Member IRAK-2 and MyD88 as Proximal Mediators of IL-1 Signaling," Science, Nov. 28, 1997, vol. 278, pp. 1612-1615, US.
O'Neill et al., "Signal Transduction Pathways Activated by the IL-1 Receptor Family: Ancient Signaling Machinery in Mammals, Insects and Plants," J. of Leukocyte Bio., Jun. 1998, vol. 63, pp. 650-657, US.
O'Neill, L., "The Toll/Interleukin-1 Receptor Domain: a Molecular Switch for Inflammation and Hose Defence," Biochemical Society Transactions, 2000, vol. 28, Pt. 5, pp. 557-563, Trinity College, Ireland.
Wesche et al., "IRAK-M is a Novel Member of the Pelle/Interleukin-1 Receptor-associated Kinase (IRAK) Family," J. of Bio. Chem., Jul. 2, 1999, vol. 274, No. 27, pp. 19403-19410, US.
Yang et al., "Signaling Events Induced by Lipopolysaccharide-activated Toll-like Receptor-2," J. of Immunology, 1999, vol. 163, pp. 639-643, US.
Japanese Patent Office, Notification of Reasons for Refusal in Japanese Patent Application No. 2003-533934, Apr. 21, 2009.

*Primary Examiner*—Laura L. Stockton
(74) *Attorney, Agent, or Firm*—Jones Day

(57) ABSTRACT

Compounds, pharmaceutical compositions and methods are provided that are useful in the treatment of inflammatory and immune-related conditions or disorders. In particular, the invention provides compounds which modulate the expression and/or function of proteins involved in inflammation, immune response regulation and cell proliferation. The subject compounds are 2-amino-imidazole derivatives.

1 Claim, 13 Drawing Sheets

21

17

22

23

7a

4

72

BENZIMIDAZOLE DERIVATIVES

CROSS-REFERENCE TO RELATED APPLICATIONS

This application is a continuation of U.S. patent application Ser. No. 10/268,412, filed Oct. 9, 2002, which claims the benefit of U.S. Provisional Application No. 60/327,818, filed Oct. 9, 2001, the disclosure of which is incorporated by reference herein.

BACKGROUND OF THE INVENTION

The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration seen in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra, or IRAP) to relieve inflammatory conditions (for review, see, e.g., Dinarello (1997) *Cytokine Growth Factor Rev.* 8:253-265).

IL-1 treatment of cells induces the formation of a complex consisting of the two IL-1 receptor chains, IL-1R1 and IL-1RAcP, and the resulting heterodimer recruits an adaptor molecule designated as MyD88 (Wesche et al. (1999) *J. Biol. Chem.* 274:19403-19410). MyD88 binds to a protein designated IRAK (IL-1 receptor associated kinase) (see, O'Neill et al. (1998) *J. Leukoc. Biol.* 63(6):650-657, Auron (1998) *Cytokine Growth Factor Rev.* 9(3-4):221-237 and O'Neill (2000) *Biochem. Soc. Trans.* 28(5)557-563, for reviews). IRAK is subsequently phosphorylated and released from the receptor complex to interact with a tumor necrosis factor receptor-associated factor, TRAF6, which transduces the signal to downstream effector molecules (Cao et al. (1996) *Nature* 383:443-446). TRAF6 can trigger the NIK/IKK kinase cascade to activate the transcription factor NF-κB. NF-κB regulates a number of genes that, in turn, regulate immune and inflammatory responses.

Four IRAKs have been identified: IRAK-1 (Cao, et al. (1996) *Science* 271:1128-1131), IRAK-2 (Muzio, et al. (1997) *Science* 278:1612-1615), the monomyeloic cell-specific IRAK-M, also known as IRAK-3 (Wesche, et al. (1999) *J. Biol. Chem.* 274:19403-10) and IRAK-4 (PCT Publication No. WO 01/051641). IRAK proteins have been shown to play a role in transducing signals other than those originating from IL-1 receptors, including signals triggered by activation of IL-18 receptors (Kanakaraj et al. (1999) *J. Exp. Med.* 189(7): 1129-1138) and LPS receptors (Yang et al. (1999) *J. Immunol.* 163:639-643; Wesche et al. (1999) *J. Biol. Chem.* 274: 19403-19410). Overexpression of IRAK-2 and IRAK-M has been shown to be capable of reconstituting the response to IL-1 and LPS in an IRAK deficient cell line.

The identification of compounds that modulate the function of IRAK proteins represents an attractive approach to the development of therapeutic agents for the treatment of inflammatory, cell proliferative and immune-related conditions and diseases associated with IRAK-mediated signal transduction, such as rheumatoid arthritis, inflammatory bowel disease, multiple sclerosis, diabetes, obesity, allergic disease, psoriasis, asthma, graft rejection, cancer and sepsis.

SUMMARY OF THE INVENTION

The present invention is directed to compounds which modulate interleukin-1 (IL-1) receptor-associated kinase (IRAK) and are useful in the prevention or treatment of inflammatory, cell proliferative and immune-related and conditions and diseases. The invention is also directed to pharmaceutical compositions comprising these compounds and the use of the subject compounds and compositions in the prevention or treatment of conditions or diseases mediated by IRAK.

The compounds provided herein have the general formula (I):

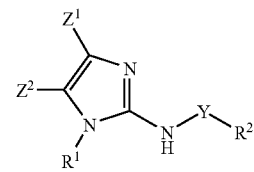

wherein $R^1$ is selected from the group consisting of H, $(C_1-C_8)$alkyl, hetero$(C_1-C_8)$alkyl, fluoro$(C_1-C_4)$alkyl, cycloalkyl$(C_1-C_8)$alkyl, heterocyclo$(C_1-C_8)$alkyl, aryl, aryl$(C_1-C_8)$alkyl, cyclo$(C_3-C_8)$alkyl-$(C_1-C_8)$alkyl, cyclo$(C_3-C_8)$alkylhetero$(C_1-C_8)$alkyl, heterocyclo$(C_1-C_8)$alkyl, arylhetero$(C_1-C_8)$alkyl and heteroaryl;

$R^2$ is $(C_1-C_8)$alkyl, hetero$(C_1-C_8)$alkyl, perfluoro$(C_1-C_4)$alkyl, aryl or heteroaryl;

Y is C(O), S(O)$_m$, S(O)$_2$NR', C(O)NR', $CR^3R^4$, C(NR'), C($=$CR$^3$R$^4$), CR$^3$(OR') or CR$^3$(NR'R''), wherein the subscript m is an integer from 1 to 2;

$Z^1$ and $Z^2$ are independently H, halogen, CN, CO$_2$R', CONR'R'', $(C_1-C_4)$alkyl, $(C_1-C_4)$heteroalkyl, perfluoro$(C_1-C_4)$alkyl, aryl, heteroaryl, NR'R'' or OR'';

alternatively, $Z^1$ and $Z^2$ may be combined to form an additional fused 5-, 6-, 7- or 8-membered cycloalkane, heterocycloalkane, aromatic or heteroaromatic ring;

$R^3$ and $R^4$ are independently selected from the group consisting of H, CN, CO$_2$R', CONR'R'', $(C_1-C_4)$alkyl, $(C_1-C_4)$heteroalkyl, aryl, heteroaryl, NR'R'' and OR';

R' and R'' are independently H, $(C_1-C_4)$alkyl, hetero$(C_1-C_4)$alkyl, aryl or aryl$(C_1-C_4)$alkyl;

alternatively, when R' and R'' are attached to nitrogen, R' and R'' may be combined with the nitrogen atom to form a 5-, 6- or 7-membered ring; and alternatively, when Y is $CR^3R^4$, C(NR'), C($=CR^3R^4$), $CR^3$(OR') or $CR^3$(NR'R''), $R^3$, $R^4$ or R' may be combined with $R^2$ to form a 5-, 6-, 7- or 8-membered ring containing from 0 to 3 heteroatoms selected from the group consisting of O, N, Si and S;

with the proviso that $R^1$ is not 3-(dialkylamino)propyl when Y is C(O) and $Z^1$ and $Z^2$ are combined to form an additional fused benzene ring.

Unless otherwise indicated, the compounds provided in the above formula are meant to include pharmaceutically acceptable salts and prodrugs thereof.

The present invention also provides pharmaceutical compositions comprising a compound of formula I in combination with a pharmaceutically acceptable carrier or excipient.

The present invention further provides methods for treating or preventing inflammatory conditions, cell proliferative disorders or immune-related disorders or comprising administering to a subject in need thereof a therapeutically effective amount of one of the foregoing compounds or compositions.

The present invention also provides methods for treating or preventing a condition or disorder responsive to IRAK modulation, comprising administering to a subject in need thereof a therapeutically effective amount of a compound of formula I.

The present invention also provides methods for treating or preventing a condition or disorder mediated by IRAK comprising administering to a subject in need thereof a therapeutically effective amount of a compound of formula I.

The present invention also provides methods for modulating IRAK comprising contacting a cell with a compound of formula I.

DETAILED DESCRIPTION OF THE INVENTION

Abbreviations and Definitions

Figure 1A:
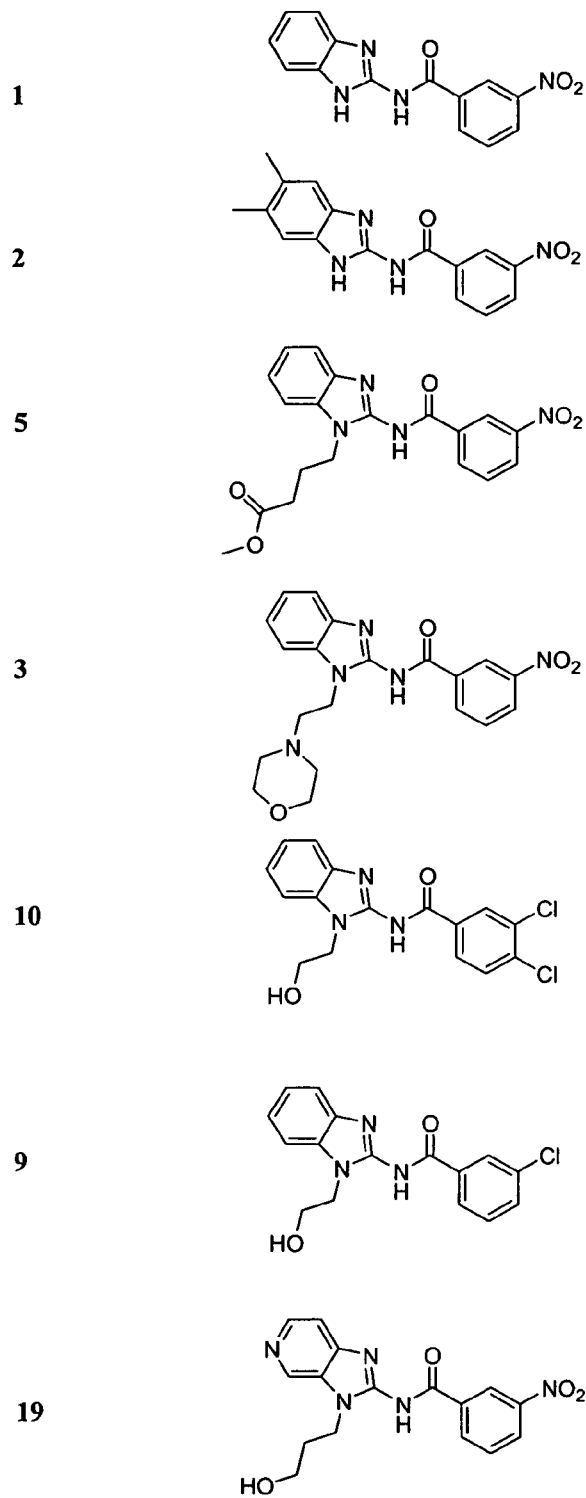
FIGS. 1a to 1e provide exemplary structures of compounds disclosed herein.

The abbreviations used herein are conventional, unless otherwise defined.

As used herein, the term "IRAK" refers to an interleukin-1 (IL-1) receptor-associated kinase protein or variant thereof that is capable of mediating a cellular response to IL-1 in vitro or in vivo. IRAK may be kinase-active or kinase-inactive. Exemplary kinase inactive IRAKs include IRAK-1 and IRAK-4. Exemplary kinase-inactive IRAKs include IRAK-2 and IRAK-3 (also known as IRAK-M). Kinase-active IRAKs may be capable of transphosphorylation of other proteins or autophosphorylation. In preferred embodiments, IRAK is IRAK-1 and/or IRAK-4.

IRAK variants include proteins substantially homologous to native IRAK, i.e., proteins having one or more naturally or non-naturally occurring amino acid deletions, insertions or substitutions (e.g., IRAK derivatives, homologs and fragments). The amino acid sequence of an IRAK variant preferably is at least about 80% identical to a native IRAK, more preferably at least about 90% identical, and most preferably at least about 95% identical.

The terms "signal transduction", "signaling" and related terms refer to a process whereby an extracellular signal (e.g, the concentration of a cytokine, hormone, neurotransmitter, growth factor) is transmitted via a cascade of intracellular protein-protein interactions to the cell nucleus and generates one or more cellular responses (e.g., gene transcription, protein secretion, mitosis, apoptosis). The interaction of an extracellular signaling molecule (e.g, a cytokine, a hormone, a neurotransmitter, a growth factor) with one or more transmembrane protein receptors at the cell surface can activate one or more signal transduction pathways. The protein-protein interactions in a signal transduction pathway may be multivalent and include covalent and/or non-covalent protein modification. An intracellular signaling molecule, i.e., a signal transducing protein or a signal transducer, may be involved in one or more signal transduction pathways. As described herein, protein-protein interactions include direct and indirect interactions.

The terms "treat", "treating" and "treatment" refer to a method of alleviating or abrogating a disease and/or its attendant symptoms.

The terms "prevent", "preventing" and "prevention" refer to a method of barring a subject from acquiring a disease. As used herein, "prevent", "preventing" and "prevention" also include reducing a subject's risk of acquiring a disease.

As used herein, the phrase "IRAK-responsive condition or disorder" and related phrases and terms refer to a condition or disorder that responds favorably to modulation of IRAK activity. Favorable responses to IRAK modulation include alleviation or abrogation of the disease and/or its attendant symptoms, inhibition of the disease, i.e., arrest or reduction of the development of the disease, or its clinical symptoms, and regression of the disease or its clinical symptoms. An IRAK-responsive condition or disease may be completely or partially responsive to IRAK-modulation. An IRAK-responsive condition or disorder may be associated with inappropriate, e.g., less than or greater than normal, IRAK-activity. Inappropriate IRAK functional activity might arise as the result of IRAK expression in cells which normally do not express IRAK, decreased IRAK expression (leading to, e.g., lipid and metabolic disorders and diseases) or increased IRAK expression. An IRAK-responsive condition or disease may include an IRAK-mediated condition or disease, defined below.

As used herein, the phrase "IRAK-mediated condition or disorder" and related phrases and terms refer to a condition or disorder characterized by inappropriate, e.g., less than or greater than normal, IRAK activity. Inappropriate IRAK functional activity might arise as the result of IRAK expression in cells which normally do not express IRAK, increased IRAK expression or degree of intracellular activation (leading to, e.g., inflammatory and autoimmune disorders and diseases) or decreased IRAK expression. An IRAK-mediated condition or disorder may be completely or partially mediated by inappropriate IRAK functional activity. However, an IRAK-mediated condition or disorder is one in which modulation of IRAK results in some effect on the underlying condition or disorder (e.g., an IRAK inhibitor results in some improvement in patient well-being in at least some patients).

As used herein, the phrase "NF-κB-mediated condition or disorder" and related phrases and terms refer to a condition or disorder characterized by inappropriate, e.g., less than or greater than normal, NF-κB activity. Inappropriate NF-κB functional activity might arise as the result of NF-κB expression in cells which normally do not express NF-κB, increased NF-κB expression or degree of intracellular activation (leading to, e.g., inflammatory and autoimmune disorders and diseases) or decreased NF-κB expression. An NF-κB-mediated condition or disorder may be completely or partially mediated by inappropriate NF-κB functional activity. However, an NF-κB-mediated condition or disorder is one in which modulation of NF-κB activation results in some effect on the underlying condition or disorder (e.g., an inhibitor of NF-κB activation results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

The term "modulate" refers to the ability of a compound to increase or decrease the function and/or expression of IRAK, where IRAK function may include kinase activity and/or protein-binding. Modulation may occur in vitro or in vivo. Modulation, as described herein, includes the inhibition or activation of IRAK function and/or the downregulation or upregulation of IRAK expression, either directly or indirectly. A modulator preferably activates IRAK function and/or upregulates IRAK expression. More preferably, a modulator activates or inhibits IRAK function and/or upregulates or downregulates IRAK expression. Most preferably, a modulator inhibits IRAK function and/or downregulates IRAK expression. The ability of a compound to inhibit IRAK function can be demonstrated in an enzymatic assay or a cell-based assay (e.g., inhibition of IL-1-stimulated NF-κB activation).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_8$ means one to eight carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. When a prefix such as ($C_2$-$C_8$) is used to refer to a heteroalkyl group, the number of carbons (2-8, in this example) is meant to include the heteroatoms as well. For example, a $C_2$-heteroalkyl group is meant to include, for example, —$CH_2$OH (one carbon atom and one heteroatom replacing a carbon atom) and —$CH_2$SH. The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Thus, the terms "cycloalkyl" and "heterocycloalkyl" are meant to be included in the terms "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

As used herein, the terms "cyclo($C_3$-$C_8$)alkyl" and "($C_3$-$C_8$)cycloalkyl" refer to a cyclic hydrocarbon radical having three to eight carbon atoms. When a prefix such as ($C_3$-$C_8$) is used to refer to a heterocycloalkyl group, e.g., "heterocyclo ($C_3$-$C_8$)alkyl" or "hetero($C_3$-$C_8$)cycloalkyl", the number of carbons (three to eight, in this example) is meant to include the heteroatoms as well.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like), including those alkyl groups in which the alkyl group is a heteroalkyl group.

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted (C$_1$-C$_8$)alkyl and heteroalkyl, unsubstituted aryl, aryl substituted with 1-3 halogens, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0-3 substituents, more preferably 0, 1, or 2 substituents, unless otherwise specified.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and the subscript q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and the subscript r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where the subscripts s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) *J. Pharm. Sci.* 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

The present invention is directed to compounds, compositions and methods useful in the modulation of IRAK. Accordingly, the compounds of the present invention are compounds which inhibit at least one function or characteristic of a mammalian IRAK polypeptide, for example, a human IRAK polypeptide.

The full-length human IRAK-1 protein (GenBank Accession No. L76191) has been described, see, e.g, Cao et al. (1996) Science 271(5252):1128-1131, IRAK-1 is an active protein kinase and is capable of autophosphorylation in vitro. However, it has been shown that the enzymatic activity is not required for an IRAK-mediated cellular response to IL-1, e.g., IL-1-stimulated NF-κB activation. IRAK-4 (GenBank Accession No. AX196260) is described in PCT Publication No. WO 01/051641.

IRAK Modulators

The present invention provides compounds having antiinflammatory and anti-immunoregulatory activity. It is believed that the compounds of the invention will interfere with inappropriate IL-1 induced signal transduction by specifically modulating or inhibiting IRAK function, e.g., IRAK-1 and/or IRAK-4 function. IRAK is an intracellular component of the signaling pathway that is activated by the binding of IL-1 to the IL-1 receptor (IL-1R). In particular, IRAK associates with the active receptor complex and transduces the IL-1 signal by interacting with one or more intracellular signaling molecules. Cellular responses to IRAK-mediated signal transduction include increased transcription of genes that regulate inflammatory and immune responses, e.g., NF-kB. Therefore, inhibition of IRAK function, e.g., inhibition of IRAK kinase activity, will inhibit an IRAK-mediated cellular response and treat or prevent an IRAK-mediated condition or disorder.

While a precise understanding of the mechanism by which compounds of the present invention inhibit an IRAK-mediated response is not required in order to practice the present invention, it is believed that the compounds interfere with the phosphorylation by IRAK of one or more intracellular proteins, including IRAK itself. Compounds contemplated by the invention include, but are not limited to, the exemplary compounds provided herein.

The compounds provided herein have the general formula (I):

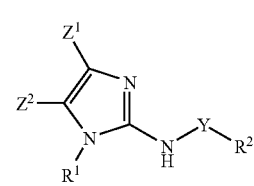

In formula I, $R^1$ is H, $(C_1-C_8)$alkyl, hetero$(C_1-C_8)$alkyl, fluoro$(C_1-C_4)$alkyl, cycloalkyl$(C_1-C_8)$alkyl, heterocyclo$(C_1-C_8)$alkyl, aryl, aryl$(C_1-C_8)$alkyl, arylhetero$(C_1-C_8)$alkyl or heteroaryl. Exemplary $R^1$ groups are H, ethyl, (3-carboxymethyl)propyl, (2-morpholin-4-yl)ethyl, 1-hydroxyethyl, 1-hydroxypropyl, (carboxyethyl)methyl, 1-hydroxy-n-butyl, (3-hydroxymethyl)phenyl, 2-(2-hydroxymethyl-1-propyl)ethyl,

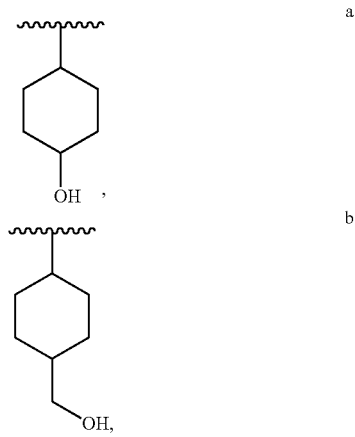

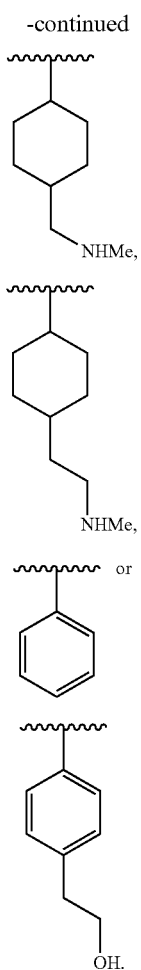

It is to be understood that when $R^1$ contains one or more asymmetric carbon atoms, $R^1$ includes individual stereoisomers as well as mixtures. For example, when $R^1$ is a, b, c or d and the like, the 1,4-cis and trans isomers and racemates thereof are intended to be within the scope of the invention.

$R^2$ is $(C_1-C_8)$alkyl, hetero$(C_1-C_8)$alkyl, perfluoro$(C_1-C_4)$alkyl, aryl or heteroaryl. Exemplary $R^2$ groups are 3-chorophenyl, 3,4-dichlorophenyl, 3-methanesulfonyl, 3-cyanophenyl, 3-carboxymethylphenyl, 4-methoxyphenyl, 3-methylsulfamoylphenyl, 3-biphenyl, (2-fluoro)ethylsulfamoylphenyl, (2-methoxy)ethylsulfamoylphenyl, (2-hydroxy-2-methyl)ethylsulfamoylphenyl, 3-trifluoromethylphenyl, 3-tetrazolylphenyl, 3-triazolylphenyl, 3-nitrophenyl, (3-nitro-4-hydroxymethyl)phenyl, thiophen-2-yl and furan-2-yl.

Y is $C(O)$, $S(O)_m$, $S(O)_2NR'$, $C(O)NR'$, $CR^3R^4$, $C(NR')$, $C(=CR^3R^4)$, $CR^3(OR')$ or $CR^3(NR'R'')$, wherein the subscript m is an integer from 1 to 2. Exemplary Y groups are $C(O)$, $SO_2$, $C(O)NH$ and $CH_2$.

$Z^1$ and $Z^2$ are independently H, halogen, CN, $CO_2R'$, $CONR'R''$, $(C_1-C_4)$alkyl, $(C_1-C_4)$heteroalkyl, perfluoro$(C_1-C_4)$alkyl, aryl, heteroaryl, $NR'R''$ or $OR'$. Alternatively, $Z^1$ and $Z^2$ may be combined to form an additional fused 5-, 6-, 7- or 8-membered cycloalkane, heterocycloalkane, aromatic or heteroaromatic ring. Exemplary combinations of $Z^1$ and $Z^2$ are $Z^1$ and $Z^2$ combined to form an additional fused benzene, cyclohexane, pyridine or tetrahydropyran ring.

$R^3$ and $R^4$ are independently H, CN, $CO_2R'$, $CONR'R''$, $(C_1-C_4)$alkyl, $(C_1-C_4)$heteroalkyl, aryl, heteroaryl, $NR'R''$ or $OR'$.

$R'$ and $R''$ are independently H, $(C_1-C_4)$alkyl, hetero$(C_1-C_4)$alkyl, aryl or aryl$(C_1-C_4)$alkyl. Alternatively, when $R'$ and $R''$ are attached to nitrogen, $R'$ and $R''$ may be combined with the nitrogen atom to form a 5-, 6- or 7-membered ring.

Alternatively, when Y is $CR^3R^4$, $C(NR')$, $C(=CR^3R^4)$, $CR^3(OR')$ or $CR^3(NR'R'')$, $R^3$, $R^4$ or $R'$ may be combined with $R^2$ to form a 5-, 6-, 7- or 8-membered ring containing from 0 to 3 heteroatoms selected from the group consisting of O, N, Si and S.

It is to be understood that compounds of formula I do not include compounds wherein $R^1$ is 3-(dialkylamino)propyl when Y is $C(O)$ and $Z^1$ and $Z^2$ are combined to form an additional fused benzene ring.

Also provided herein are compounds of formula I, wherein $R^1$ is H, unsubstituted $(C_1-C_8)$alkyl, $(C_1-C_8)$alkyl substituted with OR', OC(O)R', $CO_2R'$, CONR'R'', OC(O)NR'R'', NR''C(O)R', NR''$CO_2R'$, hydroxy$(C_1-C_8)$alkyl or amino$(C_1-C_8)$alkyl, hetero$(C_1-C_8)$alkyl, fluoro$(C_1-C_4)$alkyl, cycloalkyl$(C_1-C_8)$alkyl, heterocyclo$(C_1-C_8)$alkyl, aryl, aryl$(C_1-C_8)$alkyl, arylhetero$(C_1-C_8)$alkyl or heteroaryl.

Within these embodiments are several groups of preferred embodiments, described below.

In one group of preferred embodiments, $R^1$ is H, $(C_1-C_8)$alkyl, $(C_1-C_8)$heteroalkyl or aryl.

In a preferred embodiment, $R^1$ is substituted $(C_1-C_8)$alkyl. Particularly preferred substituents are OR', NR'R'', OC(O)R', $CO_2R'$, CONR'R'', OC(O)NR'R'', NR''C(O)R', NR''$CO_2R'$, hydroxy$(C_1-C_8)$alkyl and amino$(C_1-C_8)$alkyl. In a particularly preferred embodiment, $R^1$ is $(C_1-C_8)$alkyl substituted with OH, hydroxy$(C_1-C_4)$alkyl or amino$(C_1-C_4)$alkyl.

In another preferred embodiment, $R^1$ is cyclo$(C_1-C_8)$alkyl. In a particularly preferred embodiment, $R^1$ is cyclohexyl.

In another preferred embodiment, $R^1$ is heterocyclo$(C_1-C_8)$alkyl. In a particularly preferred embodiment, $R^1$ is tetrahydropyranyl.

In another preferred embodiment, $R^1$ is phenyl.

In another preferred embodiment, $R^1$ is substituted phenyl. Particularly preferred substituents are OR', NR'R'', OC(O)R', $CO_2R'$, CONR'R'', OC(O)NR'R'', NR''C(O)R', NR''$CO_2R'$, hydroxy$(C_1-C_8)$alkyl and amino$(C_1-C_8)$alkyl. In a particularly preferred embodiment, $R^1$ is phenyl substituted with hydroxy$(C_1-C_4)$alkyl.

In another group of preferred embodiments, $R^1$ is

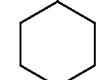

-continued

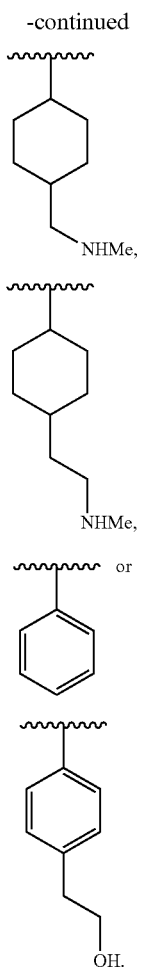

In another group of preferred embodiments, $Z^1$ and $Z^2$ are combined to form an additional fused 6-membered cycloalkane or heterocycloalkane, aromatic or heteroaromatic ring.

In one preferred embodiment, $Z^1$ and $Z^2$ are combined to form an additional fused benzene ring. In another preferred embodiment, $Z^1$ and $Z^2$ are combined to form an additional fused pyridine ring. In another preferred embodiment, $Z^1$ and $Z^2$ are combined to form an additional fused cyclohexane ring. In still another preferred embodiment, $Z^1$ and $Z^2$ are combined to form an additional fused tetrahydropyran ring.

One group of preferred embodiments is represented by the formula (II):

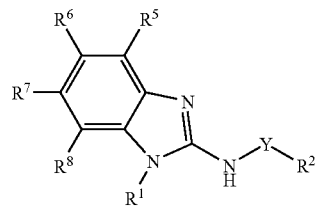

II

In formula II, D, E, F and G are independently CR''' or N, each R''' is independently H, halogen, (C$_1$-C$_4$)alkyl, perfluoro(C$_1$-C$_4$)alkyl, (C$_1$-C$_4$)heteroalkyl, aryl, aryl(C$_1$-C$_4$)alkyl, heteroaryl, CN, CO$_2$R', CONR'R'', NR'R'', NO$_2$, OR', SR', C(O)R', OC(O)R', N(R'')C(O)R', N(R'')CO$_2$R', N(R'')C(O) NR'R'', S(O)$_m$NR'R'', S(O)$_m$R' or N(R'')S(O)$_m$R', and the subscript m is an integer from 1 to 2. It is to be understood that D, E, F and G are combined to form a stable, fully conjugated moiety —D—E—F—G—. For example, compounds wherein —D—E—F—G— is —N—N—N—N— and the like are not intended to be within the scope of the invention. Alternatively, R''' may be combined with R$^1$ to form an additional 5-, 6-, 7- or 8-membered ring or an adjacent R''' to form an additional fused 5-, 6-, 7- or 8-membered ring. Y, R$^1$, R$^2$, R' and R'' have the meanings provided above.

A preferred embodiment is represented by the formula (IIa):

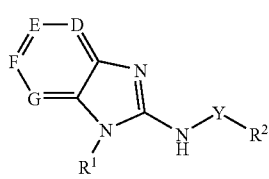

IIa wherein R$^5$, R$^6$, R$^7$ and R$^8$ are independently H, halogen, (C$_1$-C$_4$)alkyl, perfluoro(C$_1$-C$_4$)alkyl, (C$_1$-C$_4$)heteroalkyl, aryl, aryl(C$_1$-C$_4$)alkyl, heteroaryl, CN, CO$_2$R', CONR'R'', NR'R'', NO$_2$, OR', SR', C(O)R', OC(O)R', N(R'')C(O)R', N(R'')CO$_2$R', N(R'')C(O)NR'R'', S(O)$_m$NR'R'', S(O)$_m$R' or N(R'')S(O)$_m$R' and the subscript m is an integer from 1 to 2. Alternatively, R$^5$, R$^6$ or R$^7$ may be combined with an adjacent R group selected from the group consisting of R$^5$, R$^6$, R$^7$ and R$^8$ to form an additional fused 5-, 6-, 7- or 8-membered ring and R$^8$ may be combined with R$^7$ to form an additional fused 5-, 6-, 7- or 8-membered ring or R$^1$ to form an additional 5-, 6-, 7- or 8-membered ring. Y, R$^1$, R$^2$, R' and R'' have the meanings provided above.

In one particularly preferred embodiment, R$^6$ and R$^7$ are independently H, halogen, (C$_1$-C$_4$)alkyl, CO$_2$R', NR'R'', OR', OC(O)R', N(R'')C(O)R' or N(R'')C(O)NR'R''.

In another particularly preferred embodiment, R$^6$ is H, fluorine, methyl, hydroxymethyl, (dimethylamino)methyl, (methylamino)methyl, amino, carbomethoxy, methoxy,

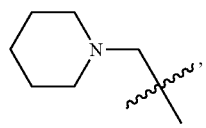

g

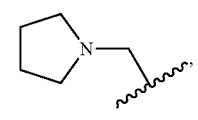

h

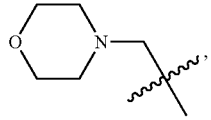

i

-continued

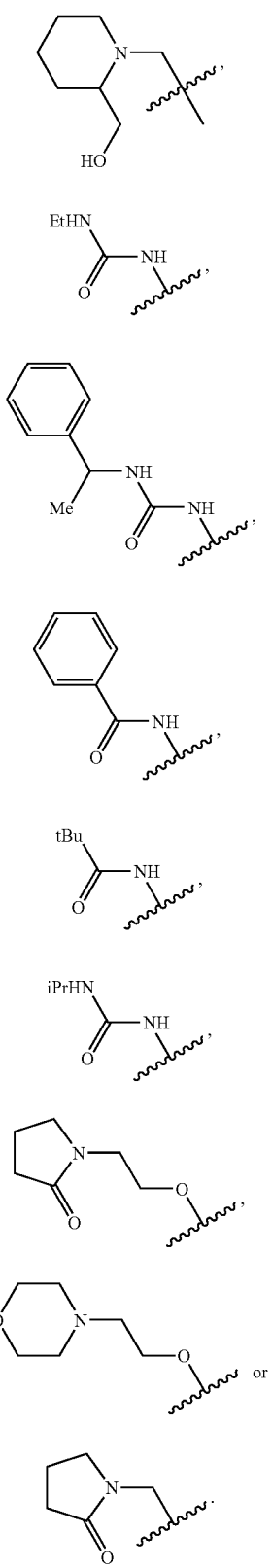

In another particularly preferred embodiment, $R^7$ is H, fluorine, methyl, hydroxymethyl,

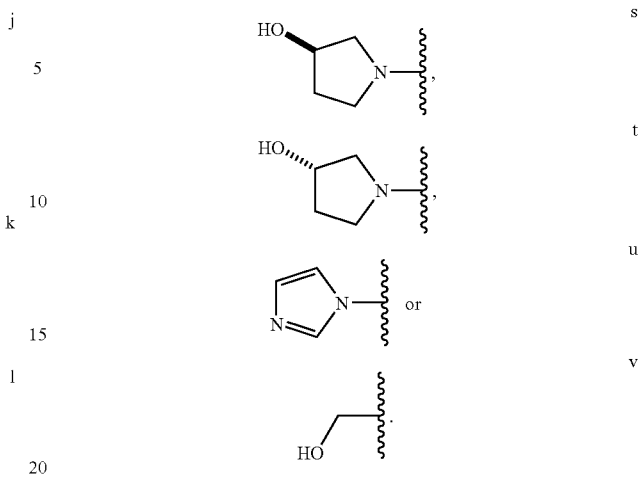

In another particularly preferred embodiment, $R^8$ is H or OH.

Another preferred embodiment is represented by the formula (IIb):

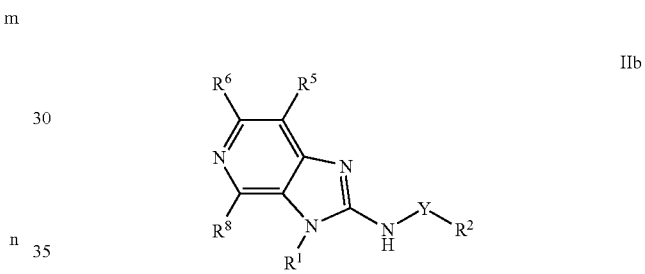

wherein $R^5$, $R^6$ and $R^8$ are independently H, halogen, $(C_1\text{-}C_4)$ alkyl, perfluoro$(C_1\text{-}C_4)$alkyl, $(C_1\text{-}C_4)$heteroalkyl, aryl, aryl $(C_1\text{-}C_4)$alkyl, heteroaryl, CN, $CO_2R'$, CONR'R", NR'R", $NO_2$, OR', SR', C(O)R', OC(O)R', N(R")C(O)R', N(R") $CO_2R'$, N(R")C(O)NR'R", $S(O)_m NR'R"$, $S(O)_m R'$ or N(R")S $(O)_m R'$, and the subscript m is an integer from 1 to 2. Alternatively, $R^6$ may be combined with $R^5$ to form an additional fused 5-, 6-, 7- or 8-membered ring and $R^8$ may be combined with $R^1$ to form an additional 5-, 6-, 7- or 8-membered ring.

Another preferred embodiment is represented by the formula (IIc):

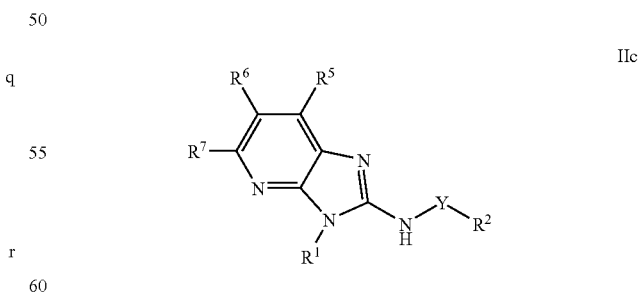

wherein $R^5$, $R^6$ and $R^7$ are independently H, halogen, $(C_1\text{-}C_4)$ alkyl, perfluoro$(C_1\text{-}C_4)$alkyl, $(C_1\text{-}C_4)$heteroalkyl, aryl, aryl $(C_1\text{-}C_4)$alkyl, heteroaryl, CN, $CO_2R'$, CONR'R", NR'R", $NO_2$, OR', SR', C(O)R', OC(O)R', N(R")C(O)R', N(R") $CO_2R'$, N(R")C(O)NR'R", $S(O)_m NR'R"$, $S(O)_m R$ or N(R")S $(O)_m R'$ and the subscript m is an integer from 1 to 2. Alternatively, $R^6$ may be combined with $R^5$ or $R^7$ to form an additional fused 5-, 6-, 7- or 8-membered ring.

Another group of preferred embodiments is represented by the formula (III):

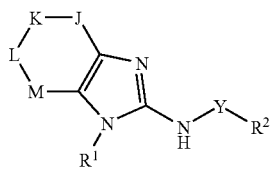

III

In formula III, J, K, L and M are independently $CR^aR^b$, $NR^a$ or O and $R^a$ and $R^b$ are independently H, halogen, CN, $CO_2R'$, CONR'R", $(C_1-C_4)$alkyl, $(C_1-C_4)$heteroalkyl, aryl, heteroaryl, NR'R" or OR'. It is to be understood that J, K, L and M are combined to form a stable moiety —J—K—L—M—. For example, compounds wherein —J—K—L—M— is —O—O—L—M— (J and K are O) or —J—O—O—M— (K and L are O) or —J—K—O—O— (L and M are O) and the like are not intended to be within the scope of the invention. Alternatively, J, K or L may be combined with an adjacent R group selected from $R^a$ and $R^b$ to form an additional fused 5-, 6-, 7- or 8-membered ring and M may be combined with an adjacent R group selected from $R^a$ and $R^b$ to form an additional fused 5-, 6-, 7- or 8-membered ring or $R^1$ to form an additional 5-, 6-, 7- or 8-membered ring.

In another group of preferred embodiments, Y is C(O), C(O)NR', $S(O)_m$ or $CR^3R^4$. In a preferred embodiment, Y is C(O). In another preferred embodiment, Y is C(O)NR'. In a particularly preferred embodiment, Y is C(O)NH.

In another preferred embodiment, Y is $S(O)_m$, wherein the subscript m is an integer selected from 1 to 2. In a particularly preferred embodiment, Y is $SO_2$.

In another preferred embodiment, Y is $CR^3R^4$. In a particularly preferred embodiment, Y is $CH_2$.

In another group of preferred embodiments, $R^2$ is aryl or heteroaryl. In one preferred embodiment, $R^2$ is thiophenyl or furyl.

In another preferred embodiment, $R^2$ is phenyl. In a particularly preferred embodiment, $R^2$ is phenyl substituted with at least one substituent selected from halogen, $(C_1-C_4)$alkyl, perfluoro$(C_1-C_4)$alkyl, $(C_1-C_4)$heteroalkyl, aryl, aryl$(C_1-C_4)$alkyl, heteroaryl, CN, $CO_2R'$, CONR'R", NR'R", $NO_2$, OR', SR', C(O)R', N(R")C(O)R', N(R")$CO_2R'$, N(R")C(O)NR'R", $S(O)_m$NR'R", $S(O)_mR'$ and N(R")$S(O)_mR'$ and the subscript m is an integer from 1 to 2. Further preferred are those embodiments in which $R^2$ is phenyl substituted with at least one substituent selected from perfluoro$(C_1-C_4)$alkyl, aryl, heteroaryl, CONR'R", $NO_2$, $S(O)_m$NR'R" and $S(O)_mR'$. Still further preferred are those embodiments in which $R^2$ is phenyl substituted with at least one substituent selected from $CF_3$, $CF_2R'$, phenyl, tetrazolyl, triazolyl, CONHR', $NO_2$, $SO_2$NHR' and $SO_2R'$.

Also particularly preferred are those embodiments that combine two or more of these preferred groups. Accordingly, in one group of particularly preferred embodiments, $Z^1$ and $Z^2$ are combined to form an additional fused aromatic or heteroaromatic ring and Y is C(O), C(O)NR', $S(O)_m$ or $CR^3R^4$.

In another group of particularly preferred embodiments, $Z^1$ and $Z^2$ are combined to form an additional fused benzene ring and Y is C(O), C(O)NR', $S(O)_m$ or $CR^3R^4$.

Another group of particularly preferred embodiments is represented by the formula (IV):

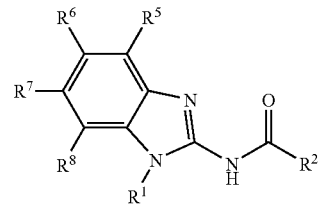

IV wherein $R^1$, $R^2$, $R^5$, $R^6$, $R^7$ and $R^8$ have the meanings and preferred groupings provided above.

Another group of particularly preferred embodiments is represented by the formula (V):

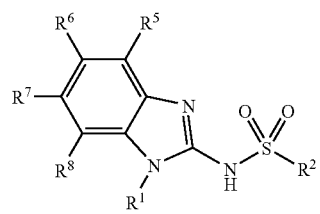

V wherein $R^1$, $R^2$, $R^5$, $R^6$, $R^7$ and $R^8$ have the meanings and preferred groupings provided above.

Another group of particularly preferred embodiments is represented by the formula (VI):

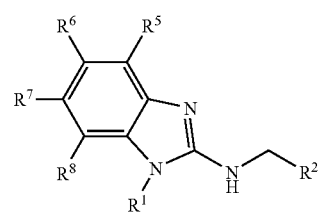

VI wherein $R^1$, $R^2$, $R^5$, $R^6$, $R^7$ and $R^8$ have the meanings and preferred groupings provided above.

In another group of particularly preferred embodiments, $Z^1$ and $Z^2$ are combined to form an additional fused pyridine ring and Y is C(O).

In another group of particularly preferred embodiments, $Z^1$ and $Z^2$ are combined to form an additional fused aromatic or heteroaromatic ring and $R^1$ is H, $(C_1-C_8)$alkyl, $(C_1-C_8)$heteroalkyl or aryl. In one particularly preferred embodiment, $Z^1$ and $Z^2$ are combined to form an additional fused aromatic or heteroaromatic ring and $R^1$ is substituted $(C_1-C_8)$alkyl. In another particularly preferred embodiment, $Z^1$ and $Z^2$ are combined to form an additional fused aromatic or heteroaromatic ring and $R^1$ is cyclo$(C_1-C_8)$alkyl. In another particularly preferred embodiment, $Z^1$ and $Z^2$ are combined to form an additional fused aromatic or heteroaromatic ring and $R^1$ is heterocyclo$(C_1-C_8)$alkyl. In another particularly preferred embodiment, $Z^1$ and $Z^2$ are combined to form an additional fused aromatic or heteroaromatic ring and $R^1$ is phenyl. In another particularly preferred embodiment, $Z^1$ and $Z^2$ are combined to form an additional fused aromatic or heteroaromatic ring and $R^1$ is substituted phenyl.

In another group of particularly preferred embodiments, $Z^1$ and $Z^2$ are combined to form an additional fused aromatic or heteroaromatic ring and $R^2$ is aryl.

In another group of particularly preferred embodiments, $R^1$ is H, $(C_1-C_8)$alkyl, $(C_1-C_8)$heteroalkyl or aryl and Y is C(O) or C(O)NH. In one particularly preferred embodiment, $R^1$ is substituted $(C_1-C_8)$alkyl and Y is C(O) or C(O)NH. In another particularly preferred embodiment, $R^1$ is cyclo($C_3$-$C_8$)alkyl and Y is C(O) or C(O)NH. In another particularly preferred embodiment, $R^1$ is heterocyclo($C_3$-$C_8$)alkyl and Y is C(O) or C(O)NH. In another particularly preferred embodiment, $R^1$ is phenyl and Y is C(O) or C(O)NH. In another particularly preferred embodiment, $R^1$ is substituted phenyl and Y is C(O) or C(O)NH.

In another group of particularly preferred embodiments, $R^1$ is H, $(C_1-C_8)$alkyl, $(C_1-C_8)$heteroalkyl or aryl and $R^2$ is aryl. In one particularly preferred embodiment, $R^1$ is substituted $(C_1-C_8)$alkyl and $R^2$ is aryl. In another particularly preferred embodiment, $R^1$ is cyclo($C_3$-$C_8$)alkyl and $R^2$ is aryl. In another particularly preferred embodiment, $R^1$ is heterocyclo($C_3$-$C_8$)alkyl and $R^2$ is aryl. In another particularly preferred embodiment, $R^1$ is phenyl and $R^2$ is aryl. In another particularly preferred embodiment, $R^1$ is substituted phenyl and $R^2$ is aryl.

In another group of particularly preferred embodiments, Y is C(O) or C(O)NH and $R^2$ is aryl.

In another group of particularly preferred embodiments, $Z^1$ and $Z^2$ are combined to form an additional fused aromatic or heteroaromatic ring, Y is C(O) or C(O)NR' and $R^2$ is aryl.

Still another group of particularly preferred embodiments is represented by the formula (VII):

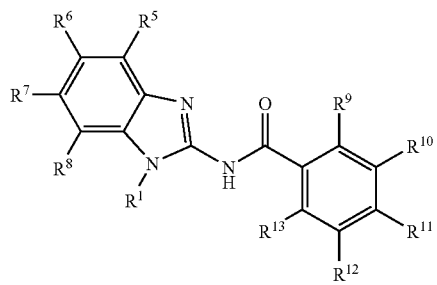

VII wherein $R^9$, $R^{10}$, $R^{11}$, $R^{12}$ and $R^{13}$ are independently H, halogen, $(C_1-C_4)$alkyl, perfluoro$(C_1-C_4)$alkyl, hetero$(C_1-C_4)$alkyl, aryl, aryl$(C_1-C_4)$alkyl, heteroaryl, CN, $CO_2R'$, CONR'R'', NR'R'', $NO_2$, OR', SR', C(O)R', N(R'')C(O)R', N(R'')$CO_2$R', N(R'')C(O)NR'R'', $S(O)_m$NR'R'', $S(O)_m$R' or N(R'')S(O)$_m$R' and the subscript m is an integer from 1 to 2. Alternatively, $R^9$, $R^{10}$, $R^{11}$, $R^{12}$ or $R^{13}$ may be combined with an adjacent R group selected from the group consisting of $R^9$, $R^{10}$, $R^{11}$, $R^{12}$ and $R^{13}$ to form an additional fused 5-, 6-, 7- or 8-membered ring. $R^1$, $R^5$, $R^6$, $R^7$, $R^8$, R' and R'' have the meanings and preferred groupings provided above.

In one particularly preferred embodiment, at least one of $R^9$, $R^{10}$, $R^{11}$, $R^{12}$ and $R^{13}$ is selected from halogen, $(C_1-C_4)$alkyl, perfluoro$(C_1-C_4)$alkyl, $(C_1-C_4)$heteroalkyl, aryl, aryl$(C_1-C_4)$alkyl, heteroaryl, CN, $CO_2R'$, CONR'R'', NR'R'', $NO_2$, OR', SR', C(O)R', N(R'')C(O)R', N(R'')$CO_2$R', N(R'')C(O)NR'R'', $S(O)_m$NR'R'', $S(O)_m$R' and N(R'')S(O)$_m$R'. In a further preferred embodiment, at least one of $R^9$, $R^{10}$, $R^{11}$, $R^{12}$ and $R^{13}$ is selected from perfluoro$(C_1-C_4)$alkyl, aryl, heteroaryl, CONR'R'', $NO_2$, $S(O)_m$NR'R'' and $S(O)_m$R'. In a still further preferred embodiment, at least one of $R^9$, $R^{10}$, $R^{11}$, $R^{12}$ and $R^{13}$ is selected from $CF_3$, $CF_2R'$, phenyl, tetrazolyl, triazolyl, CONHR', $NO_2$, $SO_2$NHR' and $SO_2$R'.

In one particularly preferred embodiment, $R^{10}$ is $NO_2$. A further preferred embodiment is represented by the formula (VIIc):

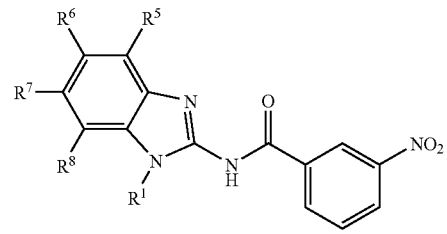

VIIc

In another particularly preferred embodiment, $R^{10}$ is $CF_3$. A further preferred embodiment is represented by the formula:

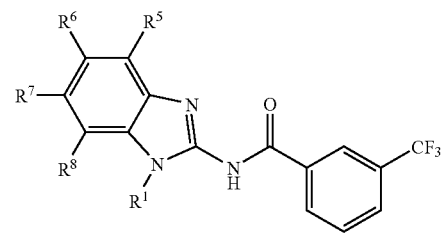

VIId

In another particularly preferred embodiment, $R^{10}$ is $S(O)_m$NR'R'' or $S(O)_m$R'. In a further preferred embodiment, $R^{10}$ is

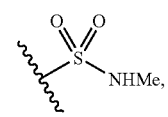

w

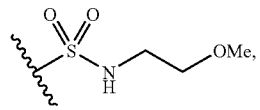

x

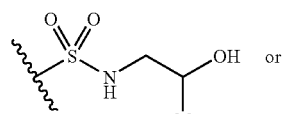

y

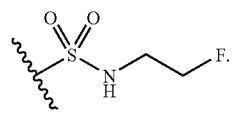

z

In another group of particularly preferred embodiments, $Z^1$ and $Z^2$ are combined to form an additional fused aromatic or heteroaromatic ring, Y is C(O) or C(O)NR' and R' is H, $(C_1-C_8)$alkyl, $(C_1-C_8)$heteroalkyl or aryl. In one particularly preferred embodiment, $Z^1$ and $Z^2$ are combined to form an additional fused aromatic or heteroaromatic ring, Y is C(O) or C(O)NR' and R1 is substituted (C1-C8)alkyl. In another particularly preferred embodiment, $Z^1$ and $Z^2$ are combined to form an additional fused aromatic or heteroaromatic ring, Y is C(O) or C(O)NR' and R1 is cyclo(C1-C8)alkyl. In another particularly preferred embodiment, $Z^1$ and $Z^2$ are combined to form an additional fused aromatic or heteroaromatic ring, Y is C(O) or C(O)NR' and R1 is heterocyclo(C1-C8)alkyl. In another particularly preferred embodiment, $Z^1$ and $Z^2$ are combined to form an additional fused aromatic or heteroaromatic ring, Y is C(O) or C(O)NR' and R1 is phenyl. In another particularly preferred embodiment, $Z^1$ and $Z^2$ are combined to form an additional fused aromatic or heteroaromatic ring, Y is C(O) or C(O)NR' and R1 is substituted phenyl.

In another group of particularly preferred embodiments, $Z^1$ and $Z^2$ are combined to form an additional fused aromatic or heteroaromatic ring, $R^1$ is H, $(C_1-C_8)$alkyl, $(C_1-C_8)$heteroalkyl or aryl and $R^2$ is aryl. In one particularly preferred embodiment, $Z^1$ and $Z^2$ are combined to form an additional fused aromatic or heteroaromatic ring, $R^1$ is substituted $(C_1-C_8)$alkyl and $R^2$ is aryl. In another particularly preferred embodiment, $Z^1$ and $Z^2$ are combined to form an additional fused aromatic or heteroaromatic ring, $R^1$ is cyclo$(C_3-C_8)$ alkyl and $R^2$ is aryl. In another particularly preferred embodiment, $Z^1$ and $Z^2$ are combined to form an additional fused aromatic or heteroaromatic ring, $R^1$ is heterocyclo$(C_3-C_8)$ alkyl and $R^2$ is aryl. In another particularly preferred embodiment, $Z^1$ and $Z^2$ are combined to form an additional fused aromatic or heteroaromatic ring, $R^1$ is phenyl and $R^2$ is aryl. In another particularly preferred embodiment, $Z^1$ and $Z^2$ are combined to form an additional fused aromatic or heteroaromatic ring, $R^1$ is substituted phenyl and $R^2$ is aryl.

In another group of particularly preferred embodiments, Y is C(O) or C(O)NR', $R^1$ is H, $(C_1-C_8)$alkyl, $(C_1-C_8)$heteroalkyl or aryl and $R^2$ is aryl. In one particularly preferred embodiment, Y is C(O) or C(O)NR', $R^1$ is substituted $(C_1-C_8)$ alkyl and $R^2$ is aryl. In another particularly preferred embodiment, Y is C(O) or C(O)NR', $R^1$ is cyclo$(C_3-C_8)$alkyl and $R^2$ is aryl. In another particularly preferred embodiment, Y is C(O) or C(O)NR', $R^1$ is heterocyclo$(C_3-C_8)$alkyl and $R^2$ is aryl. In another particularly preferred embodiment, Y is C(O) or C(O)NR', $R^1$ is phenyl and $R^2$ is aryl. In another particularly preferred embodiment, Y is C(O) or C(O)NR', $R^1$ is substituted phenyl and $R^2$ is aryl.

In another group of particularly preferred embodiments, $Z^1$ and $Z^2$ are combined to form an additional fused aromatic or heteroaromatic ring, $R^1$ is H, $(C_1-C_8)$alkyl, $(C_1-C_8)$heteroalkyl or aryl, $R^2$ is aryl and Y is C(O) or C(O)NR'. In one particularly preferred embodiment, $Z^1$ and $Z^2$ are combined to form an additional fused aromatic or heteroaromatic ring, $R^1$ is substituted (C1-C8)alkyl, $R^2$ is aryl and Y is C(O) or C(O)NR'. In another particularly preferred embodiment, $Z^1$ and $Z^2$ are combined to form an additional fused aromatic or heteroaromatic ring, R1 is cyclo(C1-C8)alkyl, $R^2$ is aryl and Y is C(O) or C(O)NR'. In another particularly preferred embodiment, $Z^1$ and $Z^2$ are combined to form an additional fused aromatic or heteroaromatic ring, R1 is heterocyclo(C1-C8)alkyl, $R^2$ is aryl and Y is C(O) or C(O)NR'. In another particularly preferred embodiment, $Z^1$ and $Z^2$ are combined to form an additional fused aromatic or heteroaromatic ring, R1 is phenyl, $R^2$ is aryl and Y is C(O) or C(O)NR'. In another particularly preferred embodiment, $Z^1$ and $Z^2$ are combined to form an additional fused aromatic or heteroaromatic ring, R1 is substituted phenyl, $R^2$ is aryl and Y is C(O) or C(O)NR'.

Another group of particularly preferred embodiments is represented by the formula (VIIa):

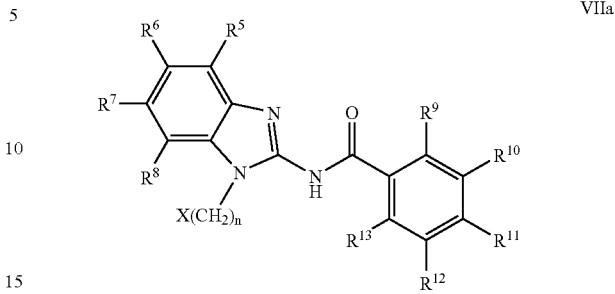

VIIa wherein the subscript n is an integer from 1 to 5, X is H, OR', NR'R", OC(O)R', $CO_2R'$, CONR'R", OC(O)NR'R", NR"C(O)R' or NR"$CO_2$R' and $R^5$, $R^6$, $R^7$, $R^8$, $R^9$, $R^{10}$, $R^{11}$, $R^{12}$ and $R^{13}$ have the meanings and preferred groupings provided above. In one particularly preferred embodiment, X is OH.

Another group of particularly preferred embodiments is represented by the formula (VIIb):

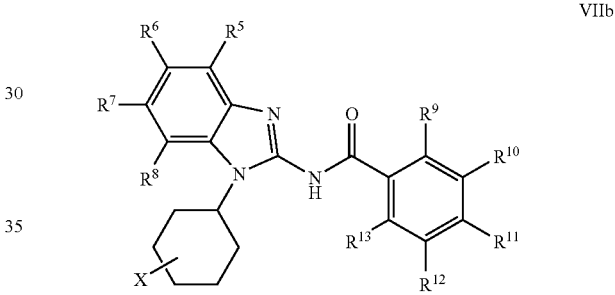

VIIb wherein X, $R^5$, $R^6$, $R^7$, $R^8$, $R^9$, $R^{10}$, $R^{11}$, $R^{12}$ and $R^{13}$ have the meanings and preferred groupings provided above. In one particularly preferred embodiment, X is H, OH, hydroxy($C_1$-$C_4$)alkyl or amino($C_1$-$C_4$)alkyl.

Figure 1B:
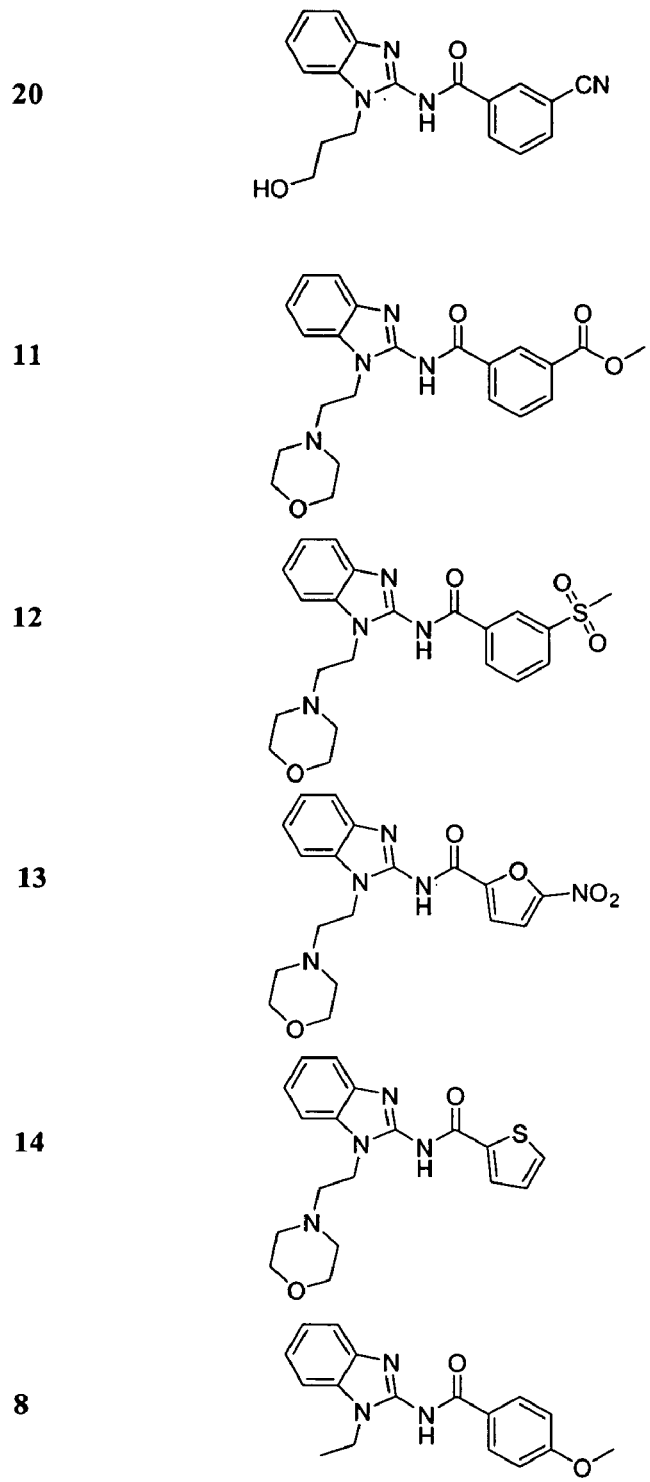
Figure 1C:
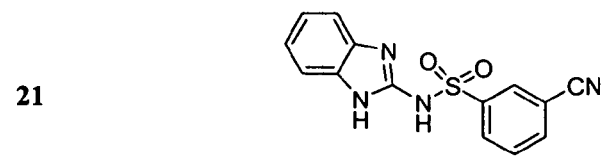
Figure 1C:
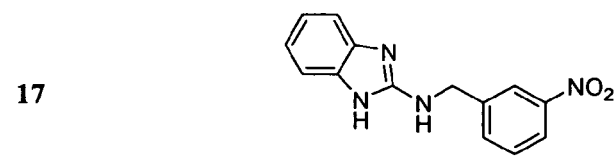
Figure 1C:
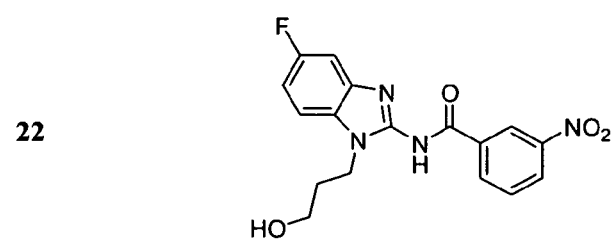
Figure 1C:
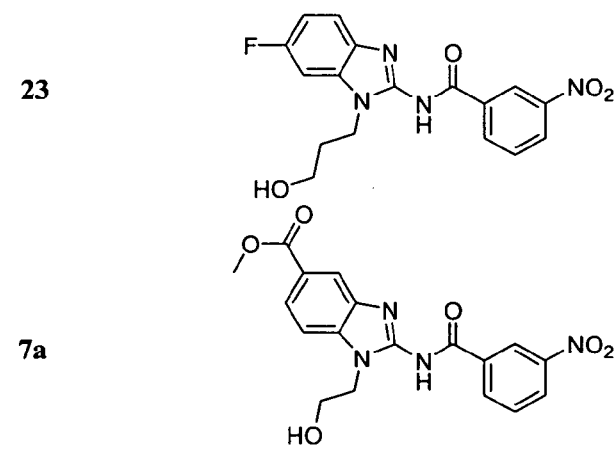
Figure 1D:
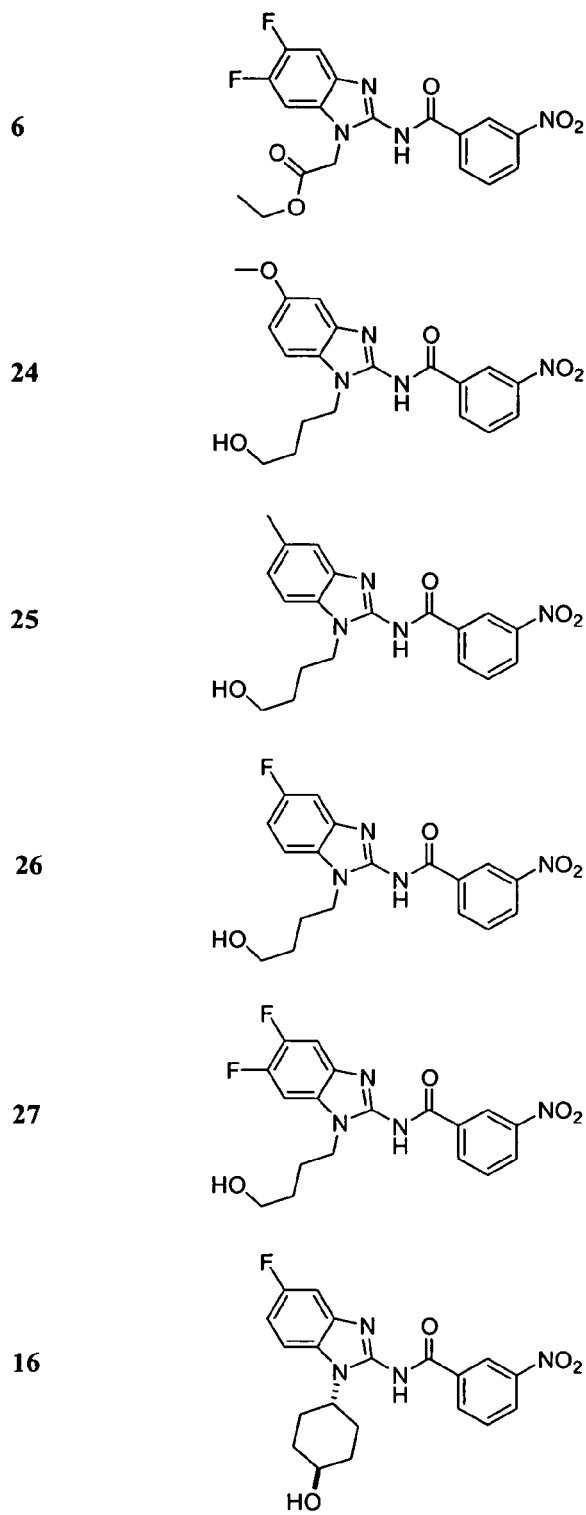
Figure 1E:
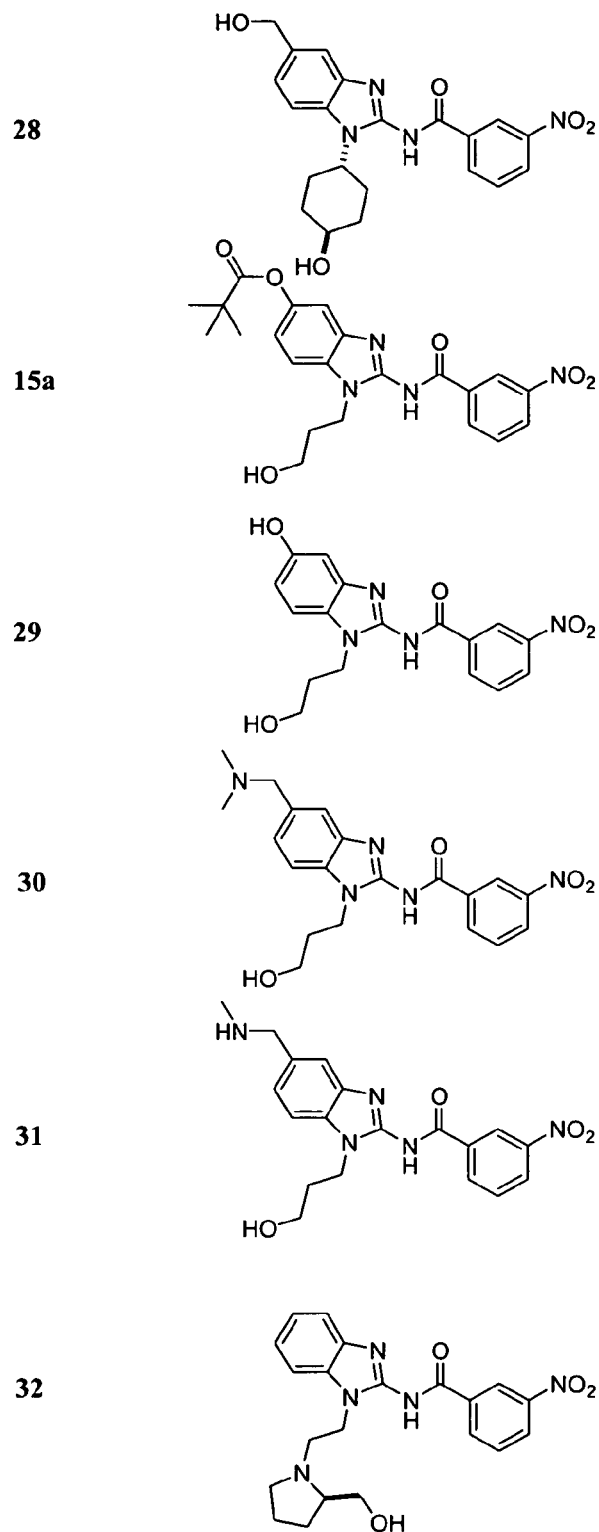
Figure 2A:
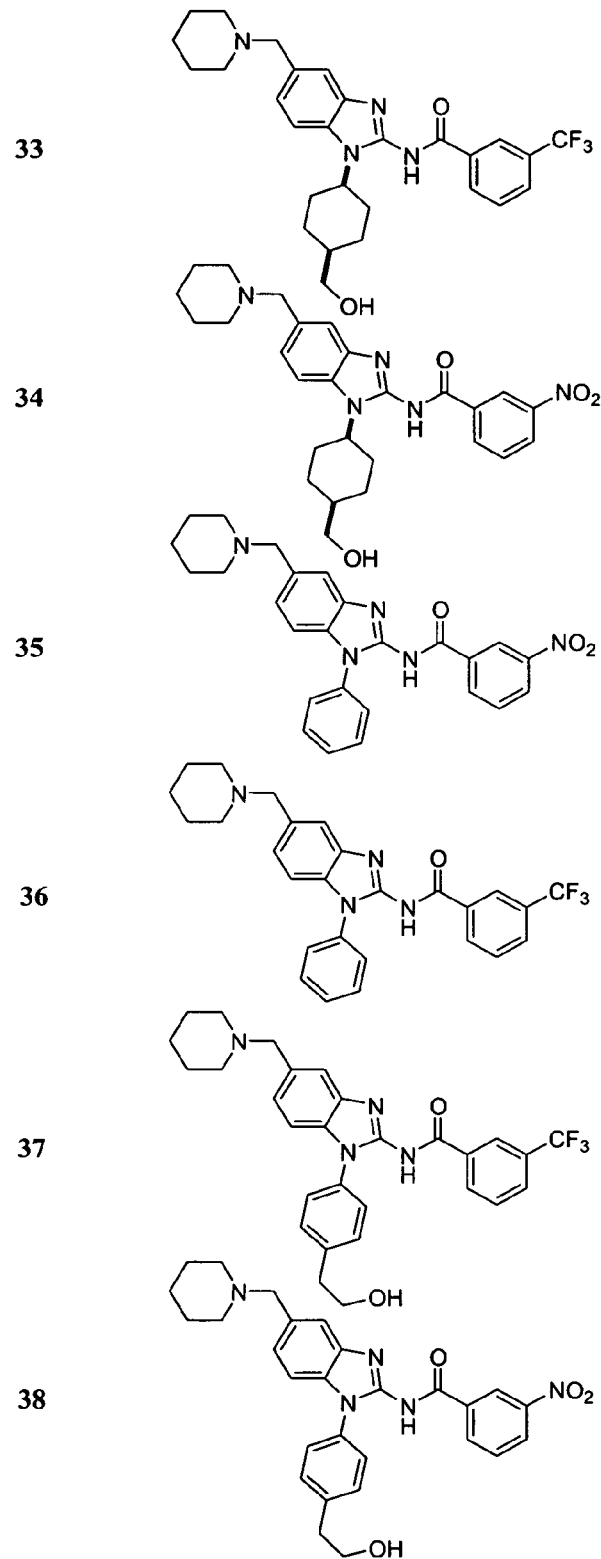
FIGS. 2a to 2e provide exemplary structures of compounds disclosed herein.
Figure 2B:
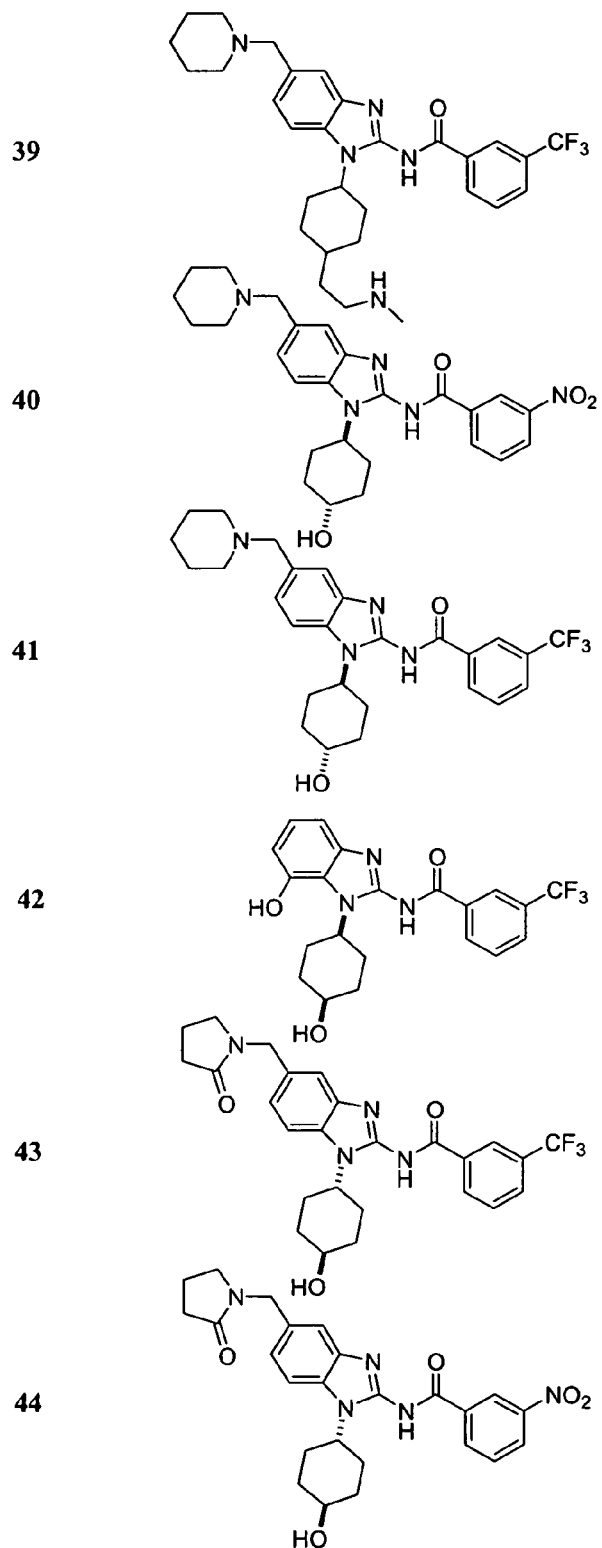
Figure 2C:
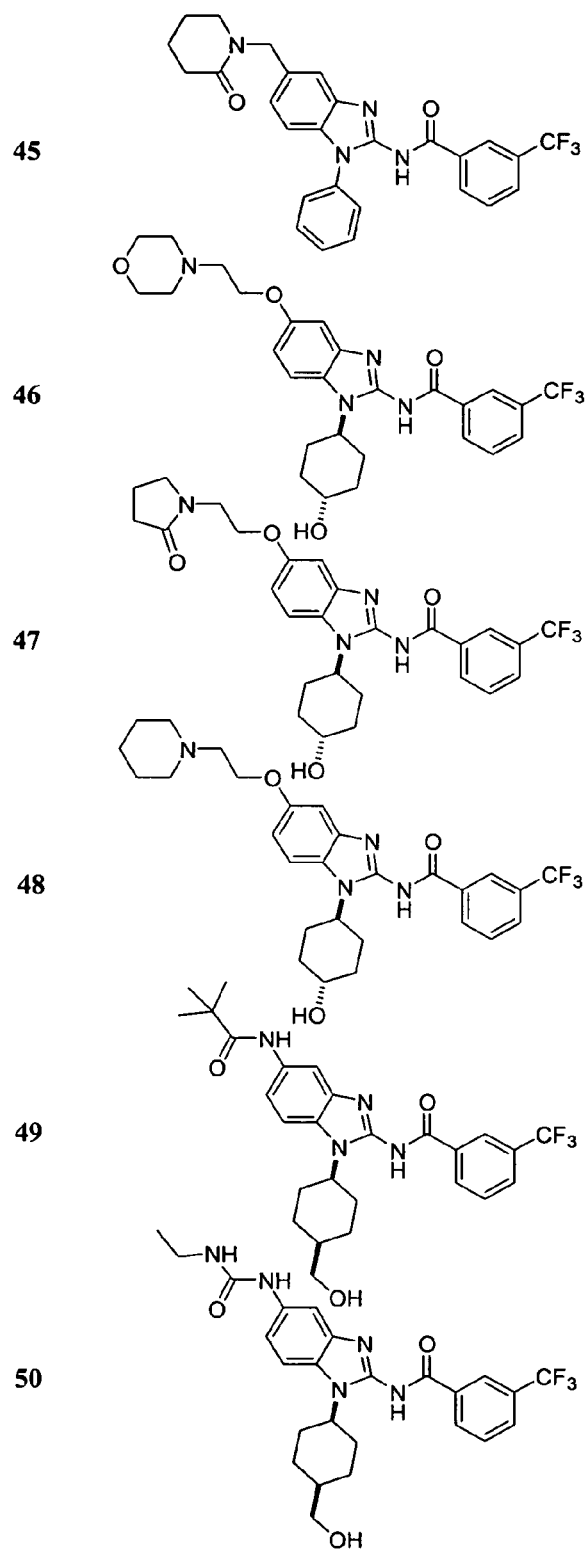
Figure 2D:
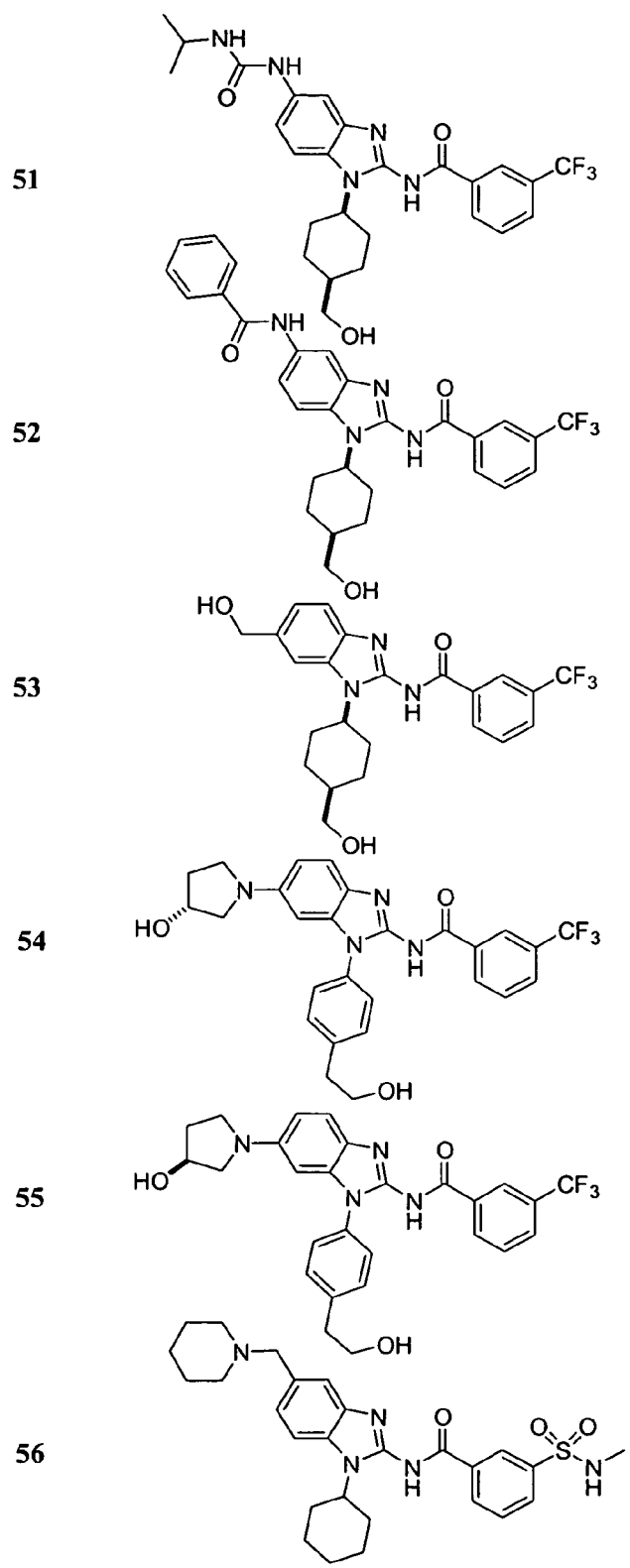
Figure 2E:
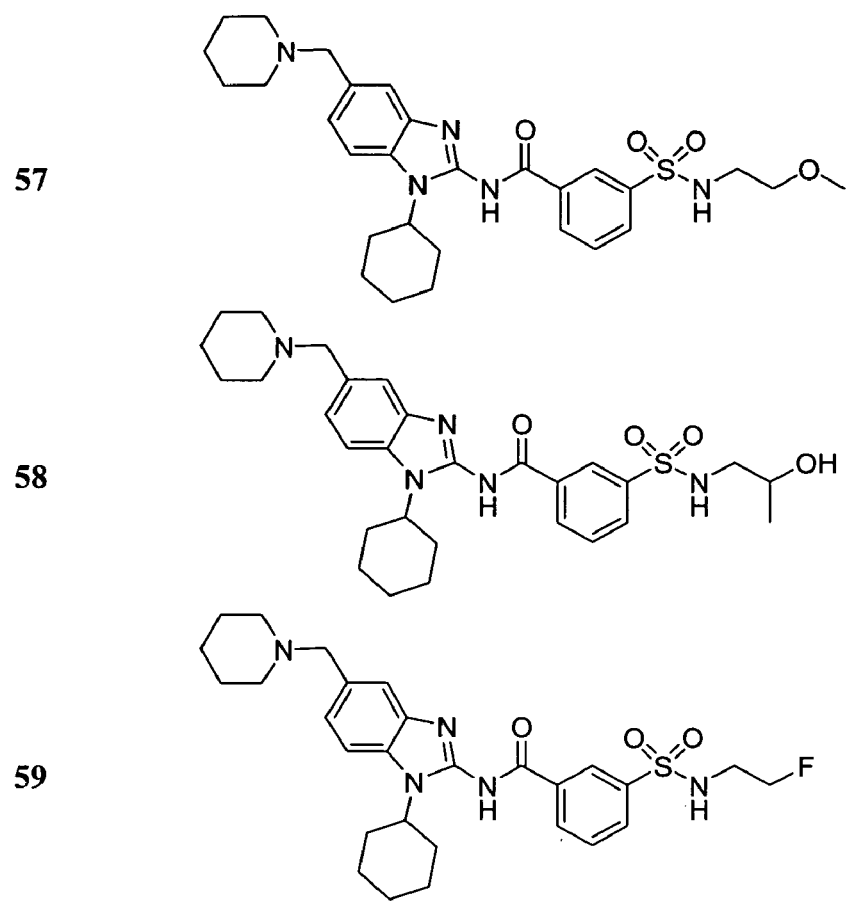
Figure 3A:
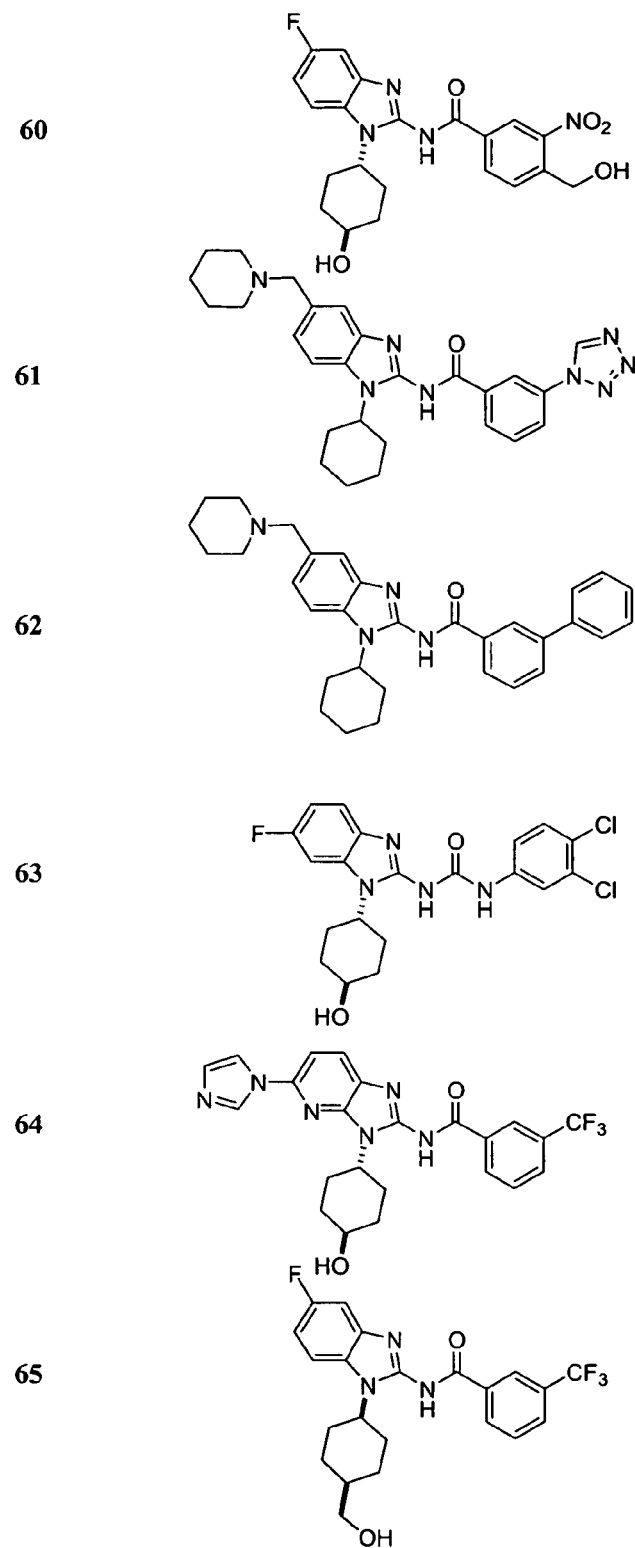
FIGS. 3a to 3c provide exemplary structures of compounds disclosed herein.
Figure 3B:
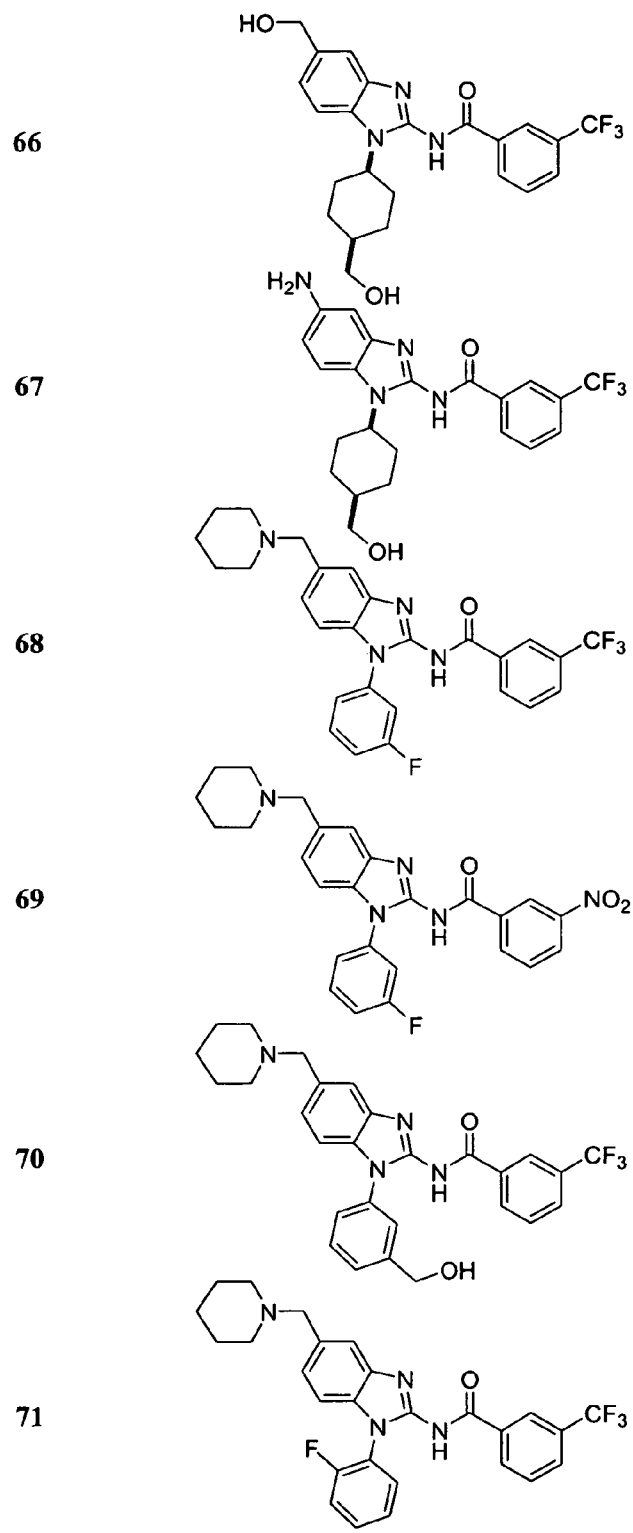
Figure 3C:
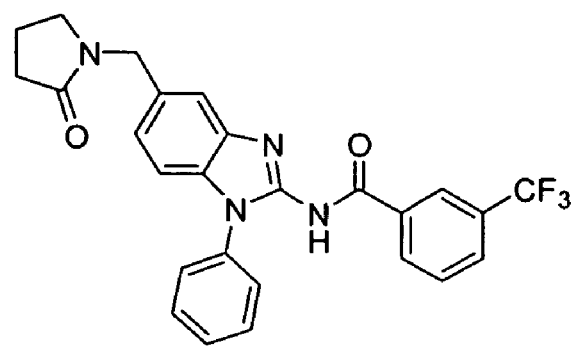

Exemplary compounds of the invention are provided in FIGS. 1a-3c.

The vast majority of the compounds contemplated for use in the present invention are novel, while some are available from commercial sources. The present invention specifically contemplates the exclusion of commercially available compounds from the compound claims (and, if appropriate, from the pharmaceutical composition claims). Unless otherwise indicated, it is to be understood that the invention includes those compounds that are novel, as well as pharmaceutical compositions, various methods (e.g., methods of treating or preventing certain IRAK-mediated conditions and diseases), and the like which include both the novel compounds of the invention and compounds that are commercially available. Exemplary commercially available benzimidazoles include nocodazole, carbendazim, mebendazole, albendazole, benomyl, thiabendazole, fenbendazole, oxfendazole and flubendazole.

Synthesis of IRAK Modulators

Synthesis routes to the compounds provided herein are described in the Examples. One of skill in the art will appreciate that the substituents (e.g., R', R", R'", etc.) can be altered before, during or after preparation of the heterocyclic scaffolding and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group.

Compositions

In another aspect, the present invention provides pharmaceutical compositions for modulating IRAK. The compositions comprise a compound of the present invention with a pharmaceutically acceptable carrier or excipient.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

In one embodiment, the invention provides the subject compounds combined with a pharmaceutically acceptable excipient such as sterile saline, methylcellulose solutions, detergent solutions or other medium, water, gelatin, oils, etc. The compounds or compositions may be administered alone or in combination with any convenient carrier, diluent, etc., and such administration may be provided in single or multiple dosages. Useful carriers include water soluble and water insoluble solids, fatty acids, micelles, inverse micelles, liposomes and semi-solid or liquid media, including aqueous solutions and non-toxic organic solvents. All of the above formulations may be treated with ultrasounds, stirred, mixed, high-shear mixed, heated, ground, milled, aerosolized, pulverized, lyophilized, etc. to form pharmaceutically acceptable compositions.

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical use, creams, ointments, jellies, solutions or suspensions, etc., containing the compounds of the present invention are employed. As used herein, topical application is also meant to include the use of mouthwashes and gargles.

The pharmaceutical compositions and methods of the present invention may further comprise other therapeutically active compounds as noted herein which are usually applied in the treatment or prevention of the above mentioned pathological conditions.

Methods of Use

The compounds and compositions of the present invention can be used to treat and/or prevent conditions and disorders associated with IL-1 signaling, such as inflammatory conditions, cancer and various immune disorders. These conditions or disorders include, but are not limited to: (1) inflammatory or allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic), multiple sclerosis, systemic lupus erythematosus, type I diabetes, glomerulonephritis and the like, (10) graft rejection (including allograft rejection and graft-v-host disease), (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, and (12) cell proliferative or neoplastic diseases such as cancer, e.g., cancer of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, and diseases in which angiogenesis and neovascularization play a role.

Preferably, the present methods are directed to the treatment of diseases or conditions selected from rheumatoid arthritis, inflammatory bowel disease, allergic disease, psoriasis, asthma, multiple sclerosis, graft rejection and sepsis. More preferably, the present methods are directed to the treatment of rheumatoid arthritis, inflammatory bowel disease and multiple sclerosis.

In preferred embodiments, the present invention provides methods of treating or preventing an IRAK-mediated condition or disorder by administering to a subject having such a condition or disorder, a therapeutically effective amount of one or more of the subject compounds or compositions. In one group of embodiments, diseases or conditions, including chronic diseases, of humans or other species can be treated with inhibitors of IRAK function.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation, in which the active ingredient is released over a defined time period.

In the treatment or prevention of inflammatory conditions and immune disorders or other conditions or diseases mediated by IRAK, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of, for example, 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related or complementary utilities to prevent and treat inflammatory and immune-related conditions and diseases, including rheumatoid arthritis, inflammatory bowel disease, multiple sclerosis and those pathologies noted above. In some embodiments, such combination therapy is used in the treatment or prevention of a condition or disorder mediated by IRAK.

For example, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 (COX-2) inhibitor, an interleukin inhibitor, such as an interleukin-1 receptor antagonist, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sulindac, tenidap, and the like. Similarly, the instant compounds may be administered with an analgesic listed above; a potentiator such as caffeine, an H2-antagonist (e.g., ranitidine), simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine.

Likewise, compounds and compositions of the present invention may be used in combination with other drugs that are used in the treatment, prevention, suppression or amelioration of the conditions or diseases for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients or therapeutic agents, in addition to a compound of the present invention. Examples of other therapeutic agents that may be combined with a compound of the present invention, either administered separately or in the same pharmaceutical compositions, include, but are not limited to: (a) VLA-4 antagonists, (b) corticosteroids, such as beclomethasone, methylprednisolone, betamethasone, prednisone, prednisolone, dexamethasone, fluticasone and hydrocortisone, and corticosteroid analogs such as budesonide; (c) immunosuppressants such as cyclosporine (cyclosporine A, Sandimmune®, Neoral®), tacrolimus (FK-506, Prograf®, rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid, sulfasalazine and analogs, mesalamine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) interleukin inhibitors, such as interleukin-1 (IL-1) inhibitors, and chemokine receptor antagonists; (j) cholesterol lowering agents such as HMG-CoA reductase inhibitors (lovastatin, simvastatin, pravastatin, fluvastatin, atorvastatin and other statins), bile acid sequestrants (e.g., cholestyramine and colestipol), nicotinic acid (niacin), fibric acid derivatives (gemfibrozil, clofibrate, fenofibrate and benzafibrate), probucol and nitroglycerin; (k) anti-diabetic agents such as insulin, sulfonylureas (e.g., glyburide, meglinatide), biguanides, e.g., metformin (Glucophage®), α-glucosidase inhibitors (acarbose), thiazolidinone compounds, e.g., rosiglitazone (Avandia®), troglitazone (Rezulin®) and pioglitazone (Actos®); (l) preparations of interferon beta (interferon β-1α, interferon β-1β); (m) gold compounds such as auranofin and aurothioglucose, (n) etanercept (Enbrel®), (o) antibody therapies such as orthoclone (OKT3), daclizumab (Zenapax®), basiliximab (Simulect®), infliximab (Remicade®) and D2E6 TNF antibody, (p) lubricants or emollients such as petrolatum and lanolin, (q) keratolytic agents, (r) vitamin $D_3$ derivatives, e.g., calcipotriene or calcipotriol (Dovonex®), (s) PUVA, (t) anthralin (Drithrocreme®), (u) etretinate (Tegison®) and isotretinoin, (v) multiple sclerosis therapeutic agents such as interferon β-1β, (Betaseron®), interferon β-1α (Avonex®), azathioprine (Imurek®, Imuran®), glatiramer acetate (Capoxone®), a glucocorticoid (e.g., prednisolone) and cyclophosphamide and (w) β3 adrenergic receptor agonists, leptin or derivatives thereof, and neuropeptide Y (e.g., NPY5) antagonists; (x) other compounds such as 5-aminosalicylic acid and prodrugs thereof; (y) DNA-alkylating agents (e.g., cyclophosphamide, ifosfamide), antimetabolites (e.g., azathioprene, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, and hormone therapy (e.g., tamoxifen, and flutamide). The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In still other particularly preferred embodiments, the present methods are directed to the treatment of rheumatoid arthritis, wherein the compound of the invention is administered either alone or in combination with a second therapeutic agent selected from methotrexate, sulfasalazine, a COX-2 inhibitor, hydroxychloroquine, cyclosporine A, D-penicillamine, infliximab, etanercept, auranofin and aurothioglucose. When used in combination, the practitioner can administer a combination of the therapeutic agents, or administration can be sequential.

In yet other particularly preferred embodiments, the present methods are directed to the treatment of inflammatory bowel disease wherein the compound of the invention is used alone or in combination with a second therapeutic agent selected from sulfasalazine and analogs (e.g., olsalazine), mesalamine, corticosteroids (e.g., prednisone, prednisolone) and analogs (e.g., budesonide), azathioprine, 6-mercaptopurine, cyclosporine A, methotrextate, infliximab and an IL-1 inhibitor.

In other particularly preferred embodiments, the present methods are directed to the treatment of multiple sclerosis using a compound of the invention either alone or in combination with a second therapeutic agent selected from interferon β-1β, interferon β-1α, azathioprine, glatiramer acetate, a glucocorticoid (e.g., prednisolone) and cyclophosphamide.

Methods of Evaluating Putative IRAK Modulators

In yet another aspect, the present invention includes methods to evaluate putative specific agonists or antagonists of IRAK function. Accordingly, the present invention is directed to the use of these compounds in the preparation and execution of screening assays for compounds which modulate the function of the IRAK. For example, the compounds of this invention are useful for isolating receptor mutants, which are excellent screening tools for potent compounds. Furthermore, the compounds of this invention are useful in establishing or determining the binding site of other compounds to IRAK, e.g., by competitive inhibition. The compounds of the instant invention are also useful for the evaluation of putative specific modulators of IRAK.

The following examples are offered by way of illustration and not by way of limitation.

EXAMPLES

Reagents and solvents used below can be obtained from commercial sources such as Aldrich Chemical Co. (Milwaukee, Wis., USA). $^1$H-NMR spectra were recorded on a Bruker 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz), number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter (μL) was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

Example 1

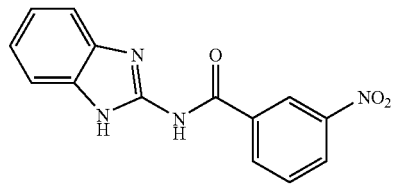

1

Synthesis of 3-nitro-N-(1H-benzoimidazol-2-yl)-benzamide (1). A 200 mL flask was charged with 2.25 g 3-nitrobenzoic acid (13.46 mmol, 1.0 equiv), 3.59 g 2-aminobenzimidazole (26.92 mmol, 2.0 equiv), 5.63 g O-benzotriazol-1-yl-N,N,N',N'-tetramethyluronium hexafluorophosphate (HBTU, 14.81 mmol, 1.10 equiv), and 1-hydroxybenzotriazole hydrate (HOBT, 14.13 mmol, 1.05 equiv). The flask was then charged with 40 mL DMF, stirring was initiated (magnetic stirrer) and 1.71 mL N-methylmorpholine (NMM, 15.48 mmol, 1.15 equiv) was added in one portion to the suspension. After 6 h, the suspension was diluted with 200 mL of a 10% citric acid solution. After stirring an additional 30 min, the suspension was filtered and the resulting solid was washed (2×H$_2$O, then 2×sat. NaHCO$_3$). The solid was then triturated with EtOAc (30 mL), filtered, and dried under reduced pressure to give 3.16 g of the product as a tan solid (11.2 mmol). $^1$H NMR (DMSO-d$_6$, 400 MHz) δ 12.60 (broad s, 2H), 8.96 (t, J=2.1 Hz, 1H), 8.55 (d, J=7.8 Hz, 1H), 8.38 (m, 1H), 7.78 (t, J=7.9 Hz, 1H), 7.43 (dd, J=3.2, 5.9 Hz, 2H), 7.18 (dd, J=3.2, 5.9 Hz, 2H); MS: ESI(−) m/z 281.1 (M−H).

Example 2

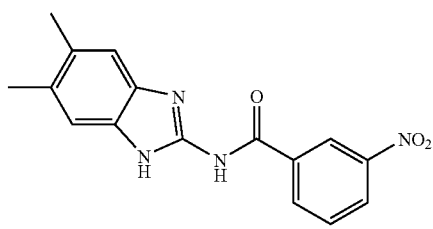

2

Synthesis of 3-nitro-N-(5,6-dimethyl-1H-benzoimidazol-2-yl)-benzamide (2). Using the same method as Example 1, and substituting 2-amino-5,6-dimethylbenzimidazole for 2-aminobenzimidazole the following was prepared: 3-Nitro-N-(5,6-dimethyl-1H-benzoimidazol-2-yl)-benzamide: $^1$H NMR (DMSO-d$_6$, 400 MHz) δ 12.40 (broad s, 2H), 8.96 (s, 1H), 8.54 (d, J=7.8 Hz, 1H), 8.37 (dd, J=2.3, 8.1 Hz, 1H), 7.77 (t, J=8.0 Hz, 1H), 7.21 (s, 2H), 2.28 (s, 6H).

Example 3

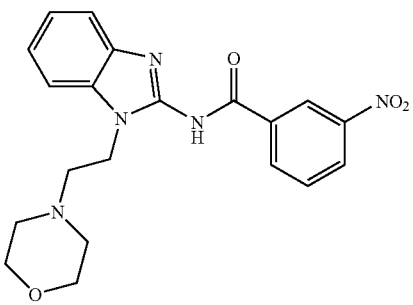

3

Synthesis of 3-nitro-N-(1-(2-morpholin-4-yl-ethyl)-1H-benzoimidazol-2-yl)-benzamide (3). To a suspension of 3-nitro-N-(1H-benzoimidazol-2-yl)-benzamide prepared above in Example 1 (150 mg, 0.532 mmol, 1.0 equiv) in 3 mL of 5:1 acetone:DMF was added 109 mg of 4-(2-chloroethyl)morpholine hydrochloride (0.585 mmol, 1.1 equiv) and 221 mg $K_2CO_3$ (1.60 mmol, 3.0 equiv). The resulting suspension was heated to 54° C. with stirring for 3 h. The suspension was then diluted with 10 mL sat. $NaHCO_3$, and the acetone was removed under reduced pressure. The resulting suspension was then diluted with 20 mL $CH_2Cl_2$, shaken until no solids remained, and passed through a 20 mm (40 mL) 3M Empore octadecyl (C18) cartridge to remove water. The collected organics were then concentrated under reduced pressure. Purification by flash chromatography ($SiO_2$, 2-4% MeOH/$CH_2Cl_2$) gave 124 mg of the product as a tan solid (0.314 mmol). $^1$H NMR (DMSO-$d_6$, 400 MHz) δ 12.85 (s, 1H), 8.97 (s, 1H), 8.61 (d, J=7.6 Hz, 1H), 8.38 (d, J=7.5 Hz, 1H), 7.79 (t, J=8.0 Hz, 1H), 7.58 (t, J=7.6 Hz, 2H), 7.26 (m, 2H), 4.42 (t, J=5.9 Hz, 2H), 3.49 (m, 4H), 2.75 (t, J=5.9 Hz, 2H), 2.55 (m, 4H).

Example 4

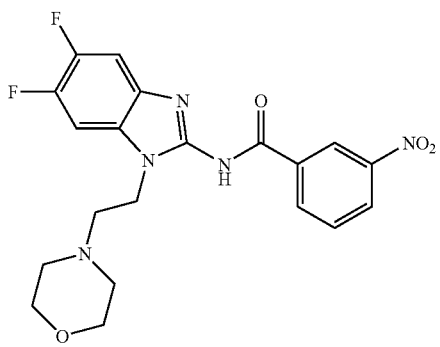

4

Synthesis of 3-nitro-N-(1-(2-morpholin-4-yl-ethyl)-5,6-difluoro-1H-benzoimidazol-2-yl)-benzamide(4). Using the methods described in Examples 1 and 3 above, substituting 5,6-difluoro-2-aminobenzimidazole for 2-amino benzimidazole the following was prepared: 3-Nitro-N-(1-(2-morpholin-4-yl-ethyl)-5,6-difluoro-1H-benzoimidazol-2-yl)-benzamide: $^1$H NMR (DMSO-$d_6$, 400 MHz) δ 12.90 (s, 1H), 8.93 (s, 1H), 8.59 (d, J=7.7 Hz, 1H), 8.38 (dd, J=1.6, 8.1 Hz, 1H), 7.87 (dd, J=7.1, 10.6 Hz, 1H), 7.78 (t, J=7.9 Hz, 1H), 7.52 (dd, J=7.4, 10.1 Hz, 1H), 4.38 (t, J=6.3; H, 2H), 3.44 (m, 4H), 2.73 (m, 2H), 2.53 (m, 4H).

Example 5

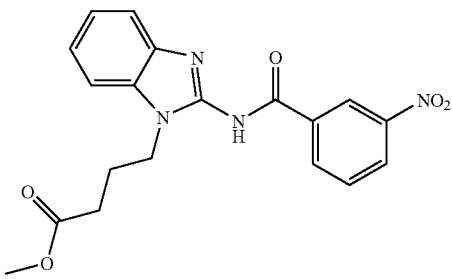

5

Synthesis of 3-nitro-N-(1-(3-carboxymethylpropyl)-1H-benzoimidazol-2-yl)-benzamide (5). Using the methods described in Examples 1 and 3, and substituting methyl 4-iodobutyrate for 4-(2-chloroethyl)morpholine hydrochloride the following was prepared: 3-Nitro-N-(1-(3-carboxymethylpropyl)-1H-benzoimidazol-2-yl)-benzamide: $^1$H NMR (DMSO-$d_6$, 400 MHz) δ 12.85 (s, 1H), 8.93 (s, 1H), 8.67 (d, J=7.6 Hz, 1H), 8.37 (dd, J=2.4, 8.1 Hz, 1H), 7.78 (t, J=7.9 Hz, 1H), 7.58 (d, J=8.3 Hz, 2H), 7.27 (m, 2H), 4.35 (t, J=6.7 Hz, 2H), 3.34 (s, 3 H), 2.43 (t, J=7.0 Hz, 2H), 2.10 (m, 2H); MS: ESI(−) m/z 381.1 (M−H).

Example 6

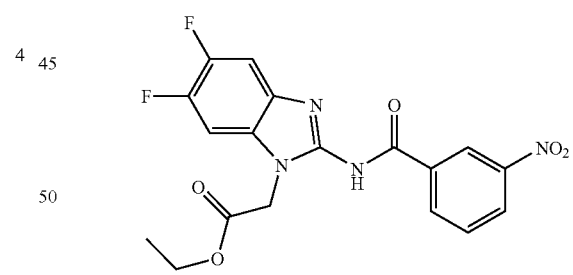

6

Synthesis of 3-nitro-N-(1-(ethyl acet-2-yl)-5,6-difluoro-1H-benzoimidazol-2-yl)-benzamide (6). Using the methods described in examples 1 and 3 above, substituting 5,6-difluoro-2-aminobenzimidazole for 2-amino benzimidazole and ethyl 2-iodoacetate for 4-(2-chloroethyl)morpholine hydrochloride the following was prepared: 3-nitro-N-(1-(ethyl acet-2-yl)-5,6-difluoro-1H-benzoimidazol-2-yl)-benzamide: $^1$H NMR (DMSO-$d_6$, 400 MHz) δ 13.0 (s, 1H), 8.86 (t, J=2.1 Hz, 1H), 8.56 (d, J=7.7 Hz, 1H), 8.38 (dd, J=1.4, 8.1 Hz, 1H), 7.86 (dd, J=7.0, 10.5 Hz, 1H), 7.76 (t, J=8.0 Hz, 1H), 7.51 (dd, J=7.3, 10.0 Hz, 1H), 5.13 (s, 2H), 4.22 (m, 2 H), 1.23 (t, J=7.1 Hz, 3H).

Example 7

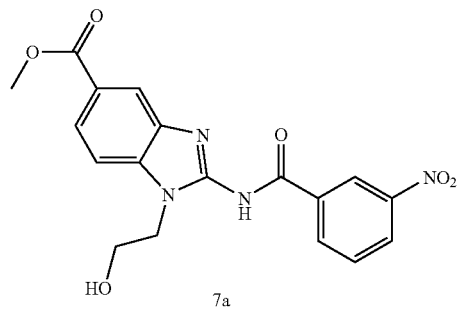

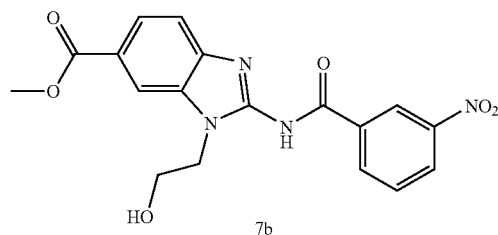

Synthesis of 3-nitro-N-(1-hydroxyethyl-5-carboxymethyl-1H-benzoimidazol-2-yl)-benzamide (7a) and 3-nitro-N-(1-hydroxyethyl-6-carboxymethyl-1H-benzoimidazol-2-yl)-benzamide (7b). Using the methods described in examples 1 and 3 above, substituting 5-carboxymethyl-2-aminobenzimidazole for 2-amino benzimidazole and 2-iodoethanol for 4-(2-chloroethyl)morpholine hydrochloride the following was prepared: 3-Nitro-N-(1-hydroxyethyl-5-carboxymethyl-1H-benzoimidazol-2-yl)-benzamide and 3-nitro-N-(1-hydroxyethyl-6-carboxymethyl-1H-benzoimidazol-2-yl)-benzamide as a mixture of the two isomers: $^1$H NMR (DMSO-$d_6$, 400 MHz, mixture of isomers) δ 13.09 (s, 0.5; H), 13.03 (s, 0.5; H), 8.9 (s, 1H), 8.64 (d, J=7.6 Hz, 1H), 8.38 (d, J=8.2 Hz, 1H), 8.13 (s, 0.5; H), 8.09 (s, 0.5; H), 7.87 (m, 1H), 7.78 (t, J=15.8 Hz, 1H), 7.64 (t, J=15.7 Hz, 1H), 4.98 (broad s, 1H), 4.36 (dd, J=6.9, 12.4 Hz, 2H), 3.88 (s, 3H), 3.85 (m, 2H).

Example 8

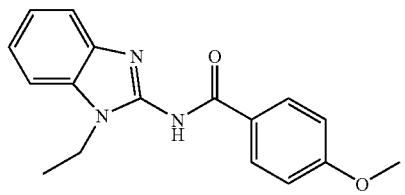

Synthesis of 4-methoxy-N-(1-ethyl-1H-benzoimidazol-2-yl)-benzamide (8). Using the methods described in Examples 1 and 3 above, substituting 4-methoxybenzoic acid for 3-nitrobenzoic acid, and 2-iodoethane for 4-(2-chloroethyl)morpholine hydrochloride the following was prepared: 4-Methoxy-N-(1-ethyl-1H-benzoimidazol-2-yl)-benzamide: $^1$H NMR (DMSO-$d_6$, 400 MHz) δ 12.60 (s, 1H), 8.20 (d, J=8.5 Hz, 2H), 7.49 (dd, J=4.6, 6.9 Hz, 2H), 7.20 (m, 2H), 6.99 (d, J=8.5 Hz, 2H), 4.27 (dd, J=6.5, 13.5 Hz, 2H), 3.84 (s, 3H), 1.33 (t, J=7.0 Hz, 3H).

Example 9

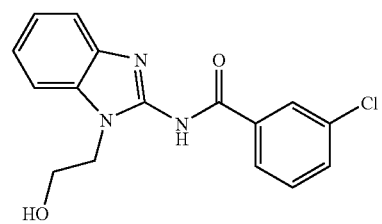

Synthesis of 3-chloro-N-(1-hydroxyethyl-1H-benzoimidazol-2-yl)-benzamide (9). Using the methods described in Examples 1 and 3 above, substituting 3-chlorobenzoic acid for 3-nitrobenzoic acid, and 2-iodoethanol for 4-(2-chloroethyl)morpholine hydrochloride the following was prepared: 3-Chloro-N-(1-hydroxyethyl-1H-benzoimidazol-2-yl)-benzamide: $^1$H NMR (DMSO-$d_6$, 400 MHz) δ 12.80 (s, 1H), 8.18 (m, 2H), 7.60-7.48 (m, 4H), 7.23 (m, 2H), 4.97 (t, J=5.5 Hz, 1H), 4.32 (t, J=5.5 Hz, 2H), 3.82 (dd, J=5.3, 10.7 Hz, 2H).

Example 10

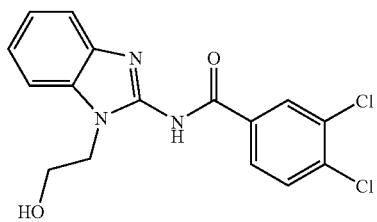

Synthesis of 3,4-dichloro-N-(1-hydroxyethyl-1H-benzoimidazol-2-yl)-benzamide (10). Using the methods described in Examples 1 and 3 above, substituting 3,4-dichlorobenzoic acid for 3-nitrobenzoic acid, and 2-iodoethanol for 4-(2-chloroethyl)morpholine hydrochloride the following was prepared: 3,4-Dichloro-N-(1-hydroxyethyl-1H-benzoimidazol-2-yl)-benzamide: $^1$H NMR (DMSO-$d_6$, 400 MHz) δ 12.80 (s, 1H), 8.30 (d, J=8.3 Hz, 1H), 8.17 (dd, J=1.9, 8.3 Hz, 1H), 7.75 (d, J=8.3 Hz, 1H), 7.53 (m, 2H), 7.22 (m, 2H), 4.94 (t, J=5.6 Hz, 1H), 4.31 (t, J=5.5 Hz, 2H), 3.81 (dd, J=5.4, 10.9 Hz, 2H).

Example 11

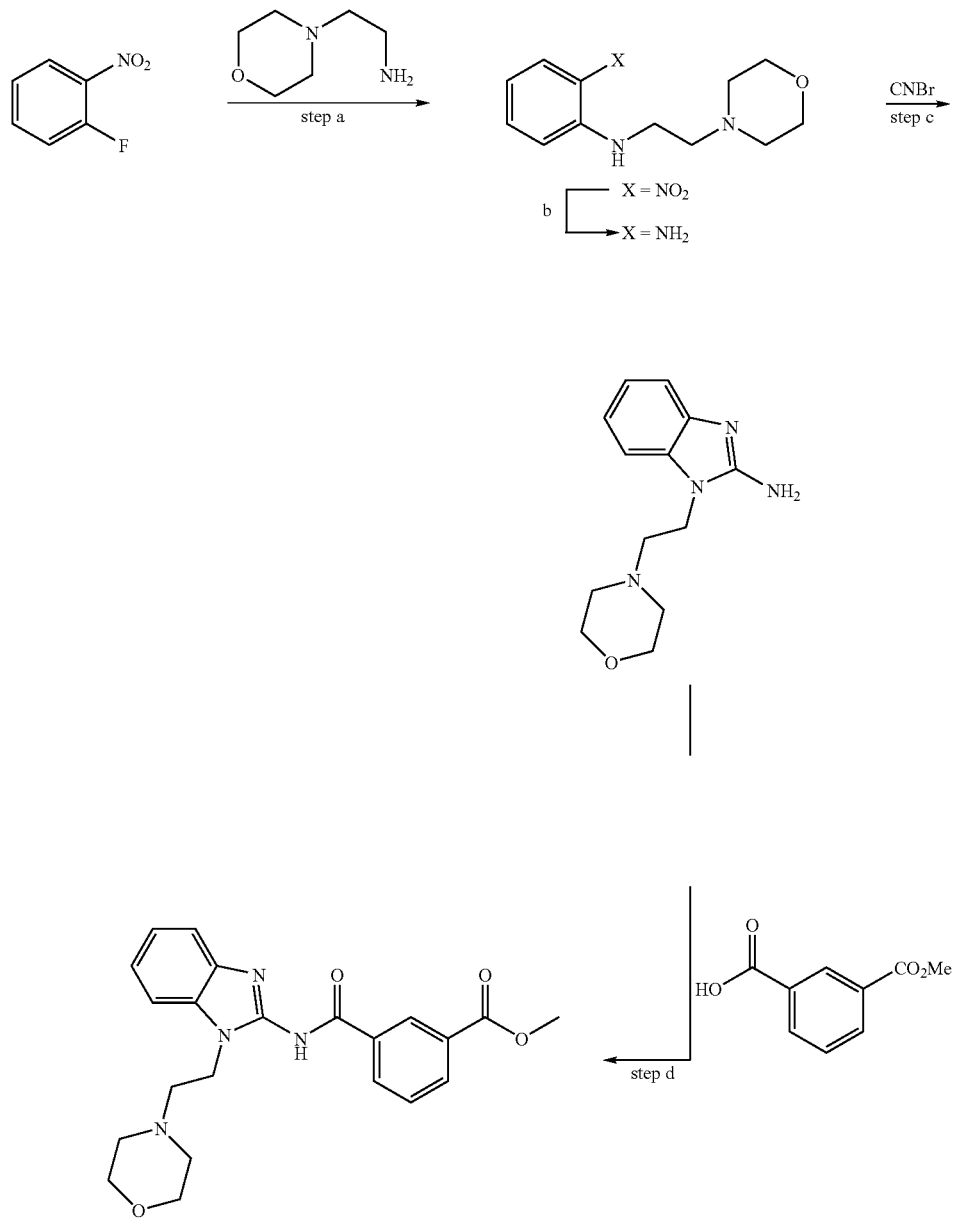

Synthesis of 3-carboxymethyl-N-(1-(2-morpholin-4-yl-ethyl)-1H-benzoimidazol-2-yl)-benzamide (11)

(a) 2-(4-(2-Aminoethyl)morpholine)nitrobenzene: To a 25 mL flask containing 2.0 mL 2-fluoronitrobenzene (19.0 mmol, 1.0 equiv) was carefully added 2.48 mL 4-(2-aminoethyl)morpholine (19.0 mmol, 1.0 equiv) over a period of 15 min (caution, exothermic reaction). The reaction was allowed to stir for 12 h at which time it was diluted with sat. NaHCO$_3$. The solution was then extracted (3×CH$_2$Cl$_2$), dried (Na$_2$SO$_4$), and concentrated under reduced pressure. Purification by flash chromatography (SiO$_2$, 0-5% MeOH/CH$_2$Cl$_2$) gave the product 2-(4-(2-aminoethyl)morpholine)nitrobenzene as a yellow oil 3.69 g (14.7 mmol).

(b) 2-(4-(2-Aminoethyl)morpholine)aniline: A 200 mL flask was charged with 1.0 g of palladium on carbon (5 wt %), and 5 mL EtOH under N$_2$. 3.7 g 2-(4-(2-Aminoethyl)morpholine)nitrobenzene (14.7 mmol, 1.0 equiv) was dissolved in 20 mL EtOH, and the solution was added to the catalyst suspension, followed by the addition of 7 mL cyclohexene. The flask was equipped with a reflux condenser, and heated to 83° C. After stirring for 1 h, the suspension was removed from the heating bath and allowed to cool to rt. The suspension was then filtered through a pad of celite to remove the catalyst, and the celite pad was washed 6×EtOH. The combined organics were concentrated under reduced pressure to give the product 2-(4-(2-aminoethyl)morpholine)aniline as a black viscous oil which was sufficiently pure to continue to the next step (3.96 g, quant.).

(c) 1-(2-Morpholin-4-yl-ethyl)-2-aminobenzimidazole: A 250 mL flask was charged with 40 mL $H_2O$ followed by the addition of 3.94 mL of a 5.0 M solution of cyanogen bromide in $CH_3CN$ (19.7 mmol, 1.1 equiv). The 2-(4-(2-aminoethyl) morpholine)aniline prepared above (3.96 g, ~17.92 mmol, 1.0 equiv) was dissolved in 40 mL MeOH, and was introduced via addition funnel over a period of 1 h to the cyanogen bromide solution. After stirring for 24 h the solution was concentrated under reduced pressure to remove MeOH, and the resulting acidic aqueous solution was washed 2×EtOAc. The EtOAc fractions were back extracted 1×$H_2O$, and the combined aqueous solutions were neutralized with sat. $NaHCO_3$. The slightly basic aqueous solution was then extracted 4×EtOAc. The organics from the basic extraction were then washed (1×brine), dried ($MgSO_4$), and concentrated under reduced pressure to give the crude product 1-(2-morpholin-4-yl-ethyl)-2-aminobenzimidazole as a dark brown solid.

(d) 3-Carboxymethyl-N-(1-(2-morpholin-4-yl-ethyl)-1H-benzoimidazol-2-yl)-benzamide: A portion of the product 1-(2-morpholin-4-yl-ethyl)-2-aminobenzimidazole obtained above (100 mg, 0.406 mmol, 1.0 equiv) was combined in a flask with 169 mg O-benzotriazol-1-yl-N,N,N',N'-tetramethyluronium hexafluorophosphate (HBTU, 0.447 mmol, 1.1 equiv), 73.2 mg 3-carboxymethylbenzoic acid (0.406 mmol, 1.0 equiv) and 58 mg 1-hydroxybenzotriazole hydrate (HOBT, 0.426 mmol, 1.05 equiv) followed by the addition of 2 mL DMF and 51 µL N-methylmorpholine (NMM, 0.467 mmol, 1.15 equiv). The solution was allowed to stir for 24 h followed by dilution with 30 mL sat. $NaHCO_3$. The resulting solution was extracted (1×EtOAc), dried ($Na_2SO_4$), and concentrated under reduced pressure. Purification by flash chromatography ($SiO_2$, 2-4% MeOH/$CH_2Cl_2$) gave the product as a tan solid (53 mg, 0.130 mmol). $^1$H NMR (DMSO-$d_6$, 400 MHz) δ 12.8 (s, 1H), 8.82 (s, 1H), 8.44 (m, 1H), 8.08 (m, 1H), 7.64 (m, 1H), 7.55 (m, 2H), 7.25 (m, 2H), 4.39 (m, 2H), 3.85 (s, 3H), 3.48 (m, 4H), 2.71 (m, 2H), 2.50 (m, 4H).

Example 12

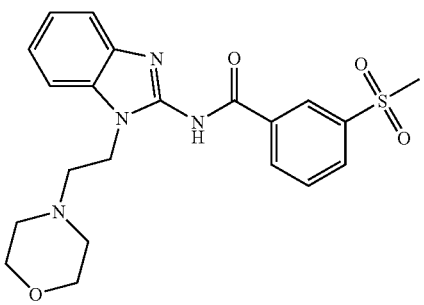

12

Synthesis of 3-methanesulfonyl-N-(1-(2-morpholin-4-yl-ethyl)-1H-benzoimidazol-2-yl)-benzamide (12). Using the methods described above in Example 11 the following compounds were prepared substituting the appropriate carboxylic acid for 3-carboxymethylbenzoic acid in step (d):

3-Methanesulfonyl-N-(1-(2-morpholin-4-yl-ethyl)-1H-benzoimidazol-2-yl)-benzamide from 1-(2-morpholin-4-yl-ethyl)-2-aminobenzimidazole and 3-methanesulfonylbenzoic acid: $^1$H NMR (DMSO-$d_6$, 400 MHz) δ 12.81 (s, 1H), 8.72 (s, 1H), 8.51 (d, J=7.7 Hz, 1H), 8.09 (d, J=7.8 Hz, 1H), 7.77 (t, J=7.8 Hz, 1H), 7.57 (m, 2H), 7.24 (m, 2H), 4.42 (t, J=6.4 Hz, 2H), 3.47 (m, 4H), 3.33 (s, 3H), 2.70 (m, 2H), 2.49 (m, 4H).

Example 13

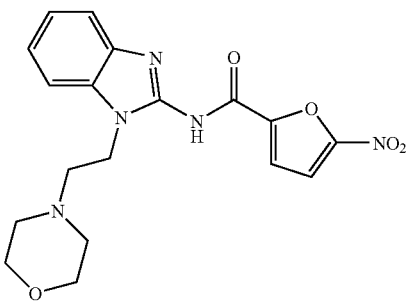

13

Synthesis of 5-nitro-N-(1-(2-morpholin-4-yl-ethyl)-1H-benzoimidazol-2-yl)-2-furamide (13). 5-Nitro-N-(1-(2-morpholin-4-yl-ethyl)-1H-benzoimidazol-2-yl)-2-furamide from 1-(2-morpholin-4-yl-ethyl)-2-aminobenzimidazole and 5-nitro-2-furoic acid: $^1$H NMR (DMSO-$d_6$, 400 MHz) δ 12.70 (s, 1H), 7.73 (m, 1H), 7.57 (m, 2H), 7.35 (m, 1H), 7.28 (m, 2H), 4.38 (m, 2H), 3.43 (m, 4H), 2.70 (m, 2H), 2.50 (m, 4H).

Example 14

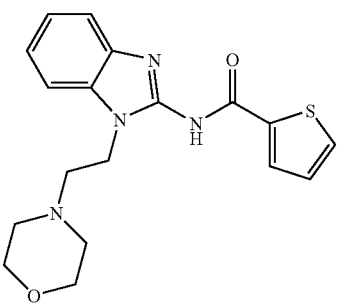

14

Synthesis of N-(1-(2-morpholin-4-yl-ethyl)-1H-benzoimidazol-2-yl)-2-thiophenecarboxamide (14). N-(1-(2-Morpholin-4-yl-ethyl)-1H-benzoimidazol-2-yl)-2-thiophenecarboxamide from 1-(2-morpholin-4-yl-ethyl)-2-aminobenzimidazole and thiophene-2-carboxylic acid: $^1$H NMR (DMSO-$d_6$, 400 MHz) δ 12.55 (s, 1H), 7.69 (dd, J=3.4, 7.7 Hz, 2H), 7.52 (m, 2H), 7.22 (m, 2H), 7.12 (t, J=4.8 Hz, 1H), 4.33 (t, J=6.1 Hz, 2H), 3.45 (m, 4H), 2.71 (m, 2H), 2.49 (m, 4H).

Example 15

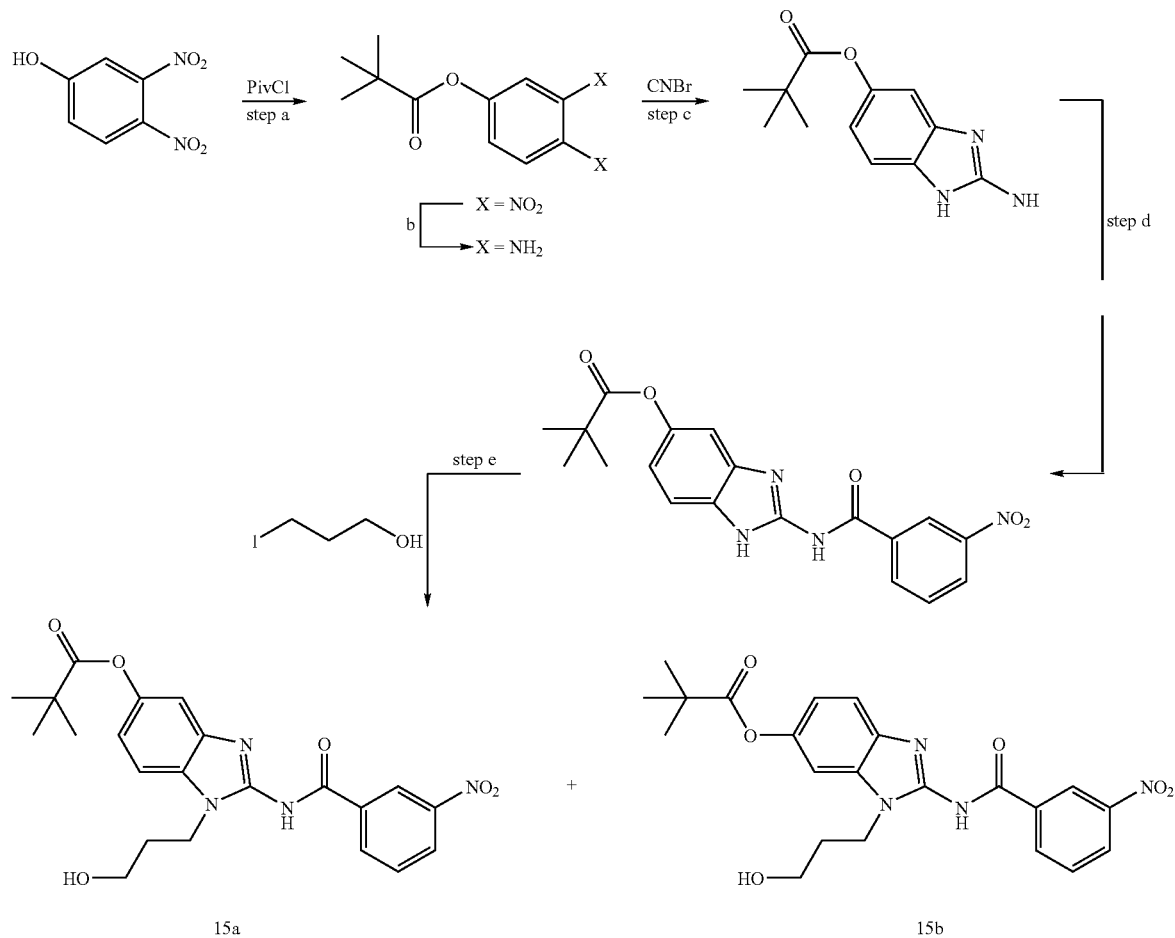

Synthesis of 3-nitro-N-(1-hydroxypropyl-5-(2',2'-dimethylpropionyl)-1H-benzoimidazol-2-yl)-benzamide (15a) and 3-Nitro-N-(1-hydroxypropyl-6-(2',2'-dimethylpropionyl)-1H-benzoimidazol-2-yl)-benzamide (15b). This example illustrates the synthesis of 3-nitro-N-(1-hydroxypropyl-5-(2',2'-dimethylpropionyl)-1H-benzoimidazol-2-yl)-benzamide and 3-Nitro-N-(1-hydroxypropyl-6-(2',2'-dimethylpropionyl)-1H-benzoimidazol-2-yl)-benzamide as a mixture of the two isomers:

(a) 4-(2',2'-Dimethylpropionyl)-1,2-dinitrobenzene: A 1 L flask was charged with 10 g (54.3 mmol, 1.0 equiv) 3,4-dinitrophenol and 300 mL CH$_2$Cl$_2$. The resulting solution was cooled in an ice bath to 0° C. followed by the addition of 9.84 mL triethylamine (70.6 mmol, 1.3 equiv) and 7.35 mL pivoyl chloride (59.7 mmol, 1.1 equiv). After stirring for 15 min the solution was diluted with sat. NaHCO$_3$ and extracted (2×CH$_2$Cl$_2$). The CH$_2$Cl$_2$ solution was then dried (Na$_2$SO$_4$) and concentrated under reduced pressure to give the 4-(2',2'-dimethylpropionyl)-1,2-dinitrobenzene product as a light golden oil which was used directly in the next step.

(b) 4-(2',2'-dimethylpropionyl)-1,2-aminobenzene: A 250 mL flask which had been purged under nitrogen was charged with 2 g 5% wt palladium on carbon and 20 mL EtOH. The starting material (4-(2',2'-dimethylpropionyl)-1,2-dinitrobenzene produced in step (a) above, ~54 mmol) was dissolved in 140 mL EtOH and added to the flask, followed by the addition of 46 mL cyclohexene. The flask was then equipped with a reflux condenser and heated to 80° C. After heating for 24 h the hot suspension was filtered through celite, and the celite pad was washed (4×EtOH). The combined EtOH solutions were concentrated under reduced pressure to give 10.71 g of the product 4-(2',2'-dimethylpropionyl)-1,2-aminobenzene which was taken on to the next step without further purification (51.4 mmol).

(c) 2-Amino-5-(2',2'-dimethylpropionyl)benzimidazole: To a flask containing 60 mL H$_2$O was added 11.32 mL of a 5.0 M solution of cyanogen bromide in CH$_3$CN followed by the addition of 10.71 g 4-(2',2'-dimethylpropionyl)-1,2-aminobenzene (51.5 mmol, prepared above in step (b), 1.0 equiv) in 60 mL EtOH over 30 min via addition funnel. After stirring for 20 h the solution was concentrated under reduced pressure to remove the EtOH. The resulting aqueous solution was washed (2×EtOAc), and the EtOAc fractions were back extracted 2×H$_2$O. The combined aqueous layers were made basic with sat. NaHCO$_3$, and then extracted (3×EtOAc). The organic layer was then washed (1×brine), dried (MgSO$_4$), and concentrated under reduced pressure to give the product benzimidazole as a brown solid (8.59 g, 36.8 mmol): $^1$H NMR (DMSO-d$_6$, 400 MHz) δ 7.04 (d, J=8.3 Hz, 1H), 6.79 (d, J=2.2 Hz, 1H), 6.53 (dd, J=2.2, 8.3 Hz, 1H), 6.31 (broad s, 2H), 1.28 (s, 9H).

(d) 3-Nitro-N-(5-(2',2'-dimethylpropionyl)-1H-benzoimidazol-2-yl)-benzamide: A dry flask was charged with 2.56 g 3-nitrobenzoic acid (15.3 mmol, 1.0 equiv), 4.65 g 2-amino-5-(2',2'-dimethylpropionyl)benzimidazole (prepared above in step (c), 19.9 mmol, 1.3 equiv), 2.18 g 1-hydroxybenzotriazole hydrate (HOBT, 16.1 mmol, 1.05 equiv), and 6.39 g O-benzotriazol-1-yl-N,N,N',N'-tetramethyluronium hexafluorophosphate (HBTU, 16.8 mmol, 1.10 equiv). 45 mL DMF was then added followed by 1.94 mL N-methylmorpholine (NMM, 17.6 mmol, 1.15 equiv). The resulting slurry was allowed to stir for 20 h, and was then diluted with a 10% citric acid solution and extracted (3×EtOAc). The organics were washed (1×10% citric acid, 2×sat. NaHCO$_3$, 1×brine), dried (Na$_2$SO$_4$), and concentrated under reduced pressure. The resulting solid was triturated from MeOH, filtered, washed (3×MeOH), and dried under reduced pressure to give the product as a tan solid (4.87 g, 12.7 mmol): $^1$H NMR (DMSO-d$_6$, 400 MHz) δ 12.60 (broad s, 2H), 8.96 (t, J=1.9 Hz, 1H), 8.55 (d, J=7.8 Hz, 1H), 8.41 (dd, J=1.5, 8.2 Hz, 1H), 7.81 (t, J=7.9 Hz, 1H), 7.45 (d, J=8.6 Hz, 1H), 7.16 (d, J=2.2 Hz, 1H), 6.91 (dd, J=2.2, 8.5 Hz, 1H), 1.30 (s, 9H).

(e) 3-Nitro-N-(1-hydroxypropyl-5-(2',2'-dimethylpropionyl)-1H-benzoimidazol-2-yl)-benzamide and 3-Nitro-N-(1-hydroxypropyl-5-(2',2'-dimethylpropionyl)-1H-benzoimidazol-2-yl)-benzamide: 2.24 g of 3-Nitro-N-(5-(2',2'-dimethylpropionyl)-1H-benzoimidazol-2-yl)-benzamide (prepared above in step (d), 5.86 mmol, 1.0 equiv) was combined in a flask with 2 mL 3-iodopropanol (20.9 mmol, 3.6 equiv), 2 g K$_2$CO$_3$ (14.5 mmol, 2.5 equiv), and 30 mL of a 5:1 solution of acetone/DMF. The suspension was heated to 55° C. for 25 min, and then poured into a solution of sat. NaHCO$_3$. The acetone was removed under reduced pressure, and the aqueous solution was then extracted (4×CH$_2$Cl$_2$), washed (2×H$_2$O), dried (Na$_2$SO$_4$), and concentrated under reduced pressure. The resulting solid was triturated with MeOH, filtered, washed (3×MeOH), and dried under reduced pressure to give the product as a tan solid 953 mg (2.17 mmol): $^1$H NMR (DMSO-d$_6$, 400 MHz, mixture of isomers) δ 12.90 (s, 1H), 8.95 (s, 1H), 8.66 (d, J=7.7 Hz, 1H), 8.39 (dd, J=1.5, 8.1 Hz, 1H), 7.78 (t, J=7.9 Hz, 1H), 7.56 (dd, J=8.7, 13.9 Hz, 1H), 7.40 (d, J=2.1 Hz, 0.5; H), 7.25 (d, J=2.2 Hz, 0.5; H), 7.03 (dd, J=2.2, 8.6 Hz, 0.5; H), 6.98 (dd, J=2.1, 8.5 Hz, 0.5; H), 4.65 (broad s, 1H), 4.35 (m, 2H), 3.50 (m, 2H), 1.98 (m, 2H), 1.32 (s, 9H). Anal. calcd for C$_{22}$H$_{24}$N$_4$O$_6$: C, 59.99; H, 5.49; N, 12.72. Found: C, 59.69; H, 5.59; N, 12.63.

Example 16

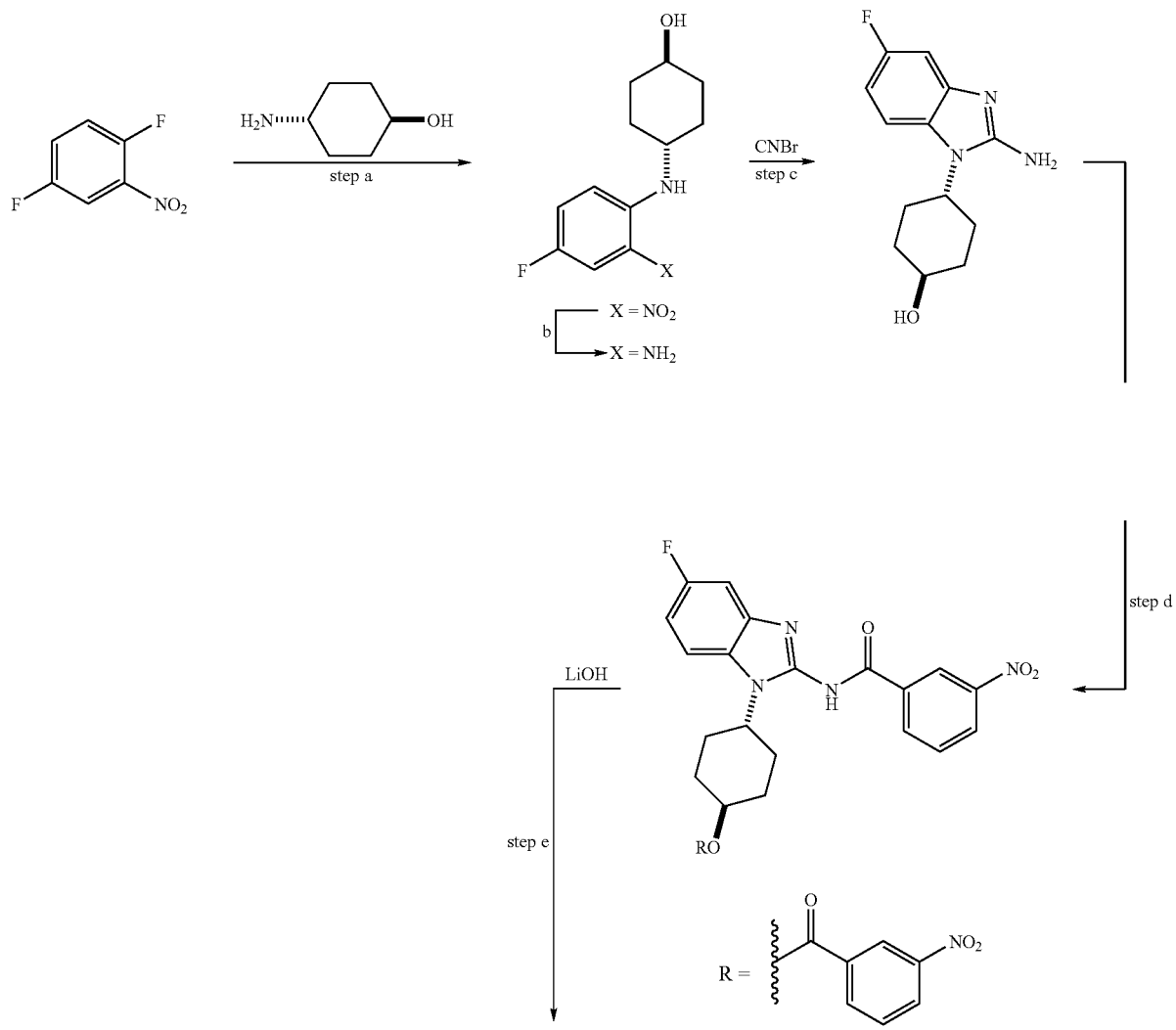

-continued

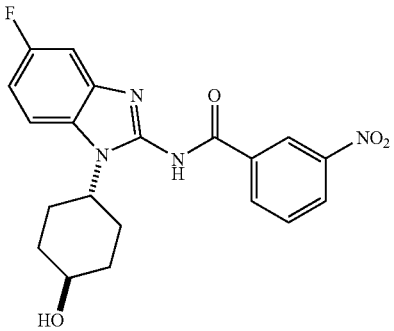

16

Synthesis of 3-nitro-N-(1-(trans-4-cyclohexanol-1-yl)-5-fluoro-1H-benzoimidazol-2-yl)-benzamide (16)

(a) 2-(trans-4-Cyclohexanol-1-yl)-4-fluoronitrobenzene: A flask was charged with 2.35 mL 2,5-difluoronitrobenzene (21.7 mmol, 1.0 equiv), followed by the slow addition of 2.5 g trans-1,4-cyclohexanolamine (21.7 mmol, 1.0 equiv). The slurry was then diluted with 3 mL $Et_2O$, and allowed to stir. After stirring for 12 h, the bright orange slurry was diluted with sat. $NaHCO_3$, extracted (3×$CH_2Cl_2$), washed (1×$H_2O$), dried ($Na_2SO_4$), and concentrated under reduced pressure. Purification by flash chromatography ($SiO_2$, 0-5% MeOH/$CH_2Cl_2$) gave 1.975 g of product 2-(trans-4-cyclohexanol-1-yl)-4-fluoronitrobenzene as a yellow solid (7.77 mmol).

(b) 2-(trans-4-Cyclohexanol-1-yl)-4-fluoroaniline: A nitrogen purged flask was charged with 1 g palladium on carbon (5 wt %), which was covered with 10 mL EtOH. 2-(trans-4-Cyclohexanol-1-yl)-4-fluoronitrobenzene (prepared above in step (a), 1.975 g, 7.77 mmol) was dissolved in 30 mL EtOH, and the solution was added to the catalyst suspension followed by the addition of 12 mL cyclohexene. The flask was equipped with a reflux condenser, and then placed into a preheated 80° C. bath. After stirring for 2 h, the solution was hot filtered through a plug of celite. The celite plug was washed (3×EtOH), and the combined EtOH fraction were concentrated under reduced pressure to give 1.58 g of the product as a tan solid (7.05 mmol).

(c) 2-Amino-1-(trans-4-cyclohexanol-1-yl)-5-fluorobenzimidazole: A 250 mL flask was charged with 30 mL $H_2O$ and 1.55 mL (7.75 mmol, 1.1 equiv) of a 5.0M solution of cyanogen bromide in $CH_3CN$. 2-(trans-4-Cyclohexanol-1-yl)-4-fluoroaniline (prepared above in step (b), 1.58 g, 7.05 mmol, 1.0 equiv) was dissolved in 20 mL MeOH, followed by addition over a period of 20 min via addition funnel to the cyanogen bromide solution. After stirring for 16 h, the solution was concentrated under reduced pressure to remove MeOH. The resulting aqueous solution was washed (2×EtOAc), and the EtOAc wash was back extracted 1×$H_2O$. The organics ware discarded, and the aqueous solution was made basic with sat. $NaHCO_3$. The slurry was then extracted (4×EtOAc), washed (1×brine), dried ($MgSO_4$), and concentrated under reduced pressure to give 1.31 g of the product 2-amino-1-(trans-4-cyclohexanol-1-yl)-5-fluorobenzimidazole as a tan solid (5.26 mmol). $^1$H NMR (DMSO-$d_6$, 400 MHz) δ 7.27 (dd, J=4.9, 8.7 Hz, 1H), 6.86 (dd, J=2.5, 10.1 Hz, 1H), 6.61 (m, 1H), 6.46 (s, 2H), 4.65 (s, 1H), 4.15 (m, 1H), 3.61 (m, 1H), 2.15 (m, 2H), 1.93 (m, 2H), 1.68 (, 2 H), 1.40 (m, 2H); MS: ESI(+) m/z 250.2 (M+H$^+$).

(d) 3-Nitro-N-(1-(trans-4-(3-nitrobenzoyl)cyclohexane-1-yl)-5-fluoro-1H-benzoimidazol-2-yl)-benzamide: 2-Amino-1-(trans-4-cyclohexanol-1-yl)-5-fluorobenzimidazole (879 mg, 3.525 mmol, 1.0 equiv, prepared above in step (c) was combined in a flask with 3.09 g O-benzotriazol-1-yl-N,N,N', N'-tetramethyluronium hexafluorophosphate (HBTU, 8.15 mmol, 2.31 equiv), 1.24 g 3-nitrobenzoic acid (7.42 mmol, 2.1 equiv), and 1.05 g 1-hydroxybenzotriazole hydrate (HOBT, 7.77 mmol, 2.2 equiv). 15 mL DMF was added, followed by 935 μL N-methylmorpholine (NMM, 8.50 mmol, 2.41 equiv). The resulting slurry was allowed to stir for 24 h, followed by the addition of a 10% solution of citric acid. The resulting slurry was extracted (3×EtOAc), washed (1×10% citric acid, 2×sat. $NaHCO_3$, 1×brine), dried ($MgSO_4$), and concentrated under reduced pressure. Purification by flash chromatography ($SiO_2$, 0-5% MeOH/$CH_2Cl_2$) gave the product as a yellow solid 1.16 g (2.12 mmol). $^1$H NMR (DMSO-$d_6$, 400 MHz) δ 12.95 (s, 1H), 8.95 (t, J=1.9 Hz, 1H), 8.69 (d, J=9.0 Hz, 1H), 8.67 (t, J=1.7 Hz, 1H), 8.53 (dd, J=2.3, 8.2 Hz, 1H), 8.43 (d, J=7.8 Hz, 1H), 8.39 (dd, J=1.5, 8.1 Hz, 1H), 7.92-7.79 (m, 3H), 7.40 (dd, J=2.6, 8.8 Hz, 1H), 7.13 (ddd, J=2.6, 9.1, 9.5 Hz, 1H), 5.30 (m, 1H), 5.0 (m, 1H), 2.65 (m, 2H), 2.28 (m, 2 H), 1.90 (m, 4H); MS: ESI(−) m/z 546.2 (M−H).

(e) 3-Nitro-N-(1-(trans-4-cyclohexanol-1-yl)-5-fluoro-1H-benzoimidazol-2-yl)-benzamide: The ester prepared above in step (d) (100 mg, 0.183 mmol) was combined with MeOH (10 mL), $H_2O$ (3 mL), and THF (3 mL) followed by the addition of 100 mg LiOH. The suspension was heated to 53° C. for 2 h, over which time the suspension slowly went into solution. At the end of 2 h, the solution was concentrated under reduced pressure, diluted with sat. $NaHCO_3$, and extracted 3×$CH_2Cl_2$. The solution was washed (2×sat. $NaHCO_3$), dried ($Na_2SO_4$), and concentrated under reduced pressure to give the product as a yellow solid 73 mg (0.183 mmol, quant.). $^1$H NMR (DMSO-$d_6$, 400 MHz) δ 12.97 (s, 1H), 8.98 (s, 1H), 8.60 (d, J=7.6 Hz, 1H), 8.38 (dd, J=2.0, 8.1 Hz, 1H), 7.79 (t, J=7.9 Hz, 1H), 7.94 (dd, J=4.5, 8.8 Hz, 1H), 7.35 (dd, J=2.4, 8.7 Hz, 1H), 7.11 (m, 1H), 4.77 (m, 2H), 3.72

(m, 1H), 2.01 (m, 2H), 1.80 (m, 2H), 1.49 (m, 2H); Anal. calcd for $C_{20}H_{19}FN_4O_4$: C, 60.30; H, 4.81; N, 14.06. Found: C, 60.11; H, 4.88; N, 13.97.

Example 17

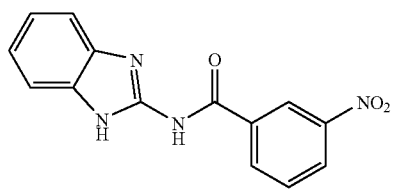

17

Synthesis of 2-benzylaminobenzimidazole (17). A 100 mL flask was charged with 1.0 g 2-aminobenzimidazole (7.51 mmol, 1.0 equiv), 1.13 g 3-nitrobenzaldehyde (7.51 mmol, 1.0 equiv), and 25 mL toluene. The flask was equipped with a Dean-Stark trap and reflux condenser and placed in a 110° C. bath. The solution was refluxed for 15.5 h, followed by the addition of 3 mL MeOH and 3 mL diisopropylethylamine. After refluxing an additional 29 h, the flask was removed, and the volatiles were removed under reduced pressure at 70° C. The remaining material was diluted with 50 mL MeOH, and cooled to 0° C. followed by the addition of 426 mg (11.27 mmol, 1.5 equiv) $NaBH_4$. After stirring for 3 h, the solution was concentrated under reduced pressure, and the residue was applied directly to a $SiO_2$ column (preflushed with 10% $MeOH/CH_2Cl_2$). The column was eluted with 10% $MeOH/CH_2Cl_2$ to give the product as an orange solid 320 mg (1.19 mmol). $^1H$ NMR (DMSO-$d_6$, 400 MHz) δ 11.0 (broad s, 1H), 8.25 (s, 1H), 8.11 (d, J=8.2 Hz, 1H), 7.85 (d, J=7.5 Hz, 1H), 7.62 (t, J=8.0 Hz, 1H), 7.34 (m, 1H), 7.13 (t, J=3.7 Hz, 2 H), 6.86 (s, 2H), 4.64 (d, J=5.8 Hz, 2H); MS: ESI(+) m/z 269.2 (M+H$^+$).

Example 18

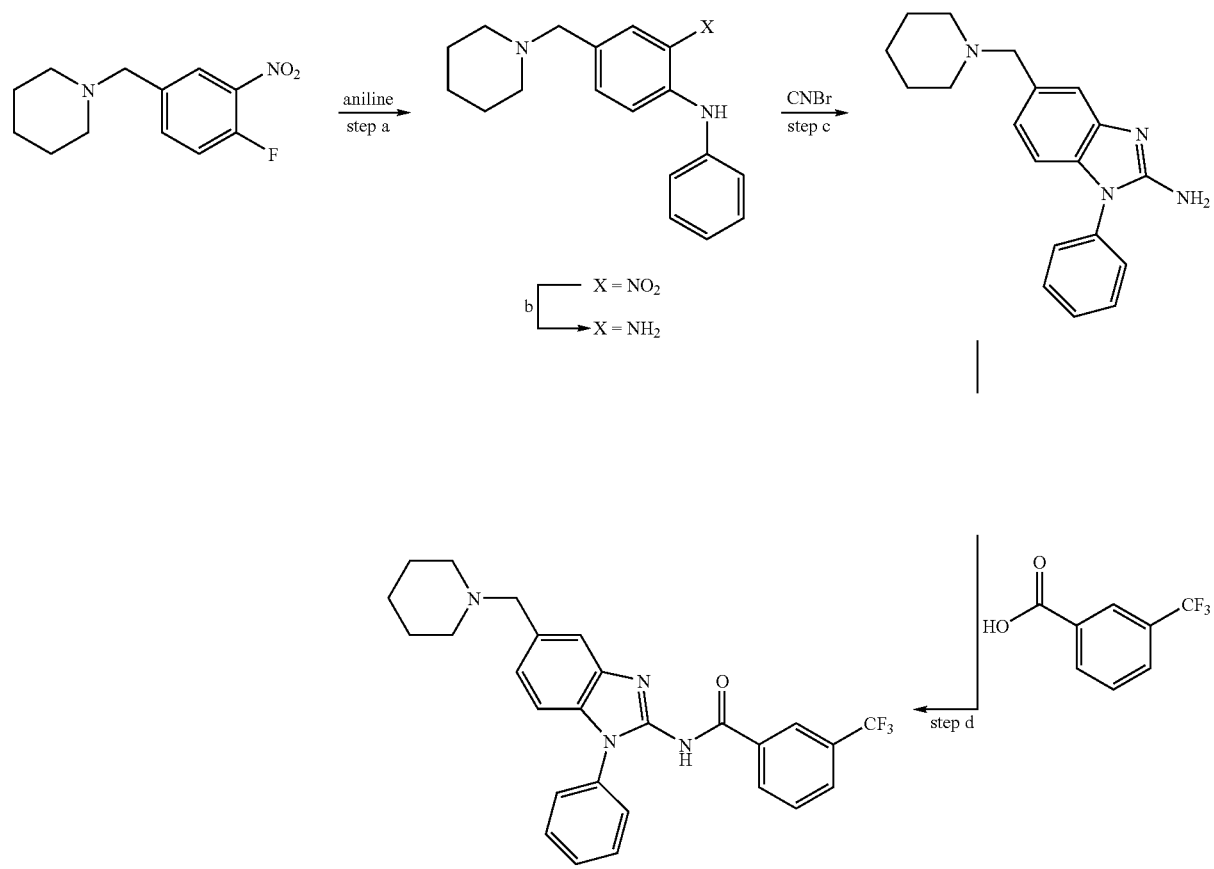

Synthesis of N-(1-Phenyl-5-piperidin-1-ylmethyl-1H-benzoimidazol-2-yl)-3-trifluoromethylbenzamide (36). (a) (2-Nitro-4-piperidin-1-ylmethyl-phenyl)phenyl-amine: To a 10 mL flask containing 1.3 mL N,N-diisopropylethylamine (7.5 mmol, 1.5 equiv) and 0.55 mL aniline (6.0 mmol, 1.2 equiv) was added 1.19 g 1-(4-fluoro-3-nitro-benzyl)-piperidine (5.0 mmol, 1.0 equiv). The flask was equipped with a reflux condenser, and heated to 150° C. After stirring for 15 h, the dark red solution was removed from the heating bath and allowed to cool to rt. The reaction was diluted with $CH_2Cl_2$ (20 mL) and sat. $NaHCO_3$ (50 mL). The aqueous solution was then extracted (3×$CH_2Cl_2$), dried ($MgSO_4$), and concentrated under reduced pressure. Purification by flash chromatography ($SiO_2$, 2-5% MeOH/$CH_2Cl_2$) gave the product N-(1-phenyl-5-piperidin-1-ylmethyl-1H-benzoimidazol-2-yl)-3-trifluoromethyl-benzamide as a reddish-orange oil (1.20 g, 3.85 mmol).

(b) N1-Phenyl-4-piperidin-1-ylmethyl-benzene-1,2-diamine: To a 200 mL flask containing 1.20 g (2-Nitro-4-piperidin-1-ylmethyl-phenyl)-phenyl-amine (3.85 mmol, 1.00 equiv), 15 mL EtOH, and 15 mL EtOAc was added 3.48 g $SnCl_2.2H_2O$ (15.4 mmol, 4.00 equiv). The flask was equipped with a reflux condenser, and heated to reflux temperature. After stirring for 4 h, the suspension was removed from the heating bath and allowed to cool to rt. The reaction was diluted with 50 mL sat. $NaHCO_3$ and 25 mL $CH_2Cl_2$. The aqueous solution was then extracted (3×$CH_2Cl_2$), and the combined organic layers were dried ($MgSO_4$), filtered, and concentrated under reduced pressure to give the product N1-phenyl-4-piperidin-1-ylmethyl-benzene-1,2-diamine as a yellow oil which was sufficiently pure to continue to the next step.

(c) 1-Phenyl-5-piperidin-1-ylmethyl-1H-benzoimidazol-2-ylamine: To a 25 mL flask containing 4 mL $H_2O$ and 1.16 mL of a 5.0 M solution of cyanogen bromide in $CH_3CN$ (5.78 mmol, 1.50 equiv) was carefully added a solution of N1-phenyl-4-piperidin-1-ylmethyl-benzene-1,2-diamine (<3.85 mmol, 1.00 equiv) in 4 mL MeOH via addition funnel over approximately five minutes. The reaction was allowed to stir for 16 h after which time the solution was concentrated under reduced pressure to remove most of the MeOH and the resulting acidic aqueous solution was diluted with 20 mL EtOAc and neutralized with 50 mL sat. $NaHCO_3$. The aqueous solution was then extracted (2×EtOAc), and the combined organic phases where washed with brine, dried ($MgSO_4$), filtered, and concentrated under reduced pressure to give the crude product 1-phenyl-5-piperidin-1-ylmethyl-1H-benzoimidazol-2-ylamine as a dark oil.

(d) N-(1-Phenyl-5-piperidin-1-ylmethyl-1H-benzoimidazol-2-yl)-3-trifluoromethyl-benzamide: To a 50 mL flask containing a solution of 2.28 g HBTU (2.3 mmol, 1.2 equiv), HOBT (2.3 mmol, 1.2 equiv), 0.43 g 3-trifluoromethyl benzoic acid (2.3 mmol, 1.2 equiv), 10 mL DMF, and 0.31 mL N-methylmorpholine (2.9 mmol, 1.5 equiv) was added a solution of 1-phenyl-5-piperidin-1-ylmethyl-1H-benzoimidazol-2-ylamine (<3.85 mmol, 1.0 equiv). The solution was allowed to stir for 16 h, after which time it was diluted with 20 mL EtOAc and 40 mL sat. $NaHCO_3$. The resulting aqueous solution was extracted (2×1:4 i-PrOH:EtOAc), and the combined organic layers were dried ($MgSO_4$), filtered, and concentrated under reduced pressure. Purification by flash chromatography ($SiO_2$, 2-5% MeOH/$CH_2Cl_2$) gave the product as a pale yellow solid (160 mg, 0.34 mmol, 18% from (2-nitro-4-piperidin-1-ylmethyl-phenyl)-phenylamine)). $^1H$ NMR (DMSO-$d_6$, 400 MHz) δ 13.00 (s, 1H), 8.31 (s, 1H), 8.28 (d, J=7.8 Hz, 1H), 7.85 (d, J=7.8 Hz, 1H), 7.69 (m, 5H), 7.59 (m, 2H), 7.17 (m, 2H), 3.33 (s, 2H), 2.35 (s, 4H), 1.50 (s, 4H), 1.40 (s, 2H).

Example 19

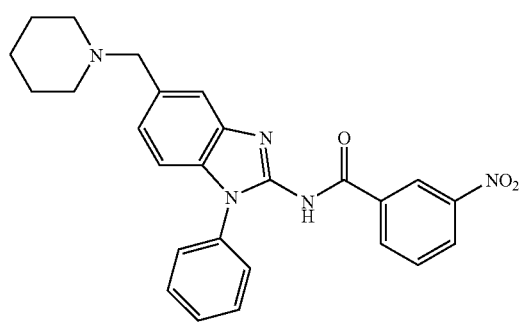

35

Synthesis of N-(1-Phenyl-5-piperidin-1-ylmethyl-1H-benzoimidazol-2-yl)-3-nitro-benzamide (35). Using the methods described above in Example 18 the following compound was prepared substituting 3-nitrobenzoic acid for 3-trifluromethylbenzoic acid in step (d): N-(1-Phenyl-5-piperidin-1-ylmethyl-1H-benzoimidazol-2-yl)-3-nitrobenzamide: $^1H$ NMR (DMSO-$d_6$, 400 MHz) δ 13.85 (s, 1H), 9.58 (s, 1H), 9.20 (d, J=7.8 Hz, 1H), 9.13 (d, J=7.9 Hz, 1H), 8.52 (m, 5H), 8.40 (m, 2H), 7.97 (m, 2H), 4.31 (s, 2H), 3.15 (s, 4H), 2.31 (s, 4H), 2.20 (s, 2H).

Example 20

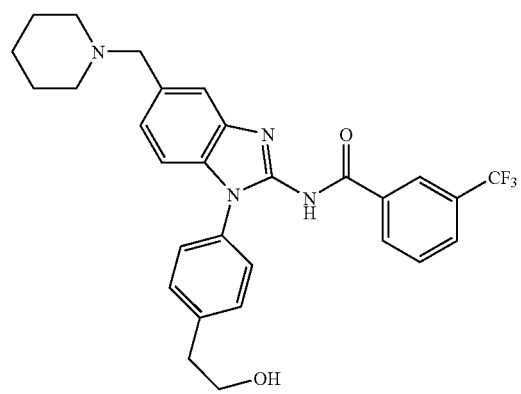

37

Synthesis of N-{1-[4-(2-Hydroxy-ethyl)-phenyl]-5-piperidin-1-ylmethyl-1H-benzoimidazol-2-yl}-3-trifluoromethylbenzamide (37). Using the methods described above in Example 18, and substituting 4-aminophenethylalcohol for aniline, the following was prepared: N-{1-[4-(2-hydroxy-ethyl)-phenyl]-5-piperidin-1-ylmethyl-1H-benzoimidazol-2-yl}-3-trifluoromethylbenzamide: $^1H$ NMR (DMSO-$d_6$, 400 MHz) δ 13.08 (s, 1H), 8.32 (s, 1H), 8.29 (d, J=8.0 Hz, 1H), 7.85 (d, J=7.4 Hz 1H), 7.69 (t, J=8.0 Hz, 1H), 7.60 (t, J=8.0 Hz, 1H), 7.50 (d, J=7.8 Hz, 3H), 7.17 (m, 2H), 4.77 (t, J=5.0 Hz, 1H), 3.71 (q, J=6.3 Hz, 2H), 3.50 (s, 2H), 2.87 (t, J=6.8 Hz, 2H), 2.34 (s, 4H), 1.50 (s, 4H), 1.40 (s, 2H).

Example 21

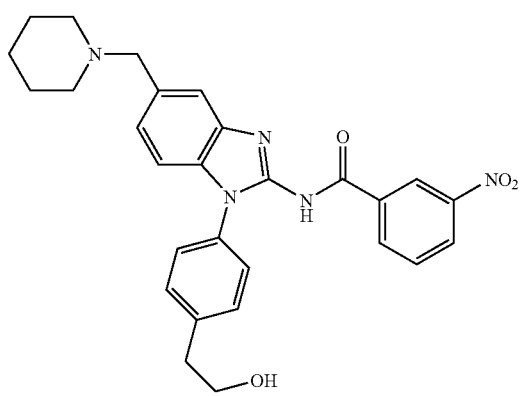

Synthesis of N-{1-[4-(2-Hydroxy-ethyl)-phenyl]-5-piperidin-1-ylmethyl-1H-benzoimidazol-2-yl}-3-nitrobenzamide (38). Using the same method as Example 18, and substituting 4-aminophenethylalcohol for aniline and substituting 3-nitrobenzoic acid for 3-trifluoromethylbenzoic acid, the following was prepared: N-{1-[4-(2-Hydroxy-ethyl)-phenyl]-5-piperidin-1-ylmethyl-1H-benzoimidazol-2-yl}-3-nitrobenzamide: $^1$H NMR (DMSO-$d_6$, 400 MHz) δ 13.10 (s, 1H), 8.80 (s, 1H), 8.42 (d, J=7.8 Hz, 1H), 8.34 (d, J=8.0 Hz, 1H), 7.75 (t, J=7.8 Hz, 1H), 7.67 (d, J=8.0 Hz, 2H), 7.62 (d, J=8.6 Hz, 1H), 7.53 (d, J=8.6 Hz, 2H), 7.20 (m, 2H), 4.79 (t, J=5.2 Hz, 1H), 3.74 (q, J=6.2 Hz, 2H), 3.53 (s, 2H), 2.91 (t, J=7.2 Hz, 2H), 2.36 (s, 4H), 1.53 (s, 4H), 1.42 (s, 2H).

Example 22

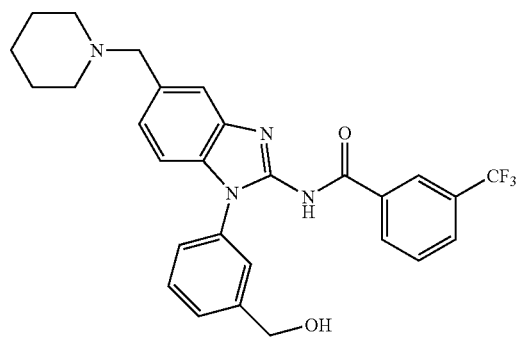

Synthesis of N-[1-(3-Hydroxymethyl-phenyl)-5-piperidin-1-ylmethyl-1H-benzoimidazol-2-yl]-3-trifluoromethylbenzamide (70). Using the same method as Example 18, and substituting 3-aminobenzyl alcohol for aniline, the following was prepared: N-[1-(3-Hydroxymethyl-phenyl)-5-piperidin-1-ylmethyl-1H-benzoimidazol-2-yl]-3-trifluoromethyl-benzamide: $^1$H NMR (CDCl$_3$, 400 MHz) δ 12.50 (s, 1H), 8.47 (s, 1H), 8.35 (d, J=7.8 Hz, 1H), 7.70 (s, 1H), 7.67 (d, J=7.7 Hz, 1H), 7.43-7.61 (m, 4H), 7.39 (s, 1H), 7.21 (m, 2H), 4.85 (s, 2H), 3.57 (s, 2H), 2.60 (s, 1H), 2.43 (s, 4H), 1.63 (m, 4H), 1.45 (s, 2H).

Example 23

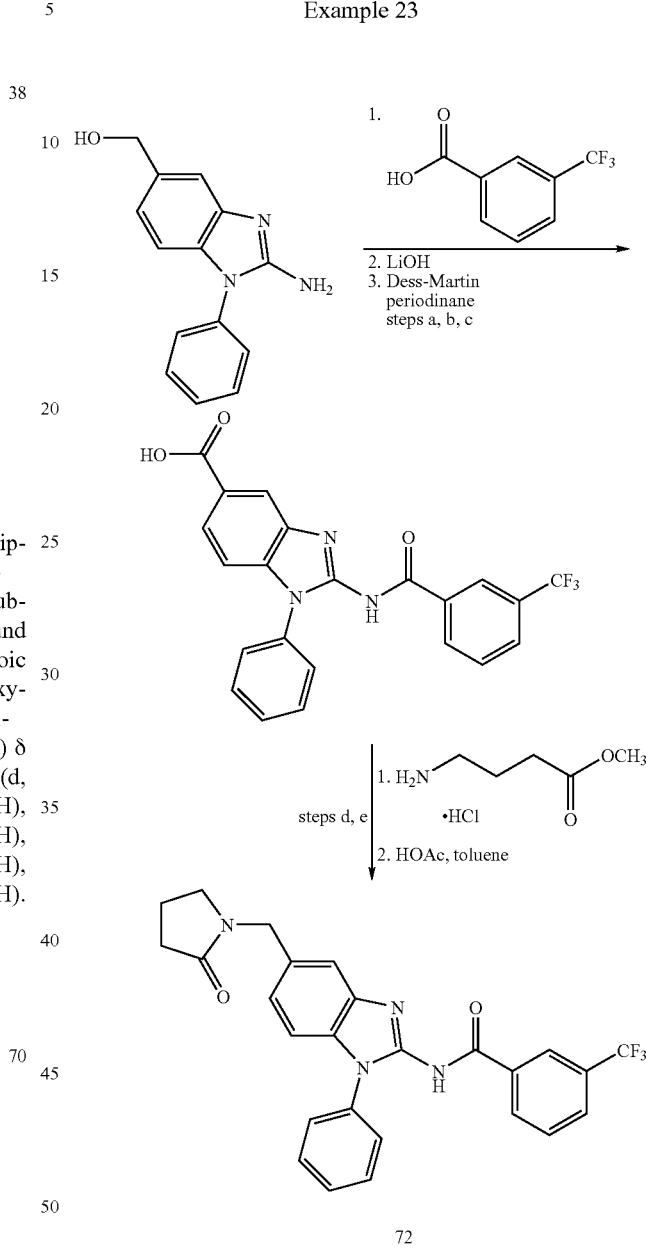

N-[5-(2-Oxo-pyrrolidin-1-ylmethyl)-1-phenyl-1H-benzoimidazol-2-yl]-3-trifluoromethylbenzamide (72). Using the same methods as in Example 18, and substituting (4-fluoro-3-nitro-phenyl)methanol for (2-Nitro-4-piperidin-1-ylmethyl-phenyl)phenylamine the following was prepared: N-(5-Formyl-1-phenyl-1H-benzoimidazol-2-yl)-3-trifluoromethylbenzamide.

Steps (a), (b), (c) A solution of 15.1 g of 2-amino-1-phenyl-5-(hydroxymethyl)benzimidazole (63.0 mmol, 1.0 equiv) in 100 mL DMF was added to a 1000 mL flask containing a stirred solution of 56.51 g HBTU (151 mmol, 2.4 equiv), 20.44 g HOBT (151 mmol, 2.4 equiv), 28.7 g 3-trifluoromethyl benzoic acid (151 mmol, 2.4 equiv), 210 mL DMF, and 20.8 mL N-methylmorpholine (189 mmol, 3.0 equiv). The solution was allowed to stir for 16 h, at which time 1.5 L 10% aq. citric acid was added. The resulting mixture was stirred for an additional 2 h, then the mixture was filtered, and washed (2×sat. NaHCO$_3$, then H$_2$O). The mauve product was dissolved in a solution of 800 mL THF, 150 mL MeOH, 50 mL H$_2$O, and 7.54 g LiOH (315 mmol, 5.00 equiv). The resulting brown mixture was heated to 50° C. for 1 h, then allowed to cool to rt, at which time the reaction mixture was diluted with 300 mL sat. NaHCO$_3$ and 100 mL EtOAc. The aqueous solution was extracted (2×EtOAc), and the combined organic layers were then washed with brine, dried (MgSO$_4$), filtered, and concentrated under reduced pressure. The resulting brown solid was redissolved in a 5 L flask containing 3.5 L THF. 25.0 g Dess-Martin periodinane (59 mmol, 1.10 equiv) was then added and the reaction was allowed to stir 1 h. The solution was diluted with 500 mL sat. NaHCO$_3$ and 200 mL EtOAc. The aqueous layer was extracted (2×EtOAc) and the combined organic layers were washed with brine, dried (MgSO$_4$), filtered, and concentrated under reduced pressure. Purification by flash chromatogra- 20 h, after which time the resulting brown solution was diluted with 50 mL sat. NaHCO$_3$ and 50 mL EtOAc. The aqueous layer was extracted (2×EtOAc) and the combined organic layers were washed with brine, dried (MgSO$_4$), filtered, and concentrated under reduced pressure. Purification by flash chromatography (SiO$_2$, 1-2% MeOH/CH$_2$Cl$_2$ with 1% aq. NH$_4$OH) gave 300 mg of the product as a colorless solid (0.57 mmol). A solution of 105 mg of this product (0.20 mmol, 1.00 equiv) in 20 mL toluene and 2 mL HOAc was heated to reflux temperature for 1 h. The solution was concentrated under reduced pressure and purified by flash chromatography (SiO$_2$, 2-5% MeOH/CH$_2$Cl$_2$ with 1% aq. NH$_4$OH) to give 80 mg of the product as a colorless solid (0.17 mmol). $^1$H NMR (CDCl$_3$, 400 MHz) δ 13.03 (s, 1H), 8.31 (s, 1H), 8.28 (d, J=7.8 Hz, 1H), 7.85 (d, J=7.7 Hz, 1H), 7.65-7.75 (m, 5H), 8.26 (t, J=7.1 Hz, 1H), 7.53 (s, 1H), 7.16 (m, 2H), 4.47 (s, 2H), 3.26 (t, J=7.0 Hz, 2H), 2.31 (t, J=8.0 Hz, 2H), 1.94 (m, 2H).

Example 24

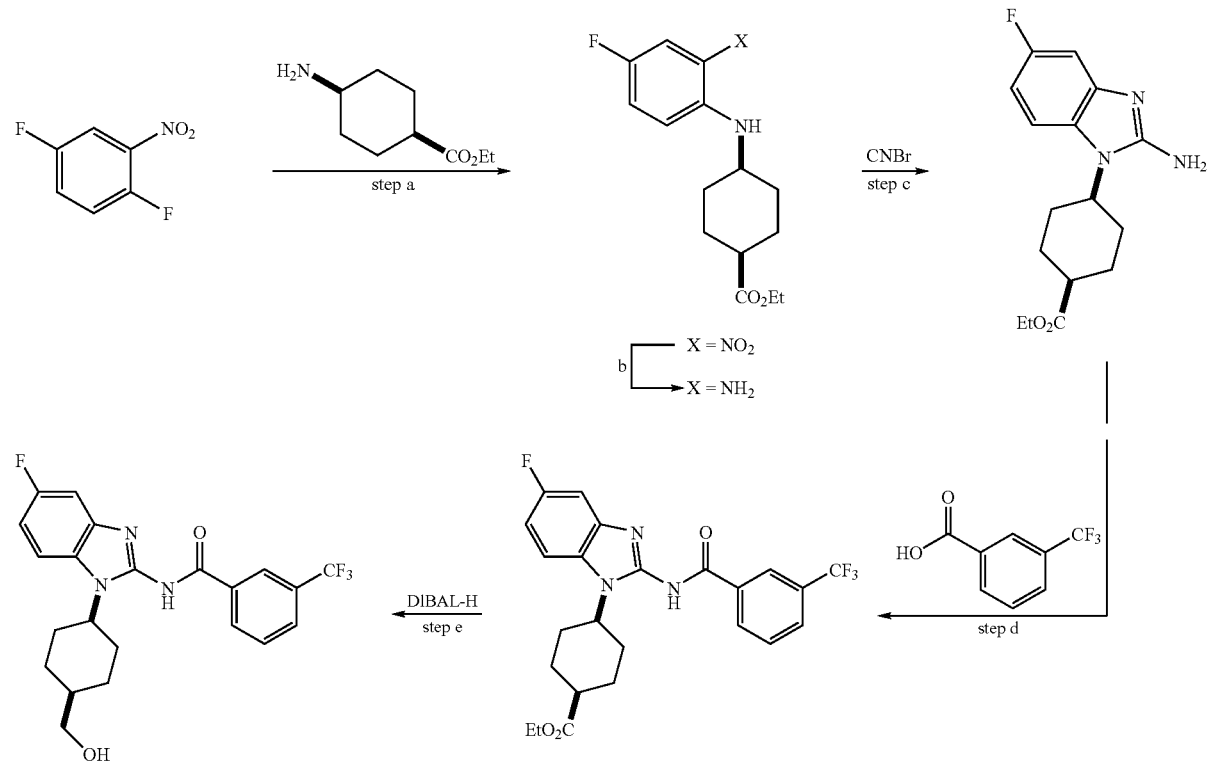

phy (SiO$_2$, 1-2% MeOH/CH$_2$Cl$_2$) gave 8.0 g of the product as a tan solid (19 mmol). $^1$H NMR (DMSO-d$_6$, 400 MHz) δ 13.28 (s, 1H), 10.03 (s, 1H), 8.29 (m, 2 H), 8.10 (s, 1H), 7.85 (m, 2H), 7.60-7.75 (m, 6H), 7.36 (d, J=8.1 Hz, 1H).

(d) and (e) To a suspension of 409 mg N-(5-Formyl-1-phenyl-1H-benzoimidazol-2-yl)-3-trifluoromethylbenzamide (1.00 mmol, 1.00 equiv) prepared above in Example 7 in 40 mL of 1:9 HOAc:MeOH, 0.205 g NaOAc (2.50 mmol, 2.50 equiv), and 0.84 g ethyl 4-aminobutyrate hydrochloride (5.00 mmol, 5.00 equiv) was added 0.138 g NaCNBH$_3$ (2.00 mmol, 2.00 equiv). The pink suspension was allowed to stir Synthesis of N-[5-fluoro-1-(cis-4-hydroxymethyl-cyclohexyl)-1H-benzoimidazol-2-yl]-3-trifluoromethyl-benzamide (65). (a) cis-4-(4-fluoro-2-nitro-phenylamino)-cyclohexanecarboxylic acid ethyl ester: A 250 mL flask was charged with 12.74 g 2,5-difluoronitrobenzene (80.1 mmol, 1.0 equiv), 13.70 g cis-4-amino-cyclohexanecarboxylic acid ethyl ester (80.1 mmol, 1.0 equiv), 27.9 mL diisopropylethylamine (2.0 equiv). The flask was equipped with a reflux condenser, and then placed into a preheated 85° C. bath. After stirring for 4 h, the red solution was diluted with sat. NaHCO$_3$, extracted (2×EtOAc), washed (1×brine), dried ($Na_2SO_4$) and concentrated under reduced pressure. Purification by flash chromatography ($SiO_2$, 15% EtOAc/hexane) gave 7.5 g of product cis-4-(4-fluoro-2-nitro-phenylamino)-cyclohexanecarboxylic acid ethyl ester as a red solid (24.0 mmol).

(b) cis-4-(2-amino-4-fluoro-phenylamino)-cyclohexanecarboxylic acid ethyl ester: To a 250 mL flask containing 0.5 g of palladium on carbon (5 wt %), 1.5 g cis-4-(4-fluoro-2-nitro-phenylamino)-cyclohexanecarboxylic acid ethyl ester (4.84 mmol, 1.0 equiv) and 25 mL EtOH under $N_2$ was added 3.5 mL cyclohexene. The flask was equipped with a reflux condenser, and then placed into a preheated 90° C. bath. After stirring for 24 h, the suspension was removed from the heating bath and then allowed to go through a celite pad to remove the catalyst. The celite pad was washed (5×EtOH). The combined organics were concentrated under reduced pressure to give 1.3 g of the product as a brown solid which was sufficiently pure to continue to the next step (4.64 mmol).

(c) cis-4-(2-amino-5-fluoro-benzoimidazol-1-yl)-cyclohexanecarboxylic acid ethyl ester: A 250 mL flask was charged with 15 mL $H_2O$, followed by the addition of 0.63 mL, 5.0 M solution of cyanogen bromide in $CH_3CN$. The cis-4-(2-amino-4-fluoro-phenylamino)-cyclohexanecarboxylic acid ethyl ester (2.86 mmol, 1.0 equiv) was dissolved in 25 mL MeOH, and was introduced via addition funnel over a period of 30 min to the cyanogen bromide solution. After stirring for 24 h, the solution was concentrated under reduced pressure to remove MeOH, and the resulting acidic aqueous solution was diluted with sat. $NaHCO_3$. The slightly basic aqueous solution was then extracted (EtOAc), washed (1×brine), dried ($Na_2SO_4$) and concentrated under reduced pressure to give 0.82 g of the product as a brown solid (2.69 mol).

(d) cis-4-(5-fluoro-2-(3-trifluoromethyl-benzoylamino)-benzoimidazol-1-yl)-cyclohexanecarboxylic acid ethyl ester: 305 mg cis-4-(2-amino-5-fluoro-benzoimidazol-1-yl)-cyclohexanecarboxylic acid ethyl ester (1.0 mmol, 1.0 equiv) was combined in a flask with 569 mg O-benzotriazol-1-yl-N,N,N',N'-tetramethyluronium hexafluorophosphate (HBTU, 1.5 mmol, 1.5 equiv), 285 mg 3-trifluoromethylbenzoic acid (1.5 mmol, 1.5 equiv) and 203 mg 1-hydroxybenzotriazole hydrate (HOBT, 1.5 mmol, 1.5 equiv), followed by the addition of 12 mL DMF and 165 µL N-methylmorpholine (NMM, 1.5 mmol, 1.5 equiv). The solution was allowed to stir for 24 h and then diluted with sat. $NaHCO_3$. The solution was extracted (2×EtOAc), washed (1×brine), dried ($Na_2SO_4$) and concentrated under reduced pressure. Purification by flash chromatography ($SiO_2$, 20% EtOAc/hexane) gave 0.39 g of the product as a tan solid (0.82 mmol).

(e) N-[5-fluoro-1-(cis-4-hydroxymethyl-cyclohexyl)-1H-benzoimidazol-2-yl]-3-trifluoromethyl-benzamide: To a 100 mL flask containing 0.18 g cis-4-(5-fluoro-2-(3-trifluoromethyl-benzoylamino)-benzoimidazol-1-yl)-cyclohexanecarboxylic acid ethyl ester (0.4 mmol, 1.0 equiv) and 20 mL THF was carefully added 2.0 mL of 1.0 M DIBAL-H in toluene. The reaction was allowed to stir for 1 h at which it was diluted with 1 N HCl. The solution was then extracted (2×EtOAc), washed (1×brine), dried ($Na_2SO_4$) and concentrated under reduced pressure. Purification by flash chromatography ($SiO_2$, 60% EtOAc/hexane) gave 0.1 g of product as a white solid (0.23 mmol). $^1$H NMR ($CDCl_3$, 400 MHz) 12.80 (s, 1H), 8.62 (s, 1H), 8.50 (d, J=7.3 Hz, 1H), 7.79 (d, J=7.3 Hz, 1H), 7.62 (t, J=7.3 Hz, 1H), 7.35 (dd, J=4.3, 8.6 Hz, 1H), 7.12 (dd, J=3.4, 8.6 Hz, 1H), 7.03 (ddd, J=3.4. 3.4, 8.6 Hz, 1H), 4.70 (m, 1H), 3.99 (d, J=8.2 Hz, 2H), 2.60 (m, 2H), 2.10 (m, 3H), 1.80 (m, 4H).

Example 25

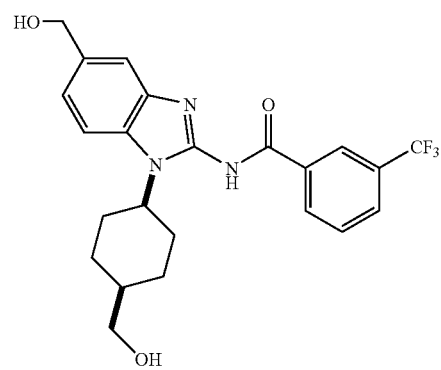

66

Synthesis of N-[5-fluoro-1-(cis-4-hydroxymethyl-cyclohexyl)-1H-benzoimidazol-2-yl]-3-trifluoromethylbenzamide (66). Using the methods described above as in Example 24, and substituting (4-fluoro-3-nitrophenyl)-methanol (prepared as in Example 29) for 2,5-difluoronitrobenzene in step (a), the following was prepared: N-[5-fluoro-1-(cis-4-hydroxymethyl-cyclohexyl)-1H-benzoimidazol-2-yl]-3-trifluoromethylbenzamide: $^1$H NMR (DMSO-$d_6$, 400 MHz) 12.90 (s, 1H), 8.50 (d, J=7.6 Hz, 1H), 8.47 (s, 1H), 7.91 (d, J=7.6 Hz, 1H), 7.76 (t, J=7.6 Hz, 1H), 7.57 (s, 1H), 7.55 (d, J=8.4 Hz, 1H), 7.23 (d, J=8.4 Hz, 1H), 5.28 (broad s, 1H), 4.65 (m, 1H), 4.58 (m, 1H), 4.57 (s, 2H), 3.5 (d, J=7.3 Hz, 2H), 2.52 (m, 2H), 1.94 (m, 3H), 1.65 (m, 4H).

Example 26

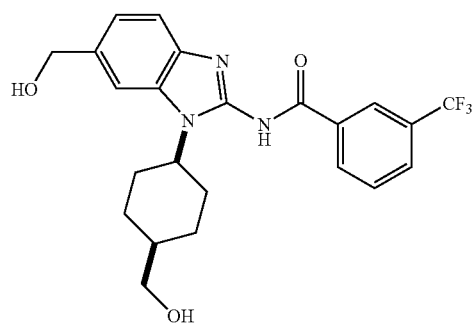

53

Synthesis of N-[6-hydroxymethyl-1-(cis-4-hydroxymethyl-cyclohexyl)-1H-benzoimidazol-2-yl]-3-trifluoromethylbenzamide (53). Using the methods described above, and substituting (3-fluoro-4-nitrophenyl)-methanol for 2,5-difluoronitrobenzene in step (a) the following was prepared: N-[6-hydroxymethyl-1-(cis-4-hydroxymethyl-cyclohexyl)-1H-benzoimidazol-2-yl]-3-trifluoromethylbenzamide: $^1$H NMR (DMSO-$d_6$, 400 MHz) 12.95 (s, 1H), 8.53 (d, J=7.6, 1H), 8.47 (s, 1H), 7.92 (d, J=7.6 Hz, 1H), 7.78 (t, J=7.6 Hz, 1H), 7.58 (s, 1H), 7.54 (d, J=8.2 Hz, 1H), 7.20 (d, J=8.2 Hz, 1H), 4.78 (m, 1H), 4.65 (s, 2H), 3.72 (d, J=8.1, Hz, 2H), 2.50 (m, 2H), 1.95 (m, 3H), 1.70 (m, 4H).

Example 27

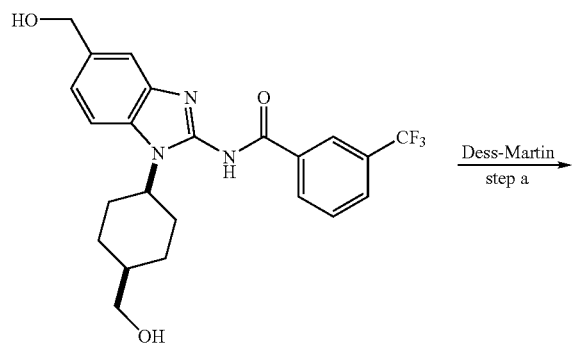

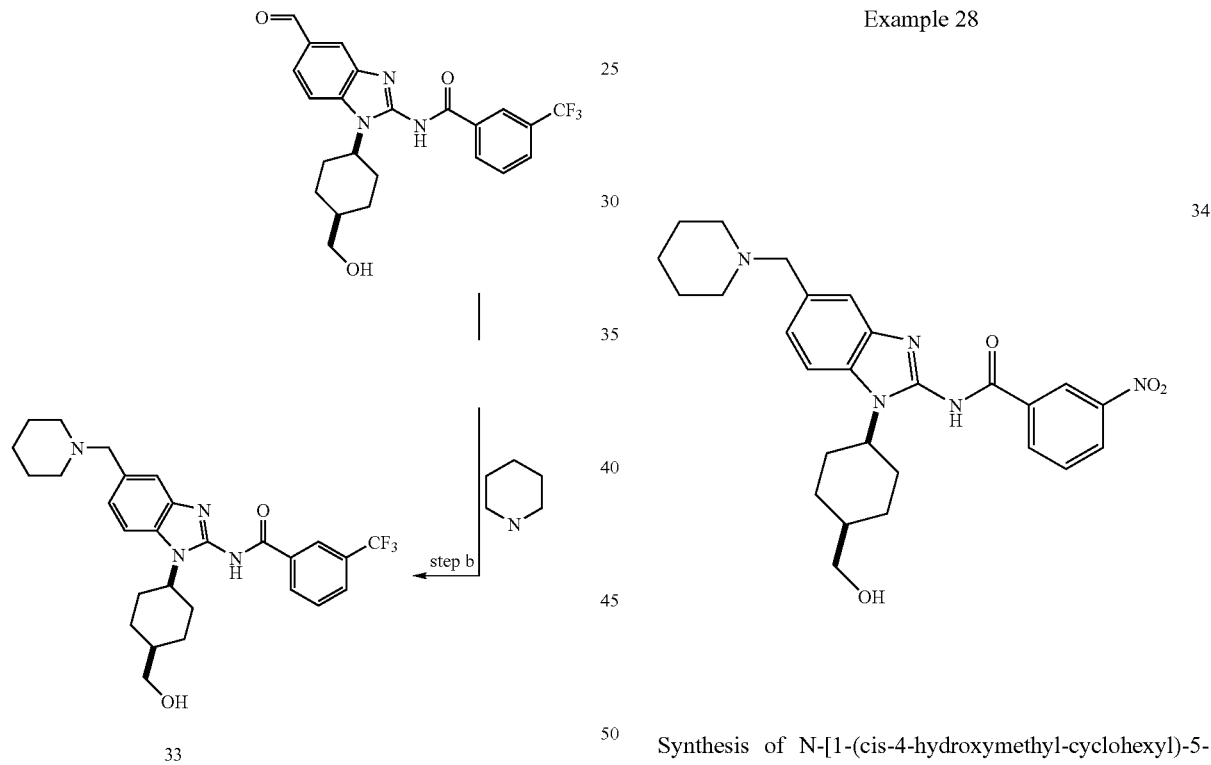

Synthesis of N-[1-(cis-4-hydroxymethyl-cyclohexyl)-5-piperidin-1-yl-methyl-1H-benzoimidazol-2-yl]-3-trifluoromethylbenzamide (33). (a) N-[5-formyl-1-(cis-4-hydroxymethyl-cyclohexyl)-1H-benzoimidazol-2-yl]-3-trifluoromethyl-benzamide: To a 100 mL flask containing 50 mg N-[5-hydroxymethyl-1-(cis-4-hydroxymethyl-cyclohexyl)-1H-benzoimidazol-2-yl]-3-trifluoromethyl-benzamide (0.117 mmol, 1.0 equiv) and 20 mL THF was added 49.6 mg Dess-Martin reagent (0.117 mmol, 1.0 equiv). After stirring for 30 min, the suspension was diluted with sat. NaHCO₃, extracted (2×10% MeOH/CH₂Cl₂), washed (1×brine), dried (Na₂SO₄) and concentrated under reduced pressure. Purification by flash chromatography (SiO₂, 5% MeOH/CH₂Cl₂) gave 30 mg of the product as white solid (0.07 mmol).

(b) N-[1-(cis-4-hydroxymethyl-cyclohexyl)-5-piperidin-1-yl-methyl-1H-benzoimidazol-2-yl]-3-trifluoromethyl-benzamide: To a 1 L flask containing 50 mg N-[5-formyl-1-(cis-4-hydroxymethyl-cyclohexyl)-1H-benzoimidazol-2-yl]-3-trifluoromethyl-benzamide (0.118 mmol, 1.0 equiv), 8 mL 1,2-dichloroethane and 0.3 mL AcOH was added 50 mg piperidine (0.59 mol, 5.0 equiv) and 50 mg NaBH(OAc)₃ (0.236 mmol, 2.0 equiv). After stirring for 12 h, the reaction was diluted with sat. NaHCO₃, extracted (2×10% MeOH/CH₂Cl₂), dried (Na₂SO₄) and concentrated under reduced pressure to give 35 mg of the product as a yellow liquid (0.07 mmol). $^1$H NMR (CD₃OD, 400 MHz) 8.55 (s, 1H), 8.54 (d, J=8.5 Hz, 1H), 7.86 (d, J=8.5 Hz, 1H), 7.75 (t, J=8.5 Hz, 1H), 7.60 (d, J=6.5 Hz, 1H), 7.55 (s, 1H), 7.30 (d, J=6.5 Hz, 1H), 4.95 (m, 1H), 3.91 (d, J=6.8 Hz, 1H), 3.63 (s, 2H), 2.65 (m, 2H), 2.50 (m, 4H), 2.10 (m, 4H), 1.55 (m, 9H).

Example 28

Synthesis of N-[1-(cis-4-hydroxymethyl-cyclohexyl)-5-piperidin-1-yl-methyl-1H-benzoimidazol-2-yl]-3-nitrobenzamide (34). Using the methods described above as in Example 27, and substituting N-[5-hydroxymethyl-1-(cis-4-hydroxymethyl-cyclohexyl)-1H-benzoimidazol-2-yl]-3-nitro-benzamide for N-[5-hydroxymethyl-1-(cis-4-hydroxymethyl-cyclohexyl)-1H-benzoimidazol-2-yl]-3-trifluorobenzamide in step (a) the following was prepared: N-[1-(cis-4-hydroxymethyl-cyclohexyl)-5-piperidin-1-yl-methyl-1H-benzoimidazol-2-yl]-3-nitrobenzamide: $^1$H NMR (CD₃OD, 400 MHz) 9.10 (d, J=8.4 Hz, 1H), 8.67 (d, J=8.4 Hz, 1H), 8.40 (d, J=8.4 Hz, 1H), 7.75 (t, J=8.4 Hz, 1H), 7.58 (d, J=6.3 Hz, 1H), 7.55 (s, 1H), 7.33 (d, J=6.3 Hz, 1H), 4.95 (m, 1H), 3.94 (d, J=8.1 Hz, 1H), 3.65 (s, 2H), 2.70 (m, 2H), 2.55 (m, 4H), 2.10 (m, 3H), 1.80 (m, 3H), 1.65 (m, 5H), 1.55 (m, 2H).

Example 29

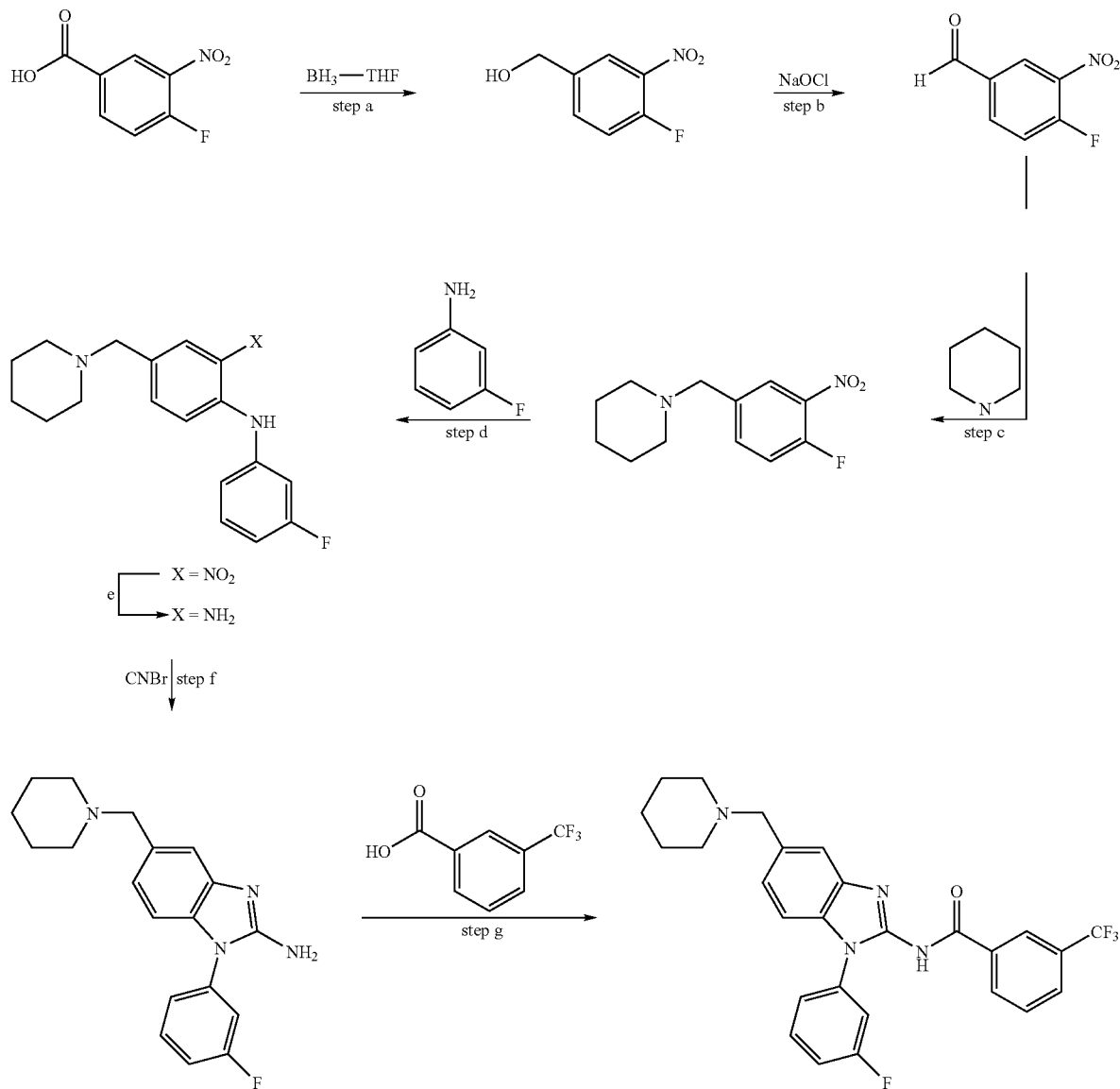

Synthesis of N-[1-(3-fluorophenyl)-5-piperidin-1-ylmethyl-1H-benzoimidazol-2-yl]-3-trifluoromethylbenzamide (68). (a) (4-Fluoro-3-nitrophenyl)-methanol: To a 2 L flask containing 75.0 g 4-fluoro-3-nitrobenzoic acid (405.4 mmol, 1.0 equiv) was carefully added 668.2 ml of 1.0 M $BH_3$-THF in 100 mL THF over 2 h via addition funnel. The reaction was allowed to stir for 2 h at which time it was diluted with sat. $NaHCO_3$ and extracted (2×EtOAc). The EtOAc solution was then washed (1×brine), dried ($Na_2SO_4$), and concentrated under reduced pressure to give 6.24 g of the product as a yellow solid (364.9 mmol).

(b) 4-fluoro-3-nitro-benzaldehyde: A 2 L flask was charged with 8.0 g (4-fluoro-3-nitrophenyl)-methanol (46.8 mmol, 1.0 equiv), 450 mL $CH_2Cl_2$ and 450 mL $CHCl_3$. The solution was cooled to 0° C., and added 80 mL of a 0.5 M potassium bromide in $H_2O$ and 900 mg tempo, followed by NaOCl solution prepared from 700 mL bleach, 700 mL $H_2O$ and 58 g $NaHCO_3$. After stirring for 30 min, the solution was diluted with sat. $NaHCO_3$ and extracted (2×$CH_2Cl_2$). The $CH_2Cl_2$ solution was then dried ($Na_2SO_4$) and concentrated under reduced pressure to give 7.2 g of the product as a brown solid (42.6 mmol).

(c) 1-(4-fluoro-3-nitrobenzyl)-piperidine: To a 1 L flask containing 24.0 g 4-fluoro-3-nitrobenzaldehyde (142.0 mmol, 1.0 equiv), 400 mL 1,2-dichloroethane and 30 mL AcOH (426.0 mmol, 3.0 equiv) was carefully added a solution of 16.8 mL piperidine (170.4 mmol, 1.2 equiv) in 100 mL 1,2-dichloroethane via a addition funnel over a period of 1 h at 0° C., and then NaBH(OAc)$_3$ (586.0 mmol, 4.0 equiv). After stirring for 12 h, the reaction was acidified (1 N HCl) and washed (2×hexane). The aqueous layer was then basified (solid NaOH), extracted (2×10% MeOH/CH$_2$Cl$_2$), dried (Na$_2$SO$_4$) and concentrated under reduced-pressure to give 19.36 g of the product as a yellow liquid (81.3 mmol).

(d) (3-fluorophenyl)-(2-nitro-4-piperidin-1-ylmethylphenyl) amine: A 250 mL flask was charged with 2.38 g 1-(4-fluoro-3-nitrobenzyl)-piperidine (10.0 mmol, 1.0 equiv), 2.22 g 3-fluoroaniline (20.0 mmol, 2.0 equiv), 3.5 mL diisopropylethylamine (2.0 equiv) and 5 mL DMF. The flask was equipped with a reflux condenser, and then placed into a preheated 140° C. bath. After stirring for 12 h, the red solution was diluted with sat. NaHCO$_3$, extracted (2×10% MeOH/CH$_2$Cl$_2$), washed (1×brine), dried (Na$_2$SO$_4$) and concentrated under reduced pressure. Purification by flash chromatography (SiO$_2$, 5% MeOH/CH$_2$Cl$_2$) gave 1.8 g of product (3-fluorophenyl)-(2-nitro-4-piperidin-1-ylmethylpheny) amine as a red solid (5.47 mmol).

(e) N$^1$-(3-fluorophenyl)-4-piperidin-1-ylmethyl-benzene-1,2-diamine: To a 250 mL flask containing 1.8 g (3-fluorophenyl)-(2-nitro-4-piperidin-1-ylmethylphenyl) amine (5.47 mmol, 1.0 equiv), 20 mL EtOH and 20 mL EtOAc was added 4.92 g SnCl$_2$.H$_2$O (21.9 mmol, 4.0 equiv). The flask was equipped with a reflux condenser, and then placed into a preheated 90° C. bath. After stirring for 12 h, the solution was diluted with sat. NaHCO$_3$ and the resulting suspension was then filtered through a pad of celite to remove white precipitate. The celite pad was washed (2×30% (CH$_3$)$_2$CHOH/CH$_2$Cl$_2$). The solution was extracted (2×30% (CH$_3$)$_2$CHOH/CH$_2$Cl$_2$), washed (1×brine), dried (Na$_2$SO$_4$) and concentrated under reduced pressure to give 1.57 g of the product as a brown solid (5.25 mmol).

(f) 1-(3-Fluorophenyl)-5-piperidin-1-ylmethyl-1H-benzoimidazol-2-ylamine: A 250 mL flask was charged with 15 mL H$_2$O, followed by the addition of 1.15 mL of a 5.0 M solution of cyanogen bromide in CH$_3$CN. The N$^1$-(3-fluorophenyl)-4-piperidin-1-ylmethyl-benzene-1,2-diamine prepared above (5.25 mmol, 1.0 equiv) was dissolved in 25 mL MeOH, and was introduced via addition funnel over a period of 30 min to the cyanogen bromide solution. After stirring for 24 h, the solution was concentrated under reduced pressure to remove MeOH, and the resulting acidic aqueous solution was diluted with sat. NaHCO$_3$. The slightly basic aqueous solution was then extracted (2×30% (CH$_3$)$_2$CHOH/CH$_2$Cl$_2$), washed (1×brine), dried (Na$_2$SO$_4$) and concentrated under reduced pressure to give 1.45 g of the product as a brown solid (4.47 mmol).

(g) N-[1-(3-fluorophenyl)-5-piperidino-1-ylmethyl-1H-benzoimidazol-2-yl]-3-trifluoromethyl-benzamide: 500 mg 1-(3-fluorophenyl)-5-piperidin-1-ylmethyl-1H-benzoimidazol-2-ylamine (1.54 mmol, 1.0 equiv) was combined in a flask with 877 mg O-benzotriazol-1-yl-N,N,N',N'-tetramethyluronium hexafluorophosphate (HBTU, 2.32 mmol, 1.5 equiv), 440 mg 3-trifluoromethylbenzoic acid (2.32 mmol, 1.5 equiv) and 312 mg 1-hydroxybenzotriazole hydrate (HOBT, 2.32 mmol, 1.5 equiv) followed by the addition of 12 mL DMF and 254 µL N-methylmorpholine (NMM, 2.32 mmol, 1.5 equiv). The solution was allowed to stir for 24 h and then diluted with sat. Na$_2$HCO$_3$. The solution was extracted (2×10% MeOH/CH$_2$Cl$_2$), washed (1×brine), dried (NaSO$_4$) and concentrated under reduced pressure. Purification by flash chromatography (SiO$_2$, 5% MeOH/CH$_2$Cl$_2$) gave 0.2 g of the product as a tan solid (0.2 mmol). $^1$H NMR (DMSO-d$_6$, 400 MHz) 13.0 (s, 1H), 8.35 (s, 1H), 8.30 (d, J=7.6 Hz, 1H), 7.88 (d, J=7.6 Hz, 1H), 7.72 (m, 3H), 7.62 (m, 2H), 7.47 (t, J=7.6 Hz, 1H), 7.22 (broad s, 2H), 3.55 (s, 2H), 2.38 (broad s, 4H), 1.5 (m, 6H).

Example 30

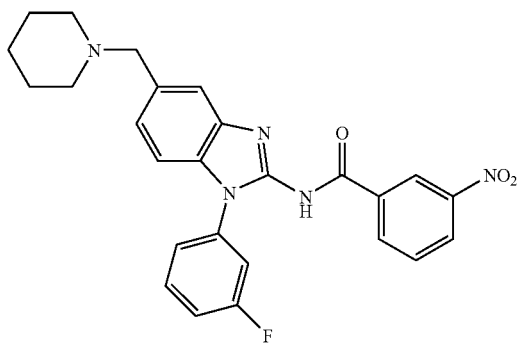

Synthesis of N-[1-(3-fluorophenyl)-5-piperidino-1-ylmethyl-1H-benzoimidazol-2-yl]-3-nitrobenzamide (69). Using the methods described above as in Example 29, and substituting 3-nitrobenzoic acid for 3-trifluorobenzoic acid in step (g) the following was prepared: N-[1-(3-fluorophenyl)-5-piperidino-1-ylmethyl-1H-benzoimidazol-2-yl]-3-nitrobenzamide: $^1$H NMR (DMSO-d$_6$, 400 MHz) 13.0 (s, 1H), 8.80 (s, 1H), 8.43 (d, J=7.4 Hz, 1H), 8.37 (d, J=7.4 Hz, 1H), 7.75 (m, 3H), 7.52 (m, 2H), 7.50 (t, J=7.4 Hz, 1H), 7.22 (broad s, 2H), 3.55 (s, 2H), 2.40 (broad s, 4 H), 1.5 (m, 6H).

Example 31

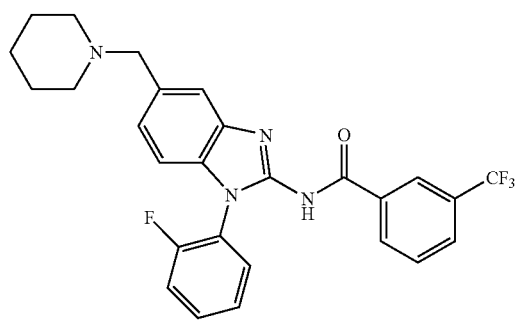

Synthesis of N-[1-(2-fluorophenyl)-5-piperidino-1-ylmethyl-1H-benzoimidazol-2-yl]-3-trifluoromethylbenzamide (71). Using the methods described above as in Example 29, and substituting 2-fluoroaniline for 3-fluoroaniline in step (d) the following was prepared: N-[1-(2-fluorophenyl)-5-piperidino-1-ylmethyl-1H-benzoimidazol-2-yl]-3-trifluoromethylbenzamide: $^1$H NMR (DMSO-d$_6$, 400 MHz) 13.0 (s, 1H), 8.26 (s, 1H), 8.25 (d, J=7.6 Hz, 1H), 7.88 (d, J=7.6 Hz, 1H), 7.82 (t, J=7.6 Hz, 1H), 7.68 (m, 4H), 7.52 (d, J=7.6 Hz, 1H), 7.25 (broad s, 1H), 7.05 (broad s, 1H), 3.55 (s, 2H), 2.38 (broad s, 4H), 1.5 (m, 6H).

Example 32

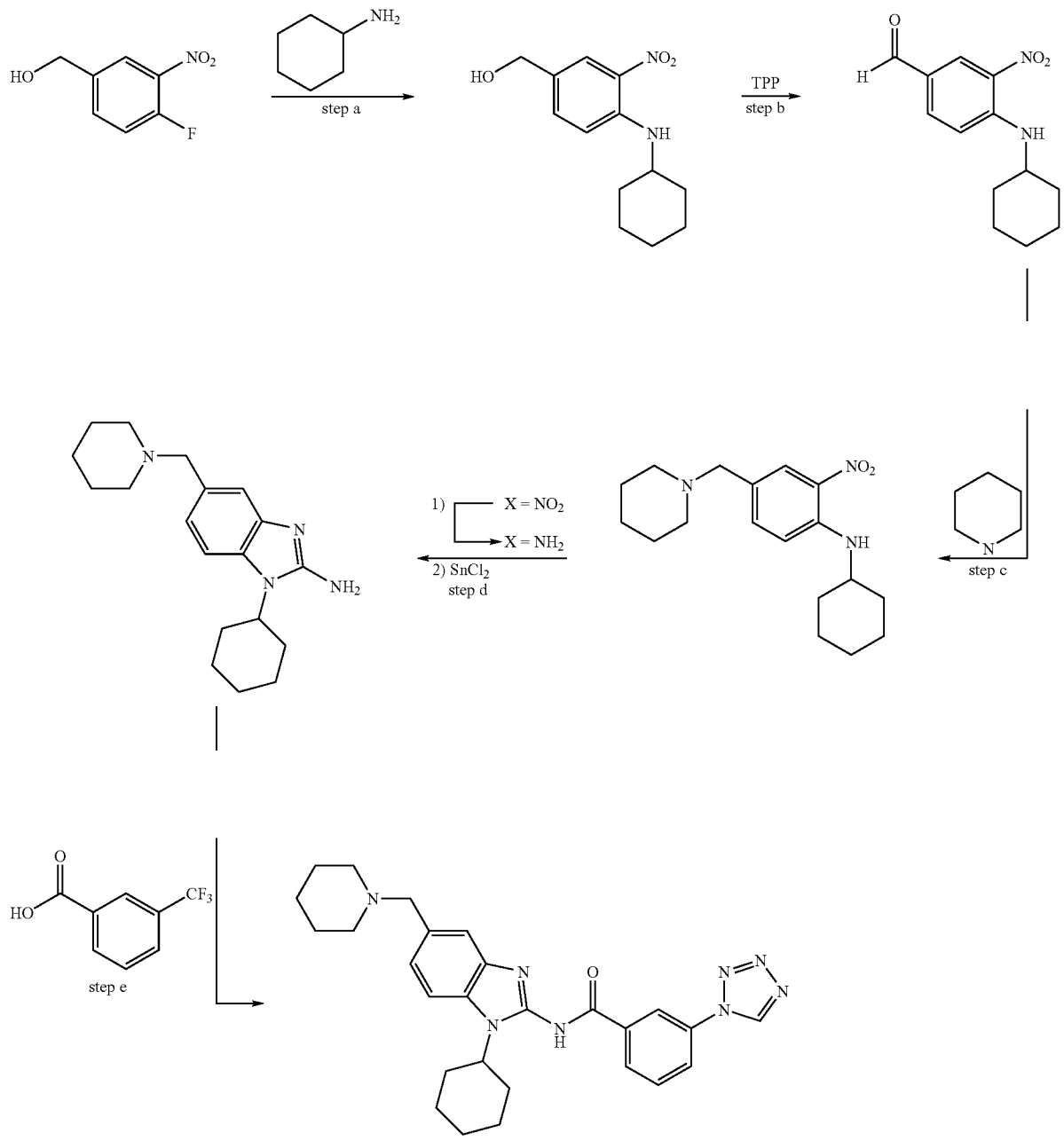

Synthesis of (N-(1-Cyclohexyl-5-piperidin-1-ylmethyl-1H-benzimidazol-2-yl)-3-(1-tetrazolyl)benzamide) (61). (a) A mixture of 4-fluoro-3-nitrobenzyl alcohol (prepared as in Example 29 above, 14.2 g, 82.9 mmol), cyclohexylamine (8.22 g, 82.9 mmol) and N,N-diisopropylethylamine (10.7 g, 82.8 mmol) was heated to 60° C. for 4 hr with vigorous stirring. The reaction mixture was then cooled, and ethyl acetate (400 mL) was added. The solution was then extracted with water (2×100 mL), dried over magnesium sulphate and evaporated to afford 4-cyclohexylamino-3-nitrobenzyl alcohol as an orange oil.

(b) To a solution of 4-cyclohexylamino-3-nitrobenzyl alcohol (21.0 g, 83 mmol) in DCM (300 mL) was added powdered 4A molecular sieves (15 g) and N-methyl morpholine-N-oxide monohydrate (10.8 g, 92.2 mmol). Tetra-n-propylammonium perruthenate (VII) (2.91 g, 8.28 mmol) was then added in a single portion. An initial exotherm was controlled using an ice bath, and then the reaction mixture was stirred at room temperature for 18 hr. The mixture was then reduced to ~100 mL by evaporation, and loaded onto a column of silica (400 g). The column was eluted with acetone:hexane 1:3 and the spot at 0.30 was collected, affording 4-cyclohexylamino-3-nitrobenzaldehyde as a yellow solid. (11.0 g, 44.3 mmol): $^1$H NMR (CDCl$_3$, 300 MHz) δ 9.60 (s, 1H), 8.32 (s, 1H), 7.71 (d, J=10 Hz, 1H), 6.73 (d, J=10 Hz, 1H) 3.46-3.32 (m, 1H), 1.90-1.15 (m, 10H).

(c) To a solution of 4-cyclohexylamino-3-nitrobenzaldehyde (10.3 g, 41.3 mmol) in dichloroethane (50 mL) was added piperidine (4.10 g, 48.2 mmol) followed by acetic acid (0.20 mL, cat.). The reaction mixture was heated to 60° C. and stirred for 1 hr, then cooled to room temperature and sodium triacetoxyborohydride (10.5 g, 49.5 mmol) was added in a single portion. After stirring for 18 hr at room temperature, the reaction was quenched by the addition of sodium bicarbonate (sat., aq., 100 mL), and the mixture was extracted with ethyl acetate (3×100 mL). The combined organic extracts were then evaporated to afford crude N-cyclohexyl-2-nitro-4-(1-piperidinylmethyl) aniline as a yellow oil (15.4 g crude yield).

(d) To the crude sample of N-cyclohexyl-2-nitro-4-(1-piperidinylmethyl) aniline prepared above (15.4 g) in ethanol (200 mL) was added tin (II) chloride dihydrate (40.0 g, 177 mmol) and the reaction mixture was heated to 50° C. and stirred for 16 hr. The Mixture was then cooled to room temperature, and sodium hydroxide (2N, aq.) was added until the pH was 13. Brine (100 mL) was then added and the mixture was extracted with ethyl acetate (3×250 mL). The combined extracts were then evaporated to afford 11.6 g of a brown oil. This crude product was then dissolved in ethanol (30 mL) and added over 30 min to a solution of cyanogen bromide (6 mL, 5N in acetonitrile, 30 mmol). The reaction mixture was then stirred at room temperature for 18 hr, and reduced to ~30 mL by evaporation. Ethyl acetate (50 mL) was then added, and the mixture extracted with hydrochloric acid (1 N, aq., 2×50 mL). The combined aqueous extracts were then basified to pH 10 with sodium hydroxide (6 N. aq.) and extracted with ethyl acetate (2×200 mL). The latter organic extracts were combined and evaporated to afford crude 1-cyclohexyl-5-piperidin-1-ylmethyl-1H-benzimidazol-2-amine (9.04 g) as a brown solid. This crude product was used in coupling reactions without further purification but for analytical purposes a 1 g portion was purified by HPLC to afford pure 1-cyclohexyl-5-piperidin-1-ylmethyl-1H-benzimidazol-2-amine as a white powder (320 mg, 1.02 mmol): $^1$H NMR (DMSO-d$_6$, 300 MHz) δ 8.71 (broad s, 2H), 7.82 (s, 1H), 7.43 (d, J=9.0 Hz, 1H), 7.28 (s, J=9.0 Hz, 1H), 4.39 (d, J=5 Hz, 1H), 3.35-1.16 (m, 20H). MS: API m/z 314 (M+H$^+$)

(e) To a solution of 1-cyclohexyl-5-piperidin-1-ylmethyl-1H-benzimidazol-2-amine (100 mg, 0.32 mmol, prepared above) and 3-(1-tetrazolyl)-benzoic acid (76 mg, 0.40 mmol) in N,N-dimethylformamide (2 mL) was added 1-hydroxybenzotriazole (57 mg, 0.42 mmol) followed by 1-(3-dimethylaminopropyl)carbodiimide hydrochloride (80 mg, 0.42 mmol). N,N-diisoproplethylamine (100 mg, 0.77 mmol) was then added and the solution was allowed to stir at room temperature. After 18 hr, the reaction mixture was diluted with N,N-dimethylformamide (2 mL) and water (1 mL), filtered, and purified without work-up by preparative scale HPLC. Freeze-drying afforded (N-(1-cyclohexyl-5-piperidin-1-ylmethyl-1H-benzimidazol-2-yl)-3-(1-tetrazolyl) benzamide) as a cream solid (27 mg, 0.056 mmol): $^1$H NMR (DMSO-d$_6$, 300 MHz) δ 10.20 (s, 1H), 9.30 (broad s, 1H), 8.63 (s, 1H), 8.34 (d, J=10.0 Hz, 1H), 8.02 (d, J=10 Hz, 1H), 7.81-7.64 (m, 2H), 7.64 (s, 1H), 7.33 (d, J=10.0 Hz, 1H), 4.83-4.63 (m, 1H), 4.41-4.29 (m, 2H), 2.99-1.33 (m, 18H). MS: API m/z 485 (M+H$^+$)

Example 33

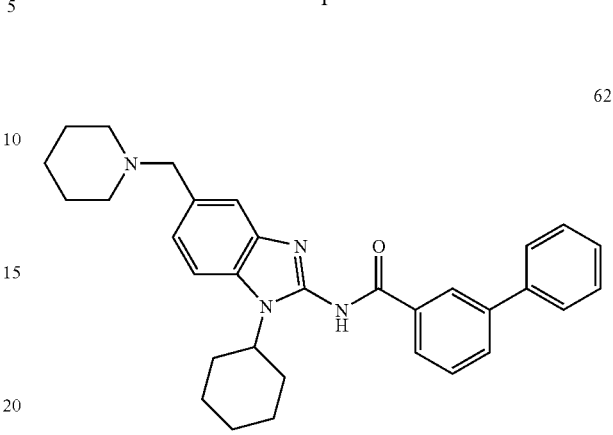

62

Synthesis of (N-(1-Cyclohexyl-5-piperidin-1-ylmethyl-1H-benzimidazol-2-yl)-3-phenylbenzamide) (62). Using the methods described in Example 32 substituting 3-phenylbenzoic acid for 3-(1-tetrazolyl)-benzoic acid the following was prepared: (N-(1-Cyclohexyl-5-piperidin-1-ylmethyl-1H-benzimidazol-2-yl)-3-phenylbenzamide): $^1$H NMR (DMSO-d$_6$, 300 MHz) δ 9.49 (broad s, 1H), 8.69 (s, 1H), 8.32 (d, J=10.0 Hz, 1H), 8.00-7.51 (m, 10H), 5.01-4.80 (m, 1H), 4.58-4.45 (m, 2H), 3.42-1.43 (m, 18H). MS: API m/z 493 (M+H$^+$)

Example 34

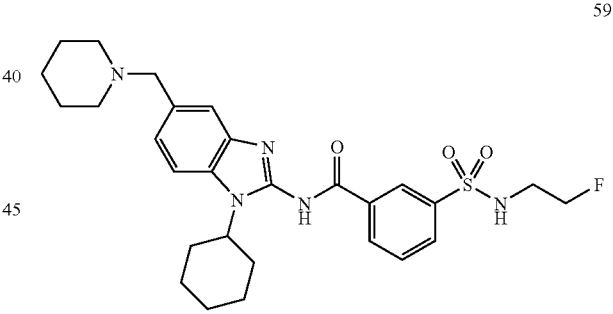

59

Synthesis of (N-(1-Cyclohexyl-5-piperidin-1-ylmethyl-1H-benzimidazol-2-yl)-3-(2-fluoro-ethylsulfamoyl)benzamide) (59). Using the methods described in Example 32 substituting (2-fluoroethylsulfamoyl)benzoic acid for 3-(1-tetrazolyl)-benzoic acid the following was prepared: (N-(1-Cyclohexyl-5-piperidin-1-ylmethyl-1H-benzimidazol-2-yl)-3-(2-fluoro-ethylsulfamoyl)benzamide).

The benzoic acid was prepared as follows: To a solution of 2-fluoroethylamide (945 mg, 15 mmol) in dichloromethane (20 mL) was added 3-chlorosulfonylbenzoic acid (1.20 g, 5.44 mmol). After stirring at room temperature for 16 hr, the reaction mixture was diluted with ethyl acetate (50 mL) and extracted with sodium hydroxide (2×50 mL, 1N, aq.). The combined aqueous extracts were acidified to pH 5. The mixture was then filtered to afford (2-fluoroethylsulfamoyl)benzoic acid (640 mg) as a white powder which was used in the synthesis of the title compound without further purification.

(N-(1-Cyclohexyl-5-piperidin-1-ylmethyl-1H-benzimidazol-2-yl)-3-(2-fluoro-ethylsulfamoyl)benzamide): $^1$H NMR (DMSO-$d_6$, 300 MHz) δ 9.22 (broad s, 1H), 8.53 (s, 1H), 8.38 (d, J=10.0 Hz, 1H), 8.00 (t, J=6.0 Hz, 1H), 7.82 (d, J=10.0 Hz, 1H), 7.70 (d, J=11.0 Hz, 1H), 7.62 (t, J=10.0 Hz, 1H), 7.53 (s, 1H), 7.25 (d, J=11.0 Hz, 1H), 4.88-4.65 (m, 1H), 4.32 (dt, J=6.0, 42.0 Hz, 2H), 4.30-4.18 (m 2 H), 3.02 (dq, J=6.0, 22.0 Hz, 2H), 2.84-1.25 (m, 18H). MS: API m/z 542 (M+H$^+$)

Example 35

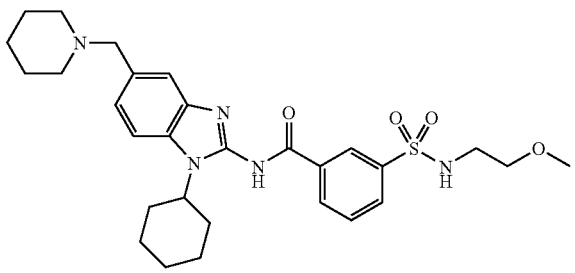

57

Synthesis of (N-(1-Cyclohexyl-5-piperidin-1-ylmethyl-1H-benzimidazol-2-yl)-3-(2-methoxy-ethylsulfamoyl)benzamide) (57). Using the methods described in examples 32 and 34 substituting (2-methoxyethylsulfamoyl)benzoic acid for 3-(1-tetrazolyl)benzoic acid the following was prepared: (N-(1-Cyclohexyl-5-piperidin-1-ylmethyl-1H-benzimidazol-2-yl)-3-(2-methoxy-ethylsulfamoyl)-benzamide): $^1$H NMR (DMSO-$d_6$, 300 MHz) δ 9.24 (broad s, 1H), 8.64 (s, 1H), 8.43 (d, J=10.0 Hz, 1H), 7.89 (d, J=10.0 Hz, 1H), 7.85-7.72 (m, 2H), 7.69 (t, J=10.0 Hz, 1H), 7.63 (1H, s, benzimidazole C4-$\underline{H}$), 7.31 (1 H, d, J=11 Hz, benzimidazole C6-$\underline{H}$), 4.91-4.70 (s, 1H), 4.36-4.25 (m, 2H), 3.18 (s, 3H), 2.96-1.40 (m, 20H). MS: API m/z 554 (M+H$^+$).

Example 36

Enzymatic inhibition assay. This example provides a method that is useful for evaluating test compounds for inhibition of IRAK-1 or IRAK-4 kinase activity.

Protocol 96-well polystyrene microtiter plates were coated with neutravidin for IRAK-1 or streptavidin for IRAK-4 (10 mg/mL in PBS, overnight at 4° C.). The coating solution was removed and in 80 μL/well a kinase reaction mixture was added (for IRAK-1: 20 mM Tris-HCl, pH 7.5, 10 mM MgCl$_2$, 2 mM EGTA, 1 mM NaF, 0.5 mM benzamidine, 1 mM DTT, 3 μM ATP, 1 mM of biotinylated substrate peptide bio-ARF-SRFAGSSPSQSSMVAR, sequence derived from IRAK-1; for IRAK-4: 20 mM Tris-HCl, pH 7.5, 10 mM MgCl$_2$, 2 mM EGTA, 1 mM NaF, 0.5 mM benzamidine, 1 mM DTT, 10% glycerol, 10 μM ATP, 1 mM of biotinylated substrate peptide bio-RRRVTSPARRS, sequence derived from GFAP).

At 10 μL/well in DMSO test compounds were added covering a final concentration range from 1 nM to 30 mM. Recombinant, full-length IRAK-1 or IRAK-4 enzyme (baculovirus expression system) was added in 10 μL buffer containing Tris-HCl pH 7.5 20 mM, EGTA 2 mM, benzamidine 0.5 mM, DTT 1 mM, MgCl$_2$ 10 mM and glycerol 10% (IRAK-4 only) to initiate the kinase reaction. The reaction mixture was incubated at room temperature for 60 min on a shaker. During this incubation the substrate peptide is being phosphorylated by the kinase and gets captured onto the surface of the wells by neutravidin or streptavidin, respectively. The plate was washed 3× with 150 μL distilled water to terminate the reaction and remove components of the reaction mixture. A conventional chemiluminescent ELISA detection technique was initiated by adding 100 μL/well primary antibody (monoclonal antibody YC10, generated to recognize the phosphorylated epitope in the substrate peptide; used at 1:20,000 dilution for IRAK-1 and 1:10,000 dilution for IRAK-4) premixed with horseradish peroxidase (HRP) conjugated anti-mouse secondary antibody (commercially available from several sources; used at 1:10,000 dilution) in PBS containing 2% BSA. The solution was incubated at room temperature for 40 min on a shaker, then washed 3× with 150 μL of water. 100 μL/well 10× diluted SuperSignal HRP substrate (from Pierce) was added and after 5 min incubation the chemiluminescent signal was captured by a Labsystems LuminoSkan luminometer. The point of 50% inhibition of IRAK-1 or IRAK-4 enzyme activity (IC$_{50}$) was determined (see Table 1).

TABLE 1

IC$_{50}$ values (μM) for exemplary compounds of the invention.

| Compound | IRAK-1 | IRAK-4 |
|---|---|---|
| 1 | ++ | ++ |
| 2 | + | ++ |
| 3 | ++ | ++ |
| 4 | ++ | ++ |
| 5 | ++ | ++ |
| 6 | + | ++ |
| 7a | ++ | ++ |
| 8 | + | + |
| 9 | ++ | ++ |
| 10 | + | ++ |
| 11 | ++ | ++ |
| 12 | ++ | ++ |
| 13 | ++ | ++ |
| 14 | + | + |
| 15a | ++ | ++ |
| 16 | ++ | ++ |
| 17 | + | + |
| 19 | + | + |
| 20 | ++ | ++ |
| 21 | + | ND |
| 22 | ++ | ++ |
| 23 | ++ | ++ |
| 24 | ++ | ++ |
| 25 | ++ | ++ |
| 26 | ++ | ++ |
| 27 | ++ | ++ |
| 28 | ++ | ++ |
| 29 | ++ | ++ |
| 30 | ++ | ++ |
| 31 | ++ | ++ |
| 32 | ++ | ++ |

+ indicates 10 μM < IC$_{50}$ ≤ 30 μM
++ indicates IC$_{50}$ ≤ 10 μM
ND indicates IC$_{50}$ not determined Sequences IRAK-1 has a N-terminal Flag tag for purification. IRAK-4 has a N-terminal His Tag. An amino acid spacer is between Tag and the kinase.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Without in any way limiting the foregoing, although some of the methods recited in the appended claims incorporate a compound of, for example, claim 1, the methods may also apply to the compounds recited in other claims and the compounds disclosed throughout the specification.

What is claimed is:

1. A compound having a formula of

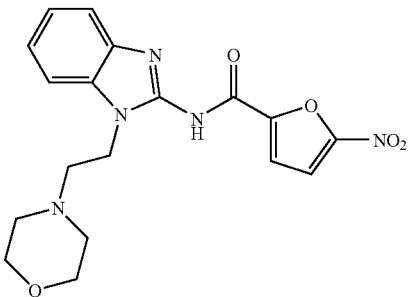

or pharmaceutically acceptable salt thereof.

* * * * *